(12) United States Patent
Hogan et al.

(10) Patent No.: US 10,640,835 B2
(45) Date of Patent: May 5, 2020

(54) MICROARRAY BASED MULTIPLEX PATHOGEN ANALYSIS AND USES THEREOF

(71) Applicants: Michael Edward Hogan, Stony Brook, NY (US); Melissa Rose May, Tucson, AZ (US); Frederick Henry Eggers, Sahuarita, AZ (US)

(72) Inventors: Michael Edward Hogan, Stony Brook, NY (US); Melissa Rose May, Tucson, AZ (US); Frederick Henry Eggers, Sahuarita, AZ (US)

(73) Assignee: PathogenDX Inc, Scottsdale, AZ (US)

( * ) Notice: Subject to any disclaimer, the term of this patent is extended or adjusted under 35 U.S.C. 154(b) by 0 days.

(21) Appl. No.: 16/581,054

(22) Filed: Sep. 24, 2019

(65) Prior Publication Data

US 2020/0017925 A1    Jan. 16, 2020

Related U.S. Application Data

(60) Division of application No. 16/158,276, filed on Oct. 11, 2018, now Pat. No. 10,513,745, which is a (Continued)

(51) Int. Cl.
*C12Q 1/6895* (2018.01)
*C12Q 1/689* (2018.01)
(Continued)

(52) U.S. Cl.
CPC .......... *C12Q 1/6895* (2013.01); *C12Q 1/686* (2013.01); *C12Q 1/689* (2013.01); *C12Q 1/6837* (2013.01);
(Continued)

(58) Field of Classification Search
CPC .... C12Q 1/6895; C12Q 1/6837; C12Q 1/682; C12Q 1/6846; C12Q 1/6853; C12Q 1/686;
(Continued)

(56) References Cited

U.S. PATENT DOCUMENTS 6,312,960 B1 * 11/2001 Balch ................... B01J 19/0046
422/105
2009/0011949 A1 * 1/2009 Hogan ................. B01J 19/0046
506/9
(Continued)

OTHER PUBLICATIONS

Lee et al. The ISME Journal. 2013. 7:1974-1984. (Year: 2013).*
Brunschot et al. PLoS ONE. 2014. 9(1):e84743. (Year: 2014).*
Lievens et al. 2005. Phytopathology. 95(12):1374-1380. (Year: 2005).*

(Continued)

*Primary Examiner* — Joseph G. Dauner
(74) *Attorney, Agent, or Firm* — Benjamin Aaron Adler

(57) ABSTRACT

Provided herein is an internal standard method for determining copy number of a pathogen DNA in an unpurified nucleic acid sample by using a known copy number of synthetic DNA that shares a consensus region sequence with the pathogen. The sample is subject to two amplification steps using locus-specific primers and fluorescent primers respectively to obtain fluorescent amplicons for the pathogen and synthetic DNA. These are hybridized with immobilized pathogen-specific and synthetic DNA-specific nucleic acid probes and imaged to obtain fluorescent signals for pathogen-specific and synthetic DNA-specific amplicons. Signal intensities are correlated with the known copy number of synthetic DNA to determine copy number of pathogen DNA in the plant. Also described herein is a method to simultaneously quantitate using the above method, copy numbers of both pathogen and plant DNA in a sample.

15 Claims, 21 Drawing Sheets

Specification includes a Sequence Listing.

Related U.S. Application Data continuation-in-part of application No. 15/916,036, filed on Mar. 8, 2018, now Pat. No. 10,612,075, which is a continuation-in-part of application No. 15/388,561, filed on Dec. 22, 2016.

(60) Provisional application No. 62/271,371, filed on Dec. 28, 2015.

(51) Int. Cl.
| | |
|---|---|
| *C12Q 1/686* | (2018.01) |
| *C12Q 1/6874* | (2018.01) |
| *C12Q 1/6844* | (2018.01) |
| *C12Q 1/6837* | (2018.01) |
| *C12Q 1/6853* | (2018.01) |
| *G16B 30/00* | (2019.01) |
| *G16B 25/10* | (2019.01) |
| *G16B 20/00* | (2019.01) |

(52) U.S. Cl.
CPC ......... *C12Q 1/6846* (2013.01); *C12Q 1/6853* (2013.01); *C12Q 1/6874* (2013.01); *G16B 20/00* (2019.02); *G16B 25/10* (2019.02); *G16B 30/00* (2019.02)

(58) Field of Classification Search
CPC .... C12Q 1/689; C12Q 1/6874; C12Q 1/6893; G16B 30/00
See application file for complete search history.

(56) References Cited

U.S. PATENT DOCUMENTS

| | | | | |
|---|---|---|---|---|
| 2010/0129821 | A1* | 5/2010 | Fredricks | C12Q 1/6895 435/6.15 |
| 2011/0111970 | A1* | 5/2011 | Tzean | C12Q 1/6895 506/9 |
| 2014/0342947 | A1* | 11/2014 | Hogan | B01J 19/123 506/18 |
| 2016/0319379 | A1* | 11/2016 | Lloyd, Jr. | C12Q 1/689 |
| 2018/0251758 | A1* | 9/2018 | Hogan | C12N 15/1086 |
| 2018/0251822 | A1* | 9/2018 | Hogan | C12Q 1/6837 |
| 2019/0032046 | A1* | 1/2019 | Hogan | C12N 15/1086 |
| 2019/0085414 | A1* | 3/2019 | Hogan | C12Q 1/6895 |
| 2019/0085415 | A1* | 3/2019 | Hogan | C12Q 1/6895 |

OTHER PUBLICATIONS

Lievens et al. FEMS Microbiology Letters. 2003. 223:113-122. (Year: 2003).*

Tsui et al . IMA Fungus. 2011. 2(2):177-189. (Year: 2011).*

* cited by examiner 16S rDNA Locus (All Bacteria)

Stx1 Locus (Pathogenic *E.coli*)

| Identification Panel | | | | | |
|---|---|---|---|---|---|
| Sample | 1 | 2 | 3 | 4 | 5 |
| Cannabis DNA control | 29348 | 18804 | 17983 | 14549 | 14960 |
| Aeromonas | 137 | 145 | 245 | 138 | 382 |
| E.coli | 132 | 145 | 144 | 124 | 389 |
| E.coli specific gene | 563 | 471 | 461 | 1205 | 6408 |
| Enterobacteriacea | 136 | 14805 | 14246 | 149 | 24071 |
| Listeria | 142 | 163 | 142 | 133 | 311 |
| Pseudomonas | 112 | 1895 | 2033 | 102 | 1579 |
| Pseudomonas aeruginosa | 153 | 1140 | 992 | 121 | 2290 |
| Salmonella/Enterobacter | 125 | 285 | 616 | 126 | 742 |
| Salmonella specific gene | 199 | 201 | 207 | 164 | 320 |
| Xanthomonas | 119 | 151 | 141 | 106 | 213 |
| Aspergillus fumigatus | 33335 | 9241 | 3861 | 3676 | 6224 |
| Aspergillus flavus | 1228 | 112 | 1198 | 136 | 2955 |
| Aspergillus niger | 139 | 119 | 161 | 142 | 691 |
| Botrytis | 159 | 142 | 182 | 120 | 181 |
| Penicillium | 154 | 182 | 153 | 100 | 2504 |
| Fusarium solani | 132 | 115 | 127 | 111 | 135 |
| Mucor | 122 | 139 | 129 | 130 | 129 |
| Candida | 286 | 173 | 415 | 108 | 129 |

| Cannabis DNA control | Cannabis Wash | Candida albicans Vitriod |
|---|---|---|
| Cannabis DNA control 1 | 1810 | 113 |
| Cannabis DNA control 2 | 9203 | 124 |
| Low Pan Fungal Control | 9526 | 14051 |
| Medium Pan Fungal Control | 21814 | 37310 |
| High Pan Fungal Control | 41190 | 65000 |
| Negative control | 45 | 131 |
| Aspergillus fumigatus | 292 | 152 |
| Aspergillus flavus | 39 | 135 |
| Aspergillus niger | 37 | 130 |
| Botrytis | 29 | 228 |
| Penicillium | 34 | 118 |
| Fusarium solani | 42 | 126 |
| Mucor | 39 | 121 |
| Candida Group 1 | 2695 | 6885 |
| Candida albicans | 37 | 10386 |
| Isaria Biofoliar | 29 | 126 |
| Myrothesium Biofoliar | 135 | 121 |
| Pythium Biofoliar | 153 | 189 |

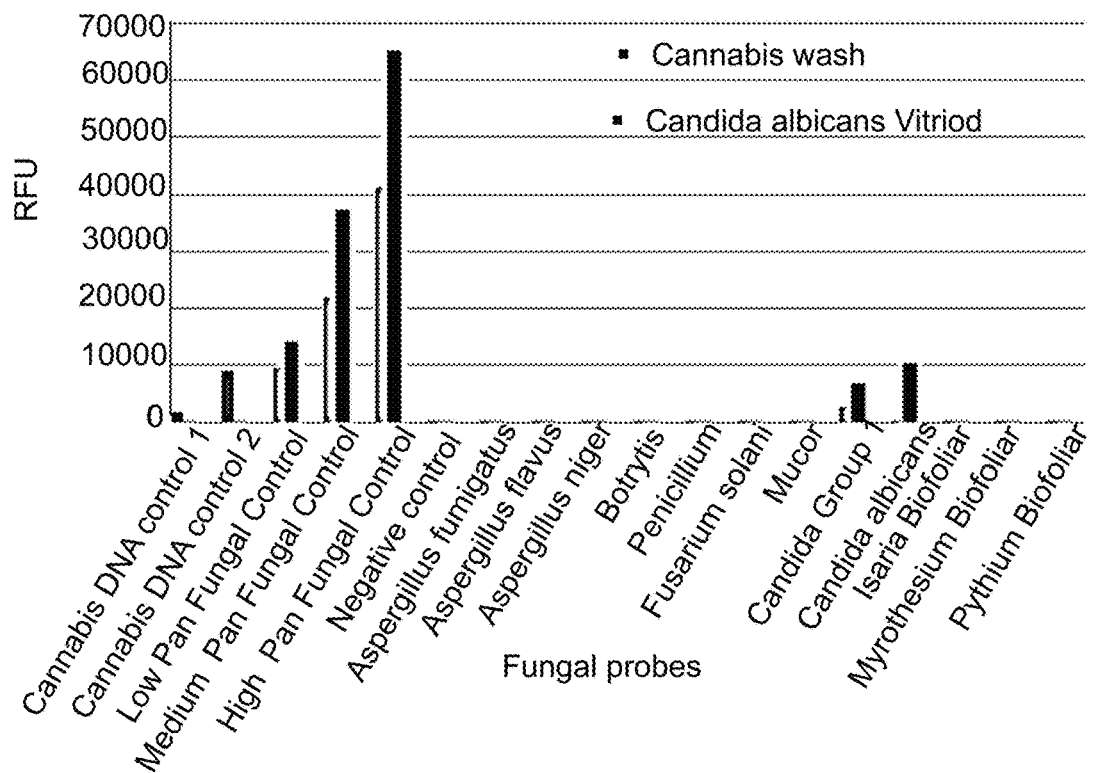

FIG. 13

SEQUENCE LISTING

<160> NUMBER OF SEQ ID NOS: 157

<210> SEQ ID NO 1
<211> LENGTH: 23
<212> TYPE: DNA
<213> ORGANISM: Artificial Sequence
<220> FEATURE:
<223> OTHER INFORMATION: Forward primer for amplification of the 16S
      rDNA HV3 locus in all bacteria

<400> SEQUENCE: 1
tttcacaytg gractgagac acg                                          23

<210> SEQ ID NO 2
<211> LENGTH: 27
<212> TYPE: DNA
<213> ORGANISM: Artificial Sequence
<220> FEATURE:
<223> OTHER INFORMATION: Reverse primer for amplification of the 16S
      rDNA HV3 locus in all bacteria

<400> SEQUENCE: 2
tttgactacc agggtatcta atcctgt                                      27

<210> SEQ ID NO 3
<211> LENGTH: 28
<212> TYPE: DNA
<213> ORGANISM: Artificial Sequence
<220> FEATURE:
<223> OTHER INFORMATION: Forward primer for amplification of the Stx1
      locus in pathogenic Escherichia coli

<400> SEQUENCE: 3
tttataatct acggcttatt gttgaacg                                     28

<210> SEQ ID NO 4
<211> LENGTH: 29
<212> TYPE: DNA
<213> ORGANISM: Artificial Sequence
<220> FEATURE:
<223> OTHER INFORMATION: Reverse primer for amplification of the Stx1
      locus in pathogenic Escherichia coli

<400> SEQUENCE: 4
tttggtatag ctactgtcac cagacaatg                                    29

<210> SEQ ID NO 5
<211> LENGTH: 26
<212> TYPE: DNA
<213> ORGANISM: Artificial Sequence
<220> FEATURE:
<223> OTHER INFORMATION: Forward primer for amplification of the Stx2
      locus in pathogenic Escherichia coli

<400> SEQUENCE: 5
tttgatgcat ccagagcagt tctgcg                                       26

<210> SEQ ID NO 6
<211> LENGTH: 27
<212> TYPE: DNA
<213> ORGANISM: Artificial Sequence
<220> FEATURE:
<223> OTHER INFORMATION: Reverse primer for amplification of the Stx2
      locus in pathogenic Escherichia coli

<400> SEQUENCE: 6
tttgtgaggt ccacgtctcc cggcgtc                                      27

<210> SEQ ID NO 7
<211> LENGTH: 28
<212> TYPE: DNA
<213> ORGANISM: Artificial Sequence
<220> FEATURE:
<223> OTHER INFORMATION: Forward primer for amplification of the InvA
      locus in all Salmonella

<400> SEQUENCE: 7
tttattatcg ccacgttcgg gcaattcg                                      28

<210> SEQ ID NO 8
<211> LENGTH: 28
<212> TYPE: DNA
<213> ORGANISM: Artificial Sequence
<220> FEATURE:
<223> OTHER INFORMATION: Reverse primer for amplification of the InvA
      locus in all Salmonella

<400> SEQUENCE: 8
tttcttcatc gcaccgtcaa aggaaccg                                      28

<210> SEQ ID NO 9
<211> LENGTH: 26
<212> TYPE: DNA
<213> ORGANISM: Artificial Sequence
<220> FEATURE:
<223> OTHER INFORMATION: Forward primer for amplification of the tuf
      locus in all Escherichia coli

<400> SEQUENCE: 9
tttcagagtg ggaagcgaaa atcctg                                        26

<210> SEQ ID NO 10
<211> LENGTH: 26
<212> TYPE: DNA
<213> ORGANISM: Artificial Sequence
<220> FEATURE:
<223> OTHER INFORMATION: Reverse primer for amplification of the tuf
      locus in all Escherichia coli

<400> SEQUENCE: 10
tttacgccag tacaggtaga cttctg                                        26

<210> SEQ ID NO 11
<211> LENGTH: 30
<212> TYPE: DNA
<213> ORGANISM: Artificial Sequence
<220> FEATURE:
<223> OTHER INFORMATION: Forward primer for amplification of the 16S
      rDNA HV3 locus in Enterobacteriaceae

<400> SEQUENCE: 11
ttaccttcgg gcctcttgcc atcrgatgtg                                    30

<210> SEQ ID NO 12
<211> LENGTH: 33
<212> TYPE: DNA
<213> ORGANISM: Artificial Sequence
<220> FEATURE:
<223> OTHER INFORMATION: Reverse primer for amplification of the 16S
      rDNA HV3 locus in Enterobacteriaceae

<400> SEQUENCE: 12
ttggaattct acccccctct acragactca agc                                33

<210> SEQ ID NO 13
<211> LENGTH: 26
<212> TYPE: DNA
<213> ORGANISM: Artificial Sequence
<220> FEATURE:
<223> OTHER INFORMATION: Forward primer for amplification of the ITS2
      locus in all yeast and mold/fungi

<400> SEQUENCE: 13
tttactttya acaayggatc tcttgg                                           26

<210> SEQ ID NO 14
<211> LENGTH: 26
<212> TYPE: DNA
<213> ORGANISM: Artificial Sequence
<220> FEATURE:
<223> OTHER INFORMATION: Reverse primer for amplification of the ITS2
      locus in all yeast and mold/fungi

<400> SEQUENCE: 14
tttcttttcc tccgcttatt gatatg                                           26

<210> SEQ ID NO 15
<211> LENGTH: 28
<212> TYPE: DNA
<213> ORGANISM: Artificial Sequence
<220> FEATURE:
<223> OTHER INFORMATION: Forward primer for amplification of the ITS2
      locus in Aspergillus spp

<400> SEQUENCE: 15
tttaaaggca gcggcggcac cgcgtccg                                         28

<210> SEQ ID NO 16
<211> LENGTH: 27
<212> TYPE: DNA
<213> ORGANISM: Artificial Sequence
<220> FEATURE:
<223> OTHER INFORMATION: Reverse primer for amplification of the ITS2
      locus in Aspergillus spp

<400> SEQUENCE: 16
ttttcttttc ctccgcttat tgatatg                                          27

<210> SEQ ID NO 17
<211> LENGTH: 25
<212> TYPE: DNA
<213> ORGANISM: Artificial Sequence
<220> FEATURE:
<223> OTHER INFORMATION: Forward primer for amplification of the ITS1
      locus in Cannabis/plant

<400> SEQUENCE: 17
tttgcaacag cagaacgacc cgtga                                            25

<210> SEQ ID NO 18
<211> LENGTH: 25
<212> TYPE: DNA
<213> ORGANISM: Artificial Sequence
<220> FEATURE:
<223> OTHER INFORMATION: Reverse primer for amplification of the ITS1
      locus in Cannabis/plant

<400> SEQUENCE: 18
tttcgataaa cacgcatctc gattg                                            25

<210> SEQ ID NO 19
<211> LENGTH: 24
<212> TYPE: DNA
<213> ORGANISM: Artificial Sequence
<220> FEATURE:
<223> OTHER INFORMATION: Forward primer for amplification of the 16S
      rDNA HV3 locus in all bacteria

<400> SEQUENCE: 19
tttactgaga cacggyccar actc                                            24

<210> SEQ ID NO 20
<211> LENGTH: 24
<212> TYPE: DNA
<213> ORGANISM: Artificial Sequence
<220> FEATURE:
<223> OTHER INFORMATION: Reverse primer for amplification of the 16S
      rDNA HV3 Locus in all bacteria

<400> SEQUENCE: 20
tttgtattac cgcggctgct ggca                                            24

<210> SEQ ID NO 21
<211> LENGTH: 28
<212> TYPE: DNA
<213> ORGANISM: Artificial Sequence
<220> FEATURE:
<223> OTHER INFORMATION: Forward primer for amplification of the Stx1
      locus in pathogenic Escherichia coli

<400> SEQUENCE: 21
tttatgtgac aggatttgtt aacaggac                                        28

<210> SEQ ID NO 22
<211> LENGTH: 28
<212> TYPE: DNA
<213> ORGANISM: Artificial Sequence
<220> FEATURE:
<223> OTHER INFORMATION: Reverse primer for amplification of the Stx1
      locus in pathogenic Escherichia coli

<400> SEQUENCE: 22
tttctgtcac cagacaatgt aaccgctg                                        28

<210> SEQ ID NO 23
<211> LENGTH: 24
<212> TYPE: DNA
<213> ORGANISM: Artificial Sequence
<220> FEATURE:
<223> OTHER INFORMATION: Forward primer for amplification of the Stx2
      locus in pathogenic Escherichia coli

<400> SEQUENCE: 23 tttttgtcact gtcacagcag aag   24

<210> SEQ ID NO 24
<211> LENGTH: 25
<212> TYPE: DNA
<213> ORGANISM: Artificial Sequence
<220> FEATURE:
<223> OTHER INFORMATION: Reverse primer for amplification of the Stx2
      locus in pathogenic Escherichia coli

<400> SEQUENCE: 24
tttgcgtcat cgtatacaca ggagc                                           25

<210> SEQ ID NO 25
<211> LENGTH: 26

```
<212> TYPE: DNA
<213> ORGANISM: Artificial Sequence
<220> FEATURE:
<223> OTHER INFORMATION: Forward primer for amplification of the InvA
      locus in all Salmonella us

<400> SEQUENCE: 25
ttttatcgtt attaccaaag gttcag                                        26

<210> SEQ ID NO 26
<211> LENGTH: 28
<212> TYPE: DNA
<213> ORGANISM: Artificial Sequence
<220> FEATURE:
<223> OTHER INFORMATION: Reverse primer for amplification of the InvA
      locus in all Salmonella

<400> SEQUENCE: 26
tttcctttcc agtacgcttc gccgttcg                                      28

<210> SEQ ID NO 27
<211> LENGTH: 25
<212> TYPE: DNA
<213> ORGANISM: Artificial Sequence
<220> FEATURE:
<223> OTHER INFORMATION: Forward primer for amplification of the tuf
      locus in all Escherichia coli

<400> SEQUENCE: 27
tttgttgtta ccggtcgtgt agaac                                         25

<210> SEQ ID NO 28
<211> LENGTH: 28
<212> TYPE: DNA
<213> ORGANISM: Artificial Sequence
<220> FEATURE:
<223> OTHER INFORMATION: Reverse primer for amplification of the tuf
      locus in all Escherichia coli

<400> SEQUENCE: 28
tttcttctga gtctctttga taccaacg                                      28

<210> SEQ ID NO 29
<211> LENGTH: 30
<212> TYPE: DNA
<213> ORGANISM: Artificial Sequence
<220> FEATURE:
<223> OTHER INFORMATION: Forward primer for amplification of the 16S
      rDNA HV3 locus in Enterobacteriaceae

<400> SEQUENCE: 29
ttatattgca caatgggcgc aagcctgatg                                    30

<210> SEQ ID NO 30
<211> LENGTH: 25
<212> TYPE: DNA
<213> ORGANISM: Artificial Sequence
<220> FEATURE:
<223> OTHER INFORMATION: Reverse primer for amplification of the 16S
      rDNA HV3 locus in Enterobacteriaceae

<400> SEQUENCE: 30
ttttgtatta ccgcggctgc tggca                                         25

<210> SEQ ID NO 31
<211> LENGTH: 23
<212> TYPE: DNA
```

<213> ORGANISM: Artificial Sequence
<220> FEATURE:
<223> OTHER INFORMATION: Forward primer for amplification of the ITS2
      locus in all yeast and mold/fungi

<400> SEQUENCE: 31
tttgcatcga tgaagarcgy agc                                           23

<210> SEQ ID NO 32
<211> LENGTH: 22
<212> TYPE: DNA
<213> ORGANISM: Artificial Sequence
<220> FEATURE:
<223> OTHER INFORMATION: Reverse primer for amplification of the ITS2
      locus in all yeast and mold/fungi

<400> SEQUENCE: 32
tttcctccgc ttattgatat gc                                            22

<210> SEQ ID NO 33
<211> LENGTH: 26
<212> TYPE: DNA
<213> ORGANISM: Artificial Sequence
<220> FEATURE:
<223> OTHER INFORMATION: Forward primer for amplification of the ITS2
      locus in Aspergillus spp

<400> SEQUENCE: 33
tttcctcgag cgtatggggc tttgtc                                        26

<210> SEQ ID NO 34
<211> LENGTH: 24
<212> TYPE: DNA
<213> ORGANISM: Artificial Sequence
<220> FEATURE:
<223> OTHER INFORMATION: Reverse primer for amplification of the ITS2
      locus in Aspergillus spp

<400> SEQUENCE: 34
tttttcctcc gcttattgat atgc                                          24

<210> SEQ ID NO 35
<211> LENGTH: 27
<212> TYPE: DNA
<213> ORGANISM: Artificial Sequence
<220> FEATURE:
<223> OTHER INFORMATION: Forward primer for amplification of the ITS1
      locus in Cannabis plant

<400> SEQUENCE: 35
tttcgtgaac acgttttaaa cagcttg                                       27

<210> SEQ ID NO 36
<211> LENGTH: 24
<212> TYPE: DNA
<213> ORGANISM: Artificial Sequence
<220> FEATURE:
<223> OTHER INFORMATION: Reverse primer for amplification of the ITS1
      locus in Cannabis/plant

<400> SEQUENCE: 36
tttccaccgc acgagccacg cgat                                          24

<210> SEQ ID NO 37
<211> LENGTH: 30
<212> TYPE: DNA
<213> ORGANISM: Artificial Sequence

```
<220> FEATURE:
<223> OTHER INFORMATION: Probe sequence for the 16S locus for total
      aerobic bacteria with high sensitivity

<400> SEQUENCE: 37
tttttttttc ctacgggagg cagttttttt                                    30

<210> SEQ ID NO 38
<211> LENGTH: 30
<212> TYPE: DNA
<213> ORGANISM: Artificial Sequence
<220> FEATURE:
<223> OTHER INFORMATION: Probe sequence for the 16S locus for total
      aerobic bacteria with medium sensitivity

<400> SEQUENCE: 38
ttttttttcc ctacgggagg catttttttt                                    30

<210> SEQ ID NO 39
<211> LENGTH: 30
<212> TYPE: DNA
<213> ORGANISM: Artificial Sequence
<220> FEATURE:
<223> OTHER INFORMATION: Probe sequence for the 16S locus for total
      aerobic bacteria with low sensitivity

<400> SEQUENCE: 39
tttattttcc ctacgggagg cttttatttt                                    30

<210> SEQ ID NO 40
<211> LENGTH: 30
<212> TYPE: DNA
<213> ORGANISM: Artificial Sequence
<220> FEATURE:
<223> OTHER INFORMATION: Probe sequence for the 16S locus in
      Enterobacteriaceae with low sensitivity

<400> SEQUENCE: 40
tttattctat tgacgttacc catttatttt                                    30

<210> SEQ ID NO 41
<211> LENGTH: 30
<212> TYPE: DNA
<213> ORGANISM: Artificial Sequence
<220> FEATURE:
<223> OTHER INFORMATION: Probe sequence for the 16S locus in
      Enterobacteriaceae with medium sensitivity

<400> SEQUENCE: 41 tttttctat tgacgttacc cgtttttttt                                     30

<210> SEQ ID NO 42
<211> LENGTH: 30
<212> TYPE: DNA
<213> ORGANISM: Artificial Sequence
<220> FEATURE:
<223> OTHER INFORMATION: Probe sequence for the 16S locus in Escherichia
      coli and Shigella

<400> SEQUENCE: 42
ttttctaata cctttgctca ttgactcttt                                    30

<210> SEQ ID NO 43
<211> LENGTH: 30
<212> TYPE: DNA
<213> ORGANISM: Artificial Sequence
<220> FEATURE:
```

```
<223> OTHER INFORMATION: Probe sequence for the 16S locus in Escherichia
      coli and Shigella

<400> SEQUENCE: 43 tttttttaagg gagtaaagtt aatattttt                                            30

<210> SEQ ID NO 44
<211> LENGTH: 30
<212> TYPE: DNA
<213> ORGANISM: Artificial Sequence
<220> FEATURE:
<223> OTHER INFORMATION: Probe sequence for the 16S locus in Escherichia
      coli and Shigella

<400> SEQUENCE: 44
ttttctcctt tgctcattga cgttatttt                                             30

<210> SEQ ID NO 45
<211> LENGTH: 30
<212> TYPE: DNA
<213> ORGANISM: Artificial Sequence
<220> FEATURE:
<223> OTHER INFORMATION: Probe sequence for the 16S locus in Bacillus
      spp. Group 1

<400> SEQUENCE: 45
tttttcagtt gaataagctg gcactcttt                                             30

<210> SEQ ID NO 46
<211> LENGTH: 30
<212> TYPE: DNA
<213> ORGANISM: Artificial Sequence
<220> FEATURE:
<223> OTHER INFORMATION: Probe sequence for the 16S locus in Bacillus
      spp. Group 2

<400> SEQUENCE: 46 tttttttcaag taccgttcga atagttttt                                            30

<210> SEQ ID NO 47
<211> LENGTH: 36
<212> TYPE: DNA
<213> ORGANISM: Artificial Sequence
<220> FEATURE:
<223> OTHER INFORMATION: Probe sequence for the 16S locus in bile-
      tolerant gram negative bacteria with high sensitivity

<400> SEQUENCE: 47
tttttctatg cagtcatgct gtgtgtrtgt cttttt                                     36

<210> SEQ ID NO 48
<211> LENGTH: 34
<212> TYPE: DNA
<213> ORGANISM: Artificial Sequence
<220> FEATURE:
<223> OTHER INFORMATION: Probe sequence for the 16S locus in bile-
      tolerant gram negative bacteria with medium sensitivity

<400> SEQUENCE: 48
tttttctatg cagccatgct gtgtgtrttt tttt                                       34

<210> SEQ ID NO 49
<211> LENGTH: 34
<212> TYPE: DNA
<213> ORGANISM: Artificial Sequence
<220> FEATURE:
<223> OTHER INFORMATION: Probe sequence for the 16S locus in bile-
``` tolerant gram negative bacteria with low sensitivity

<400> SEQUENCE: 49
tttttctatg cagtcatgct gcgtgtrttt tttt                34

<210> SEQ ID NO 50
<211> LENGTH: 30
<212> TYPE: DNA
<213> ORGANISM: Artificial Sequence
<220> FEATURE:
<223> OTHER INFORMATION: Probe sequence for the 16S locus in
      Campylobacter spp.

<400> SEQUENCE: 50 tttttatga cacttttcgg agctctttt                30

<210> SEQ ID NO 51
<211> LENGTH: 34
<212> TYPE: DNA
<213> ORGANISM: Artificial Sequence
<220> FEATURE:
<223> OTHER INFORMATION: Probe sequence for the 16S locus in
      Chromobacterium spp.

<400> SEQUENCE: 51
ttttattttc ccgctggtta ataccctta tttt                34

<210> SEQ ID NO 52
<211> LENGTH: 30
<212> TYPE: DNA
<213> ORGANISM: Artificial Sequence
<220> FEATURE:
<223> OTHER INFORMATION: Probe sequence for the 16S locus in Citrobacter
      spp.

<400> SEQUENCE: 52
tttttccctt agccattgac gttatttttt                30

<210> SEQ ID NO 53
<211> LENGTH: 30
<212> TYPE: DNA
<213> ORGANISM: Artificial Sequence
<220> FEATURE:
<223> OTHER INFORMATION: Probe sequence for the 16S locus in Clostridium
      spp.

<400> SEQUENCE: 53
ttttctggam gataatgacg gtacagtttt                30

<210> SEQ ID NO 54
<211> LENGTH: 30
<212> TYPE: DNA
<213> ORGANISM: Artificial Sequence
<220> FEATURE:
<223> OTHER INFORMATION: Probe sequence for the 16S locus in Coliform
      and Enterobacteriaceae

<400> SEQUENCE: 54 tttttctat tgacgttacc cgcttttttt                30

<210> SEQ ID NO 55
<211> LENGTH: 30
<212> TYPE: DNA
<213> ORGANISM: Artificial Sequence
<220> FEATURE:
<223> OTHER INFORMATION: Probe sequence for the 16S locus in Aeromonas
      salmonicida Aeromonas hydrophilia

<400> SEQUENCE: 55
tttttgccta atacgtrtca actgcttttt                                    30

<210> SEQ ID NO 56
<211> LENGTH: 30
<212> TYPE: DNA
<213> ORGANISM: Artificial Sequence
<220> FEATURE:
<223> OTHER INFORMATION: Probe sequence for the 16S locus in Aeromonas
      spp.

<400> SEQUENCE: 56
ttattttctg tgacgttact cgcttttatt                                    30

<210> SEQ ID NO 57
<211> LENGTH: 30
<212> TYPE: DNA
<213> ORGANISM: Artificial Sequence
<220> FEATURE:
<223> OTHER INFORMATION: Probe sequence for the 16S locus in
      Alkanindiges spp.

<400> SEQUENCE: 57
tttttaggct actgrtacta atatctttt                                     30

<210> SEQ ID NO 58
<211> LENGTH: 34
<212> TYPE: DNA
<213> ORGANISM: Artificial Sequence
<220> FEATURE:
<223> OTHER INFORMATION: Probe sequence for the 16S locus in Bacillus
      pumilus

<400> SEQUENCE: 58
tttatttaag tgcragagta actgctattt tatt                               34

<210> SEQ ID NO 59
<211> LENGTH: 34
<212> TYPE: DNA
<213> ORGANISM: Artificial Sequence
<220> FEATURE:
<223> OTHER INFORMATION: Probe sequence for bacterial etuf gene

<400> SEQUENCE: 59 tttttccat caaagttggt gaagaatctt tttt                                34

<210> SEQ ID NO 60
<211> LENGTH: 30
<212> TYPE: DNA
<213> ORGANISM: Artificial Sequence
<220> FEATURE:
<223> OTHER INFORMATION: Probe sequence for the 16S locus in Hafnia spp.

<400> SEQUENCE: 60 tttttctaa ccgcagtgat tgatctttt                                      30

<210> SEQ ID NO 61
<211> LENGTH: 34
<212> TYPE: DNA
<213> ORGANISM: Artificial Sequence
<220> FEATURE:
<223> OTHER INFORMATION: Probe sequence for bacterial InvA gene

<400> SEQUENCE: 61
tttttttatt gatgccgatt tgaaggcctt tttt                               34

<210> SEQ ID NO 62
<211> LENGTH: 30
<212> TYPE: DNA
<213> ORGANISM: Artificial Sequence
<220> FEATURE:
<223> OTHER INFORMATION: Probe sequence for the 16S locus in Klebsiella
      oxytoca

<400> SEQUENCE: 62 tttttctaa ccttattcat tgatcttttt                                30

<210> SEQ ID NO 63
<211> LENGTH: 30
<212> TYPE: DNA
<213> ORGANISM: Artificial Sequence
<220> FEATURE:
<223> OTHER INFORMATION: Probe sequence for the 16S locus in Klebsiella
      pneumoniae

<400> SEQUENCE: 63 tttttctaa ccttggcgat tgatcttttt                                30

<210> SEQ ID NO 64
<211> LENGTH: 34
<212> TYPE: DNA
<213> ORGANISM: Artificial Sequence
<220> FEATURE:
<223> OTHER INFORMATION: Probe sequence for the 16S locus in Legionella
      spp.

<400> SEQUENCE: 64
tttattctga taggttaaga gctgatcttt attt                          34

<210> SEQ ID NO 65
<211> LENGTH: 30
<212> TYPE: DNA
<213> ORGANISM: Artificial Sequence
<220> FEATURE:
<223> OTHER INFORMATION: Probe sequence for the 16S locus in Listeria
      spp.

<400> SEQUENCE: 65
ttttctaagt actgttgtta gagaatttt                                30

<210> SEQ ID NO 66
<211> LENGTH: 30
<212> TYPE: DNA
<213> ORGANISM: Artificial Sequence
<220> FEATURE:
<223> OTHER INFORMATION: Probe sequence for the 16S locus in Panteoa
      agglomerans

<400> SEQUENCE: 66 tttttaacc ctgtcgattg acgccttttt                                30

<210> SEQ ID NO 67
<211> LENGTH: 30
<212> TYPE: DNA
<213> ORGANISM: Artificial Sequence
<220> FEATURE:
<223> OTHER INFORMATION: Probe sequence for the 16S locus in Panteoa
      stewartii

<400> SEQUENCE: 67 tttttaacc tcatcaattg acgccttttt                                30

<210> SEQ ID NO 68
<211> LENGTH: 30
<212> TYPE: DNA
<213> ORGANISM: Artificial Sequence
<220> FEATURE:
<223> OTHER INFORMATION: Probe sequence for the 16S locus in Pseudomonas aeruginosa

<400> SEQUENCE: 68
tttttgcagt aagttaatac cttgtctttt                                    30

<210> SEQ ID NO 69
<211> LENGTH: 30
<212> TYPE: DNA
<213> ORGANISM: Artificial Sequence
<220> FEATURE:
<223> OTHER INFORMATION: Probe sequence for the 16S locus in Pseudomonas cannabina

<400> SEQUENCE: 69
tttttttacg tatctgtttt gactctttt                                     30

<210> SEQ ID NO 70
<211> LENGTH: 30
<212> TYPE: DNA
<213> ORGANISM: Artificial Sequence
<220> FEATURE:
<223> OTHER INFORMATION: Probe sequence for the 16S locus in Pseudomonas spp.

<400> SEQUENCE: 70
tttttgttac cracagaata agcatttt   30

<210> SEQ ID NO 71
<211> LENGTH: 30
<212> TYPE: DNA
<213> ORGANISM: Artificial Sequence
<220> FEATURE:
<223> OTHER INFORMATION: Probe sequence for the 16S locus in Pseudomonas spp.

<400> SEQUENCE: 71 tttttaagc actttaagtt gggatttttt                                     30

<210> SEQ ID NO 72
<211> LENGTH: 34
<212> TYPE: DNA
<213> ORGANISM: Artificial Sequence
<220> FEATURE:
<223> OTHER INFORMATION: Probe sequence for the 16S locus in Pseudomonas spp.

<400> SEQUENCE: 72
tttattttaa gcactttaag ttgggatttt attt                               34

<210> SEQ ID NO 73
<211> LENGTH: 30
<212> TYPE: DNA
<213> ORGANISM: Artificial Sequence
<220> FEATURE:
<223> OTHER INFORMATION: Probe sequence for the 16S locus in Salmonella bongori

<400> SEQUENCE: 73
tttttttaat aaccttgttg attgttttt                                     30

<210> SEQ ID NO 74

<211> LENGTH: 30
<212> TYPE: DNA
<213> ORGANISM: Artificial Sequence
<220> FEATURE:
<223> OTHER INFORMATION: Probe sequence for the 16S locus in Salmonella
      enterica

<400> SEQUENCE: 74
tttttttgtt gtggttaata accgattttt                                30

<210> SEQ ID NO 75
<211> LENGTH: 30
<212> TYPE: DNA
<213> ORGANISM: Artificial Sequence
<220> FEATURE:
<223> OTHER INFORMATION: Probe sequence for the 16S locus in Salmonella
      enterica

<400> SEQUENCE: 75 ttttttaac cgcagcaatt gactcttttt                                 30

<210> SEQ ID NO 76
<211> LENGTH: 30
<212> TYPE: DNA
<213> ORGANISM: Artificial Sequence
<220> FEATURE:
<223> OTHER INFORMATION: Probe sequence for the 16S locus in Salmonella
      enterica

<400> SEQUENCE: 76 tttttctgt taataaccgc agctttttt                                  30

<210> SEQ ID NO 77
<211> LENGTH: 34
<212> TYPE: DNA
<213> ORGANISM: Artificial Sequence
<220> FEATURE:
<223> OTHER INFORMATION: Probe sequence for the 16S locus in Serratia
      spp.

<400> SEQUENCE: 77
tttattctgt gaacttaata cgttcatttt tatt                           34

<210> SEQ ID NO 78
<211> LENGTH: 34
<212> TYPE: DNA
<213> ORGANISM: Artificial Sequence
<220> FEATURE:
<223> OTHER INFORMATION: Probe sequence for the 16S locus in
      Staphylococcus aureus

<400> SEQUENCE: 78
tttattttca tatgtgtaag taactgtttt attt                           34

<210> SEQ ID NO 79
<211> LENGTH: 30
<212> TYPE: DNA
<213> ORGANISM: Artificial Sequence
<220> FEATURE:
<223> OTHER INFORMATION: Probe sequence for the 16S locus in
      Staphylococcus aureus

<400> SEQUENCE: 79 tttttcata tgtgtaagta actgttttt                                  30

<210> SEQ ID NO 80
<211> LENGTH: 34

```
<212> TYPE: DNA
<213> ORGANISM: Artificial Sequence
<220> FEATURE:
<223> OTHER INFORMATION: Probe sequence for the 16S locus in
      Streptomyces spp.

<400> SEQUENCE: 80
ttttatttta agaagcgaga gtgacttttta tttt                              34

<210> SEQ ID NO 81
<211> LENGTH: 30
<212> TYPE: DNA
<213> ORGANISM: Artificial Sequence
<220> FEATURE:
<223> OTHER INFORMATION: Probe sequence for bacterial stx1 gene

<400> SEQUENCE: 81
tttttctttt ccaggtacaa cagctttttt                                    30

<210> SEQ ID NO 82
<211> LENGTH: 30
<212> TYPE: DNA
<213> ORGANISM: Artificial Sequence
<220> FEATURE:
<223> OTHER INFORMATION: Probe sequence for bacterial stx2 gene

<400> SEQUENCE: 82 tttttgcac tgtctgaaac tgcctttttt                                     30

<210> SEQ ID NO 83
<211> LENGTH: 30
<212> TYPE: DNA
<213> ORGANISM: Artificial Sequence
<220> FEATURE:
<223> OTHER INFORMATION: Probe sequence for the 16S locus in Vibrio spp.

<400> SEQUENCE: 83 tttttgaag gtggttaagc taatttttt                                      30

<210> SEQ ID NO 84
<211> LENGTH: 30
<212> TYPE: DNA
<213> ORGANISM: Artificial Sequence
<220> FEATURE:
<223> OTHER INFORMATION: Probe sequence for the 16S locus in Xanthamonas
      spp.

<400> SEQUENCE: 84 tttttgtta atacccgatt gttctttttt                                     30

<210> SEQ ID NO 85
<211> LENGTH: 30
<212> TYPE: DNA
<213> ORGANISM: Artificial Sequence
<220> FEATURE:
<223> OTHER INFORMATION: Probe sequence for the 16S locus in Ysernia
      pestis

<400> SEQUENCE: 85 ttttttgag tttaatacgc tcaactttt                                      30

<210> SEQ ID NO 86
<211> LENGTH: 38
<212> TYPE: DNA
<213> ORGANISM: Artificial Sequence
<220> FEATURE:
<223> OTHER INFORMATION: Probe sequence for the ITS2 locus in total
```

-continued yeast and mold with high sensitivity

<400> SEQUENCE: 86 tttttttga atcatcgart ctttgaacgc atttttttt                    38

<210> SEQ ID NO 87
<211> LENGTH: 31
<212> TYPE: DNA
<213> ORGANISM: Artificial Sequence
<220> FEATURE:
<223> OTHER INFORMATION: Probe sequence for the ITS2 locus in total
      yeast and mold with low sensitivity

<400> SEQUENCE: 87
ttttttttga atcatcgart ctcctttttt t                           31

<210> SEQ ID NO 88
<211> LENGTH: 36
<212> TYPE: DNA
<213> ORGANISM: Artificial Sequence
<220> FEATURE:
<223> OTHER INFORMATION: Probe sequence for the ITS2 locus in total
      yeast and mold with medium sensitivity

<400> SEQUENCE: 88
ttttttttga atcatcgart ctttgaacgt tttttt                      36

<210> SEQ ID NO 89
<211> LENGTH: 34
<212> TYPE: DNA
<213> ORGANISM: Artificial Sequence
<220> FEATURE:
<223> OTHER INFORMATION: Probe sequence for the ITS2 locus in Alternaria
      spp.

<400> SEQUENCE: 89 tttttcaaa ggtctagcat ccattaagtt tttt                         34

<210> SEQ ID NO 90
<211> LENGTH: 34
<212> TYPE: DNA
<213> ORGANISM: Artificial Sequence
<220> FEATURE:
<223> OTHER INFORMATION: Probe sequence for the ITS2 locus in
      Aspergillus flavus

<400> SEQUENCE: 90 tttttcgca aatcaatctt tttccagtct tttt                         34

<210> SEQ ID NO 91
<211> LENGTH: 40
<212> TYPE: DNA
<213> ORGANISM: Artificial Sequence
<220> FEATURE:
<223> OTHER INFORMATION: Probe sequence for the ITS2 locus in
      Aspergillus flavus

<400> SEQUENCE: 91 ttttttctt gccgaacgca aatcaatctt tttttttt                     40

<210> SEQ ID NO 92
<211> LENGTH: 34
<212> TYPE: DNA
<213> ORGANISM: Artificial Sequence
<220> FEATURE:
<223> OTHER INFORMATION: Probe sequence for the ITS2 locus in
      Aspergillus fumigatus

<400> SEQUENCE: 92
tttcttttcg acacccaact ttatttcctt attt        34

<210> SEQ ID NO 93
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus fumigatus

<400> SEQUENCE: 93 ttttttgcc agccgacacc cattcttttt        30

<210> SEQ ID NO 94
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus nidulans

<400> SEQUENCE: 94 tttttggcg tctccaacct tacccttttt        30

<210> SEQ ID NO 95
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus niger

<400> SEQUENCE: 95 tttttcgac gttttccaac catttctttt        30

<210> SEQ ID NO 96
<211> LENGTH: 34
<212> TYPE: DNA
<213> ORGANISM: Artificial Sequence
<220> FEATURE:
<223> OTHER INFORMATION: Probe sequence for the ITS2 locus in
      Aspergillus niger

<400> SEQUENCE: 96
ttttttttcg acgttttcca accatttctt tttt        34

<210> SEQ ID NO 97
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus niger

<400> SEQUENCE: 97
tttttttcgc cgacgttttc caatttttt        30

<210> SEQ ID NO 98
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus terreus

<400> SEQUENCE: 98
tttttcgacg catttatttg caacccttttt                                    30

<210> SEQ ID NO 99
<211> LENGTH: 34
<212> TYPE: DNA
<213> ORGANISM: Artificial Sequence
<220> FEATURE:
<223> OTHER INFORMATION: Probe sequence for the ITS2 locus in Blumeria
      spp.

<400> SEQUENCE: 99
tttatttgcc aaaamtcctt aattgctctt tttt                                34

<210> SEQ ID NO 100
<211> LENGTH: 40
<212> TYPE: DNA
<213> ORGANISM: Artificial Sequence
<220> FEATURE:
<223> OTHER INFORMATION: Probe sequence for the ITS2 locus in Botrytis
      spp.

<400> SEQUENCE: 100
tttttttcat ctctcgttac aggttctcgg ttcttttttt                          40

<210> SEQ ID NO 101
<211> LENGTH: 34
<212> TYPE: DNA
<213> ORGANISM: Artificial Sequence
<220> FEATURE:
<223> OTHER INFORMATION: Probe sequence for the ITS2 locus in Candida
      albicans

<400> SEQUENCE: 101
tttttttttg aaagacggta gtggtaagtt tttt                                34

<210> SEQ ID NO 102
<211> LENGTH: 34
<212> TYPE: DNA
<213> ORGANISM: Artificial Sequence
<220> FEATURE:
<223> OTHER INFORMATION: Probe sequence for the ITS2 locus in Candida
      spp. Group 1

<400> SEQUENCE: 102
tttttttgtt tggtgttgag cratacgtat tttt                                34

<210> SEQ ID NO 103
<211> LENGTH: 35
<212> TYPE: DNA
<213> ORGANISM: Artificial Sequence
<220> FEATURE:
<223> OTHER INFORMATION: Probe sequence for the ITS2 locus in Candida
      spp. Group 2

<400> SEQUENCE: 103
ttttactgtt tggtaatgag tgatactctc atttt                               35

<210> SEQ ID NO 104
<211> LENGTH: 34
<212> TYPE: DNA
<213> ORGANISM: Artificial Sequence
<220> FEATURE:
<223> OTHER INFORMATION: Probe sequence for the ITS2 locus in Chaetomium
      spp.

<400> SEQUENCE: 104
tttcttttgg ttccggccgt taaaccattt tttt         34

<210> SEQ ID NO 105
<211> LENGTH: 34
<212> TYPE: DNA
<213> ORGANISM: Artificial Sequence
<220> FEATURE:
<223> OTHER INFORMATION: Probe sequence for the ITS2 locus in
      Cladosporium spp.

<400> SEQUENCE: 105 tttttttttgt ggaaactatt cgctaaagtt tttt         34

<210> SEQ ID NO 106
<211> LENGTH: 34
<212> TYPE: DNA
<213> ORGANISM: Artificial Sequence
<220> FEATURE:
<223> OTHER INFORMATION: Probe sequence for the ITS2 locus in
      Erysiphe spp.

<400> SEQUENCE: 106 tttctttta cgattctcgc gacagagttt tttt         34

<210> SEQ ID NO 107
<211> LENGTH: 34
<212> TYPE: DNA
<213> ORGANISM: Artificial Sequence
<220> FEATURE:
<223> OTHER INFORMATION: Probe sequence for the ITS2 locus in
      Fusarum oxysporum

<400> SEQUENCE: 107 ttttttttctc gttactggta atcgtcgttt tttt         34

<210> SEQ ID NO 108
<211> LENGTH: 34
<212> TYPE: DNA
<213> ORGANISM: Artificial Sequence
<220> FEATURE:
<223> OTHER INFORMATION: Probe sequence for the ITS2 locus in
      Fusarium spp.

<400> SEQUENCE: 108
ttttttttaa cacctcgcra ctggagattt tttt         34

<210> SEQ ID NO 109
<211> LENGTH: 34
<212> TYPE: DNA
<213> ORGANISM: Artificial Sequence
<220> FEATURE:
<223> OTHER INFORMATION: Probe sequence for the ITS2 locus in
      Golovinomyces spp.

<400> SEQUENCE: 109 tttttttccgc ttgccaatca atccatctct tttt         34

<210> SEQ ID NO 110
<211> LENGTH: 34
<212> TYPE: DNA
<213> ORGANISM: Artificial Sequence
<220> FEATURE:
<223> OTHER INFORMATION: Probe sequence for the ITS2 locus in
      Histoplasma capsulatum

<400> SEQUENCE: 110 tttattttttg tcgagttccg gtgcccttttt attt                                   34

<210> SEQ ID NO 111
<211> LENGTH: 34
<212> TYPE: DNA
<213> ORGANISM: Artificial Sequence
<220> FEATURE:
<223> OTHER INFORMATION: Probe sequence for the ITS2 locus in Isaria
      spp.

<400> SEQUENCE: 111 tttattttttc cgcggcgacc tctgctcttt attt                                   34

<210> SEQ ID NO 112
<211> LENGTH: 34
<212> TYPE: DNA
<213> ORGANISM: Artificial Sequence
<220> FEATURE:
<223> OTHER INFORMATION: Probe sequence for the ITS2 locus in
      Monocillium spp.

<400> SEQUENCE: 112
tttcttttga gcgacgacgg gcccaattttt cttt                                   34

<210> SEQ ID NO 113
<211> LENGTH: 30
<212> TYPE: DNA
<213> ORGANISM: Artificial Sequence
<220> FEATURE:
<223> OTHER INFORMATION: Probe sequence for the ITS2 locus in Mucor spp.

<400> SEQUENCE: 113
ttttctccaw tgagyacgcc tgtttctttt                                         30

<210> SEQ ID NO 114
<211> LENGTH: 34
<212> TYPE: DNA
<213> ORGANISM: Artificial Sequence
<220> FEATURE:
<223> OTHER INFORMATION: Probe sequence for the ITS2 locus in
      Myrothecium spp.

<400> SEQUENCE: 114
tttattttcg gtggccatgc cgttaaatttt tatt                                   34

<210> SEQ ID NO 115
<211> LENGTH: 34
<212> TYPE: DNA
<213> ORGANISM: Artificial Sequence
<220> FEATURE:
<223> OTHER INFORMATION: Probe sequence for the ITS2 locus in
      Oidiodendron spp.

<400> SEQUENCE: 115
tttttttgcg tagtacatct ctcgctcatt tttt                                    34

<210> SEQ ID NO 116
<211> LENGTH: 34
<212> TYPE: DNA
<213> ORGANISM: Artificial Sequence
<220> FEATURE:
<223> OTHER INFORMATION: Probe sequence for the ITS2 locus in
      Penicillium oxalicum

<400> SEQUENCE: 116 tttttttacac catcaatctt aaccaggcct tttt                                   34

<210> SEQ ID NO 117
<211> LENGTH: 34
<212> TYPE: DNA
<213> ORGANISM: Artificial Sequence
<220> FEATURE:
<223> OTHER INFORMATION: Probe sequence for the ITS2 locus in
      Penicillium paxilli

<400> SEQUENCE: 117
tttttccccc tcaatcttta accaggcctt tttt                                    34

<210> SEQ ID NO 118
<211> LENGTH: 34
<212> TYPE: DNA
<213> ORGANISM: Artificial Sequence
<220> FEATURE:
<223> OTHER INFORMATION: Probe sequence for the ITS2 locus in
      Penicillium spp.

<400> SEQUENCE: 118 tttttcaac ccaaatttt atccaggcct tttt                                     34

<210> SEQ ID NO 119
<211> LENGTH: 34
<212> TYPE: DNA
<213> ORGANISM: Artificial Sequence
<220> FEATURE:
<223> OTHER INFORMATION: Probe sequence for the ITS2 locus in
      Phoma/Epicoccum ssp.

<400> SEQUENCE: 119
tttttttgca gtacatctcg cgctttgatt tttt                                    34

<210> SEQ ID NO 120
<211> LENGTH: 34
<212> TYPE: DNA
<213> ORGANISM: Artificial Sequence
<220> FEATURE:
<223> OTHER INFORMATION: Probe sequence for the ITS2 locus in
      Podosphaera spp.

<400> SEQUENCE: 120 tttttgacc tgccaaaacc cacataccat tttt                                     34

<210> SEQ ID NO 121
<211> LENGTH: 34
<212> TYPE: DNA
<213> ORGANISM: Artificial Sequence
<220> FEATURE:
<223> OTHER INFORMATION: Probe sequence for the ITS2 locus in
      Podosphaera spp.

<400> SEQUENCE: 121
ttttttttag tcaygtatct cgcgacagtt tttt                                    34

<210> SEQ ID NO 122
<211> LENGTH: 34
<212> TYPE: DNA
<213> ORGANISM: Artificial Sequence
<220> FEATURE:
<223> OTHER INFORMATION: Probe sequence for the ITS2 locus in Phythium
      oligandrum

<400> SEQUENCE: 122
ttttatttaa aggagacaac accaattttt attt                                    34

```
<210> SEQ ID NO 123
<211> LENGTH: 34
<212> TYPE: DNA
<213> ORGANISM: Artificial Sequence
<220> FEATURE:
<223> OTHER INFORMATION: Probe sequence for the ITS2 locus in
      Rhodoturula spp.

<400> SEQUENCE: 123 tttttctcg ttcgtaatgc attagcactt tttt                              34

<210> SEQ ID NO 124
<211> LENGTH: 34
<212> TYPE: DNA
<213> ORGANISM: Artificial Sequence
<220> FEATURE:
<223> OTHER INFORMATION: Probe sequence for the ITS2 locus in
      Stachybotrys spp.

<400> SEQUENCE: 124
tttcttctgc atcggagctc agcgcgtttt attt                             34

<210> SEQ ID NO 125
<211> LENGTH: 34
<212> TYPE: DNA
<213> ORGANISM: Artificial Sequence
<220> FEATURE:
<223> OTHER INFORMATION: Probe sequence for the ITS2 locus in
      Trichoderma spp.

<400> SEQUENCE: 125
tttttcctcc tgcgcagtag tttgcacatc tttt                             34

<210> SEQ ID NO 126
<211> LENGTH: 34
<212> TYPE: DNA
<213> ORGANISM: Artificial Sequence
<220> FEATURE:
<223> OTHER INFORMATION: Probe sequence for ITS1 locus in Cannabis
      species

<400> SEQUENCE: 126 tttttaatc tgcgccaagg aacaatattt tttt                              34

<210> SEQ ID NO 127
<211> LENGTH: 34
<212> TYPE: DNA
<213> ORGANISM: Artificial Sequence
<220> FEATURE:
<223> OTHER INFORMATION: Probe sequence for ITS1 locus in Cannabis
      species

<400> SEQUENCE: 127
tttttgcaat ctgcgccaag gaacaatatt tttt                             34

<210> SEQ ID NO 128
<211> LENGTH: 34
<212> TYPE: DNA
<213> ORGANISM: Artificial Sequence
<220> FEATURE:
<223> OTHER INFORMATION: Probe sequence for ITS1 locus in Cannabis
      species

<400> SEQUENCE: 128
tttatttctt gcgccaagga acaatatttt attt                             34

<210> SEQ ID NO 129
```

```
<211> LENGTH: 32
<212> TYPE: DNA
<213> ORGANISM: Artificial Sequence
<220> FEATURE:
<223> OTHER INFORMATION: Probe sequence for image calibration with high
      sensitivity

<400> SEQUENCE: 129
ttttctatgt atcgatgttg agaaattttt tt                                    32

<210> SEQ ID NO 130
<211> LENGTH: 32
<212> TYPE: DNA
<213> ORGANISM: Artificial Sequence
<220> FEATURE:
<223> OTHER INFORMATION: Probe sequence for image calibration with low
      sensitivity

<400> SEQUENCE: 130
ttttctagat acttgtgtaa gtgaattttt tt                                    32

<210> SEQ ID NO 131
<211> LENGTH: 32
<212> TYPE: DNA
<213> ORGANISM: Artificial Sequence
<220> FEATURE:
<223> OTHER INFORMATION: Probe sequence for image calibration with
      medium sensitivity

<400> SEQUENCE: 131
ttttctaagt catgttgttg aagaatttttt tt                                   32

<210> SEQ ID NO 132
<211> LENGTH: 34
<212> TYPE: DNA
<213> ORGANISM: Artificial Sequence
<220> FEATURE:
<223> OTHER INFORMATION: Probe sequence for negative control

<400> SEQUENCE: 132 tttttctac tacctatgct gattcactct tttt                                   34

<210> SEQ ID NO 133
<211> LENGTH: 24
<212> TYPE: DNA
<213> ORGANISM: Artificial Sequence
<220> FEATURE:
<223> OTHER INFORMATION: Forward universal preamplification primer for
      fungus and bacteria

<400> SEQUENCE: 133
ttcagcctct gtacgtgctt catg                                             24

<210> SEQ ID NO 134
<211> LENGTH: 24
<212> TYPE: DNA
<213> ORGANISM: Artificial Sequence
<220> FEATURE:
<223> OTHER INFORMATION: Reverse universal preamplification primer for
      fungus and bacteria

<400> SEQUENCE: 134
ttcagcctct gatcgtgctt ctag                                             24

<210> SEQ ID NO 135
<211> LENGTH: 26
<212> TYPE: DNA
```

```
<213> ORGANISM: Artificial Sequence
<220> FEATURE:
<223> OTHER INFORMATION: Forward RSG Primer for amplification all fungus

<400> SEQUENCE: 135
tttactttca acaayggatc tcttgg                                          26

<210> SEQ ID NO 136
<211> LENGTH: 23
<212> TYPE: DNA
<213> ORGANISM: Artificial Sequence
<220> FEATURE:
<223> OTHER INFORMATION: Reverse RSG Primer for amplification of all
      fungus

<400> SEQUENCE: 136
cttttcctcc gcttattgat atg                                             23

<210> SEQ ID NO 137
<211> LENGTH: 23
<212> TYPE: DNA
<213> ORGANISM: Artificial Sequence
<220> FEATURE:
<223> OTHER INFORMATION: Forward RSG Primer for amplification of all
      bacteria

<400> SEQUENCE: 137
tttcacactg gractgagac acg                                             23

<210> SEQ ID NO 138
<211> LENGTH: 24
<212> TYPE: DNA
<213> ORGANISM: Artificial Sequence
<220> FEATURE:
<223> OTHER INFORMATION: Reverse RSG Primer for amplification of all
      bacteria

<400> SEQUENCE: 138
ttttgtatta ccgcggctgc tggc                                            24

<210> SEQ ID NO 139
<211> LENGTH: 23
<212> TYPE: DNA
<213> ORGANISM: Artificial Sequence
<220> FEATURE:
<223> OTHER INFORMATION: Forward Primer for amplification of all fungus

<400> SEQUENCE: 139
tttgcatcga tgaagaacgc agc                                             23

<210> SEQ ID NO 140
<211> LENGTH: 23
<212> TYPE: DNA
<213> ORGANISM: Artificial Sequence
<220> FEATURE:
<223> OTHER INFORMATION: Reverse Primer for amplification of all fungus

<400> SEQUENCE: 140
ttttcctccg cttattgata tgc                                             23

<210> SEQ ID NO 141
<211> LENGTH: 24
<212> TYPE: DNA
<213> ORGANISM: Artificial Sequence
<220> FEATURE:
<223> OTHER INFORMATION: Forward Primer for amplification of all
      bacteria
```

```
<400> SEQUENCE: 141
tttcacactg gractgagac acgg                                              24

<210> SEQ ID NO 142
<211> LENGTH: 30
<212> TYPE: DNA
<213> ORGANISM: Artificial Sequence
<220> FEATURE:
<223> OTHER INFORMATION: Internal reference probe sequence for total
      aerobic bacteria

<400> SEQUENCE: 142
tttttttttc catcgggagc gagttttttt                                        30

<210> SEQ ID NO 143
<211> LENGTH: 36
<212> TYPE: DNA
<213> ORGANISM: Artificial Sequence
<220> FEATURE:
<223> OTHER INFORMATION: Internal reference probe sequence for bile-
      tolerant gram-negative bacteria

<400> SEQUENCE: 143
tttttctatg tattcctgat gtagatrtgt cttttt                                 36

<210> SEQ ID NO 144
<211> LENGTH: 30
<212> TYPE: DNA
<213> ORGANISM: Artificial Sequence
<220> FEATURE:
<223> OTHER INFORMATION: Internal reference probe sequence for
      Enterobacteriaceae and Coliform bacteria

<400> SEQUENCE: 144 tttttctct tgagcttacc ccgttttttt                                         30

<210> SEQ ID NO 145
<211> LENGTH: 38
<212> TYPE: DNA
<213> ORGANISM: Artificial Sequence
<220> FEATURE:
<223> OTHER INFORMATION: Internal reference probe sequence for total
      yeast and mold

<400> SEQUENCE: 145
ttttttttgc atcatagaaa ctttgtacgc atttttt                                38

<210> SEQ ID NO 146
<211> LENGTH: 34
<212> TYPE: DNA
<213> ORGANISM: Artificial Sequence
<220> FEATURE:
<223> OTHER INFORMATION: Probe sequence for Golovinomyces spp.

<400> SEQUENCE: 146
tttatttaat caatccatca tctcaagtct tttt                                   34

<210> SEQ ID NO 147
<211> LENGTH: 34
<212> TYPE: DNA
<213> ORGANISM: Artificial Sequence
<220> FEATURE:
<223> OTHER INFORMATION: Probe sequence for Listeria spp.

<400> SEQUENCE: 147
``` tttatttttga taagagtaac tgcttgcttt attt         34

<210> SEQ ID NO 148
<211> LENGTH: 40
<212> TYPE: DNA
<213> ORGANISM: Artificial Sequence
<220> FEATURE:
<223> OTHER INFORMATION: Probe sequence for Mucor spp.

<400> SEQUENCE: 148 tttttttctcc awtgagyacg cctgtttcag tatctttttt         40

<210> SEQ ID NO 149
<211> LENGTH: 34
<212> TYPE: DNA
<213> ORGANISM: Artificial Sequence
<220> FEATURE:
<223> OTHER INFORMATION: Probe sequence for Saccharomyces spp.

<400> SEQUENCE: 149
tttatcttag gcgaacaatg ttcttaaatc tttt         34

<210> SEQ ID NO 150
<211> LENGTH: 34
<212> TYPE: DNA
<213> ORGANISM: Artificial Sequence
<220> FEATURE:
<223> OTHER INFORMATION: Probe sequence for Aspergillus terreus

<400> SEQUENCE: 150 tttttttacgc atttatttgc aacttgcctt tttt         34

<210> SEQ ID NO 151
<211> LENGTH: 30
<212> TYPE: DNA
<213> ORGANISM: Artificial Sequence
<220> FEATURE:
<223> OTHER INFORMATION: Probe sequence for Podosphaera spp.

<400> SEQUENCE: 151
tttttcgtcc cctaaacata gtggcttttt         30

<210> SEQ ID NO 152
<211> LENGTH: 440
<212> TYPE: DNA
<213> ORGANISM: Artificial Sequence
<220> FEATURE:
<223> OTHER INFORMATION: Consensus sequence of ITS2 domain in eukaryotes
<220> FEATURE:
<221> NAME/KEY: misc_feature
<222> LOCATION: 1..37, 86..120, 146..379, 403..440
<223> OTHER INFORMATION: n is any of a, c, t, or g

<400> SEQUENCE: 152
nnnnnnnnnn nnnnnnnnnn nnnnnnnnnn nnnnnnnact tycaacaayg         50
gatctcttgg ttctggcatc gatgaagaac gcagcnnnnn nnnnnnnnnn         100
nnnnnnnnnn nnnnnnnnnn gtgaatcatc gartctttga acgcannnnn         150
nnnnnnnnnn nnnnnnnnnn nnnnnnnnnn nnnnnnnnnn nnnnnnnnnn         200
nnnnnnnnnn nnnnnnnnnn nnnnnnnnnn nnnnnnnnnn nnnnnnnnnn         250
nnnnnnnnnn nnnnnnnnnn nnnnnnnnnn nnnnnnnnnn nnnnnnnnnn         300
nnnnnnnnnn nnnnnnnnnn nnnnnnnnnn nnnnnnnnnn nnnnnnnnnn         350
nnnnnnnnnn nnnnnnnnnn nnnnnnnnng catatcaata agcggaggaa         400

```
aannnnnnnn nnnnnnnnnn nnnnnnnnnn nnnnnnnnnn                            440
```

<210> SEQ ID NO 153
<211> LENGTH: 333
<212> TYPE: DNA
<213> ORGANISM: Artificial Sequence
<220> FEATURE:
<223> OTHER INFORMATION: Consensus sequence of rDNA domain in
      prokaryotes
<220> FEATURE:
<221> NAME/KEY: misc_feature
<222> LOCATION: 1..37, 59..64, 85..114, 137..203, 218..241, 263..333
<223> OTHER INFORMATION: n is any of a, c, t, or g

<400> SEQUENCE: 153

```
nnnnnnnnnn nnnnnnnnnn nnnnnnnnnn nnnnnncac aytggractg                  50 agacacggnn nnnnctccta cgggaggcag cagtnnnnnn nnnnnnnnnn                 100
nnnnnnnnnn nnnnayssag cmaygccgcg tgdrbgnnnn nnnnnnnnnn                 150
nnnnnnnnnn nnnnnnnnnn nnnnnnnnnn nnnnnnnnnn nnnnnnnnnn                 200
nnnattgacg ttacccgcnn nnnnnnnnnn nnnnnnnnnn ntgccagcag                 250
ccgcggtaat acnnnnnnnn nnnnnnnnnn nnnnnnnnnn nnnnnnnnnn                 300
nnnnnnnnnn nnnnnnnnnn nnnnnnnnnn nnn                                   333
```

<210> SEQ ID NO 154
<211> LENGTH: 439
<212> TYPE: DNA
<213> ORGANISM: Artificial Sequence
<220> FEATURE:
<223> OTHER INFORMATION: Internal reference sequence for use with the
      ITS2 domain in eukaryotes

<400> SEQUENCE: 154

```
tactattcag cctctgtacg tgcttcatgt aaattgaact ttcaacaacg                  50
gatctcttgg ttctggcatc gatgaagaac gcagcgactt gcgataagta                 100
atgtgaattg cagaattcag tgcatcatag aaactatgta cgcaaattgc                 150
gccccttggt attccggggg gcatgcctgt tcgagcgtca tttcaaccct                 200
caagcttagc ttggtattga gtctatgtca gtaatggcag gctctaaaat                 250
cagtggcggc gccgctgggt cctgaacgta gtaatatttc ttgtcaccgt                 300
ttctaggtgt gcttctgtct atacccaaat tcttctatgg ttgacctcgg                 350
atcaggtagg gataccgct gaacttaagc atatcaataa gcggaggaaa                  400
agcacgccgt ctagaagcac gatcagaggc tgaatacta                             439
```

<210> SEQ ID NO 155
<211> LENGTH: 333
<212> TYPE: DNA
<213> ORGANISM: Artificial Sequence
<220> FEATURE:
<223> OTHER INFORMATION: Internal reference sequence for use with the
      rDNA domain in prokaryotes

<400> SEQUENCE: 155

```
tactattcag cctctgtacg tgcttcatgt aaattgacac actggaactg                  50
agacacggtc cagactccat cgggagcgag catgggggaa tattgcacaa                 100
tgggcgcaag cctgatggac cctagccgcc actatgaaga aggccttcgg                 150
gttgtaaagt actttcagcg gggaggaggg aatgaaagta tatacctttc                 200
```

```
gtcatgtacg ttactcgcag aagaagcacc ggctaactcc gtgccagcag          250
ccgcggtaat acggagggtg caagcgttaa tcggaattac tgggcgcacg          300
ccgtctagaa gcacgatcag aggctgaata cta                            333

<210> SEQ ID NO 156
<211> LENGTH: 333
<212> TYPE: DNA
<213> ORGANISM: Artificial Sequence
<220> FEATURE:
<223> OTHER INFORMATION: Internal reference sequence for use with the
      rDNA domain in prokaryotes.

<400> SEQUENCE: 156
tactattcag cctctgtacg tgcttcatgt aaattgacac actggaactg           50
agacacggtc cagactcctg caggagacgg cagtggggaa tattgcacaa          100
tgggcgcaag cctgatgtat ccctgacgca gatatgaaga aggccttcgg          150
gttgtaaagt actttcagcg gggaggaagg tcgtaaaact aatacacttg          200
ctgtttgaac ttacccagag aagaagcacc ggctaactcc gtgccagcag          250
ccgcggtaat acggagggtg caagcgttaa tcggaattac tgggcgcacg          300
ccgtctagaa gcacgatcag aggctgaata cta                            333

<210> SEQ ID NO 157
<211> LENGTH: 333
<212> TYPE: DNA
<213> ORGANISM: Artificial Sequence
<220> FEATURE:
<223> OTHER INFORMATION: Internal reference sequence for use with the
      rDNA domain in prokaryotes

<400> SEQUENCE: 157
tactattcag cctctgtacg tgcttcatgt aaattgacac actggaactg           50
agacacggtc cagactccta gcggagcgag cagtggggaa tattgcacaa          100
tgggcgcaag cctgatgacg ccagtccgct ggtatgaaga aggccttcgg          150
gttgtaaagt actttcagcg gggaggaagg aggtaaatgt aatactcttg          200
ctacttgagc ttaccccgag aagaagcacc ggctaactcc gtgccagcag          250
ccgcggtaat acggagggtg caagcgttaa tcggaattac tgggcgcacg          300
ccgtctagaa gcacgatcag aggctgaata cta                            333
```

MICROARRAY BASED MULTIPLEX PATHOGEN ANALYSIS AND USES THEREOF

CROSS-REFERENCE TO RELATED APPLICATIONS

This application is a divisional under 35 U.S.C. § 120 of pending application U.S. Ser. No. 16/158,276, filed Oct. 11, 2018, which is a continuation-in-part under 35 U.S.C. § 120 of pending application U.S. Ser. No. 15/916,036, filed Mar. 8, 2018, which is a continuation-In-part under 35 U.S.C. § 120 of pending non-provisional application U.S. Ser. No. 15/388,561, filed Dec. 22, 2016, which claims benefit of priority under 35 U.S.C. § 119(e) of provisional application U.S. Ser. No. 62/271,371, filed Dec. 28, 2015, all of which are hereby incorporated in their entireties.

BACKGROUND OF THE INVENTION

Field of the Invention

The present disclosure is in the technical field of DNA based pathogen and plant analysis. More particularly, the present disclosure is in the technical field of pathogen analysis for plant, agriculture, food and water material using a multiplex assay and a 3-dimensional lattice microarray technology for immobilizing nucleic acid probes.

Description of the Related Art

Current techniques used to identify microbial pathogens rely upon established clinical microbiology monitoring. Pathogen identification is conducted using standard culture and susceptibility tests. These tests require a substantial investment of time, effort, cost as well as labile products. Current techniques are not ideal for testing large numbers samples. Culture-based testing is fraught with inaccuracies which include both false positives and false negatives, as well as unreliable quantification of colony forming units (CFUs). There are issues with the presence of viable but non-culturable microorganisms which do not show up using conventional culture methods. Certain culture tests are non-specific in terms of detecting both harmful and harmless species which diminishes the utility of the test to determine if there is a threat present in the sample being tested.

In response to challenges including false positives and culturing of microorganisms, DNA-based diagnostic methods such as polymerase chain reaction (PCR) amplification techniques were developed. To analyze a pathogen using PCR, DNA is extracted from a material prior to analysis, which is a time-consuming and costly step.

In an attempt to eliminate the pre-analysis extraction step of PCR, Colony PCR was developed. Using cells directly from colonies from plates or liquid cultures, Colony PCR allows PCR of bacterial cells without sample preparation. This technique was a partial success but was not as sensitive as culture indicating a possible issue with interference of the PCR by constituents in the specimens. Although this possible interference may not be significant enough to invalidate the utility of the testing performed, such interference can be significant for highly sensitive detection of pathogens for certain types of tests. Consequently, Colony PCR did not eliminate the pre-analysis extraction step for use of PCR, especially for highly sensitive detection of pathogens.

It is known that 16s DNA in bacteria and the internal transcribed spacer 2 (ITS2) locus in yeast or mold DNA can be PCR amplified, and once amplified can be analyzed to provide information about the specific bacteria or specific mold or yeast contamination in or on plant material. Further, for certain samples such as blood, fecal matter and others, PCR may be performed on the DNA in such samples absent any extraction of the DNA. However, for blood it is known that the result of such direct PCR is prone to substantial sample to sample variation due to inhibition by blood analytes. Additionally, attempts to perform direct PCR analysis on plant matter have generally been unsuccessful, due to heavy inhibition of PCR by plant constituents.

Over time, additional methods and techniques were developed to improve on the challenges of timely and specific detection and identification of pathogens. Immuno-assay techniques provide specific analysis. However, the technique is costly in the use of chemical consumables and has a long response time. Optical sensor technologies produce fast real-time detection but such sensor lack identification specificity as they offer a generic detection capability as the pathogen is usually optically similar to its benign background. Quantitative Polymerase Chain Reaction (qPCR) technique is capable of amplification and detection of a DNA sample in less than an hour. However, qPCR is largely limited to the analysis of a single pathogen. Consequently, if many pathogens are to be analyzed concurrently, as is the case with plant, agriculture, food and water material, a relatively large number of individual tests are performed in parallel.

Biological microarrays have become a key mechanism in a wide range of tools used to detect and analyze DNA. Microarray-based detection combines DNA amplification with the broad screening capability of microarray technology. This results in a specific detection and improved rate of process. DNA microarrays can be fabricated with the capacity to interrogate, by hybridization, certain segments of the DNA in bacteria and eukaryotic cells such as yeast and mold. However, processing a large number of PCR reactions for downstream microarray applications is costly and requires highly skilled individuals with complex organizational support. Because of these challenges, microarray techniques have not led to the development of downstream applications.

It is well known that DNA may be linked to a solid support for the purposes of DNA analysis. In those instances, the surface-associated DNA is generally referred to as the "Oligonucleotide probe" (nucleic acid probe, DNA probe) and its cognate partner to which the probe is designed to bind is referred to as the Hybridization Target (DNA Target). In such a device, detection and-or quantitation of the DNA Target is obtained by observing the binding of the Target to the surface bound Probe via duplex formation, a process also called "DNA Hybridization" (Hybridization).

Nucleic acid probe linkage to the solid support may be achieved by non-covalent adsorption of the DNA directly to a surface as occurs when a nucleic acid probe adsorbs to a neutral surface such as cellulose or when a nucleic acid probe adsorbs to cationic surface such as amino-silane coated glass or plastic. Direct, non-covalent adsorption of nucleic acid probes to the support has several limitations. The nucleic acid probe is necessarily placed in direct physical contact with the surface thereby presenting steric constraints to its binding to a DNA Target as the desired (bound) Target-Probe complex is a double helix which can only form by wrapping of the Target DNA strand about the bound Probe DNA: an interaction which is fundamentally inhibited by direct physical adsorption of the nucleic acid probe upon the underlying surface.

Nucleic acid probe linkage may also occur via covalent attachment of the nucleic acid probe to a surface. This can be induced by introduction of a reactive group (such as a primary amine) into the Probe then covalent attachment of the Probe, through the amine, to an amine-reactive moiety placed upon the surface: such as an epoxy group, or an isocyanate group, to form a secondary amine or a urea linkage, respectively. Since DNA is not generally reactive with epoxides or isocyanates or other similar standard nucleophilic substitutions, the DNA Probe must be first chemically modified with "unnatural" ligands such as primary amines or thiols. While such chemistry may be readily implemented during oligonucleotide synthesis, it raises the cost of the DNA Probe by more than a factor of two, due to the cost associated with the modification chemistry. A related UV crosslinking based approach circumvents the need for unnatural base chemistry, wherein Probe DNA can be linked to the surface via direct UV crosslinking of the DNA, mediated by photochemical addition of thymine within the Probe DNA to the amine surface to form a secondary amine adduct. However, the need for high energy UV for efficient crosslinking results in substantial side reactions that can damage the nucleic acid probe beyond use. As is the case for adsorptive linkage, the covalent linkages possible between a modified nucleic acid probe and a reactive surface are short, in the order of less than 10 rotatable bonds, thereby placing the nucleic acid probe within 2 nm of the underlying surface. Given that a standard nucleic acid probe is >20 bases in length (>10 nm long) a Probe/linker length ratio >10/1 also provides for destabilizing inhibition of the subsequent formation of the desired Target-Probe Duplex.

Previous Attempts at addressing these problems have not met with success. Attachment of nucleic acid probes to surfaces via their entrapment into a 3-Dimensional gel phase such as that created by polymerizing acrylamide and polysaccharides among others have been problematic due to the dense nature of the gel phases. While the pore size (about 10 nm) in these gels permit entrapment and/or attachment of the nucleic acid probes within the gel, the solution-phase DNA Target, which is typically many times longer than the nucleic acid probe, is blocked from penetrating the gel matrix thereby limiting use of these gel phase systems due to poor solution-phase access to the Target DNA. Furthermore Thus, the prior art is deficient in systems and methods for detecting and identifying pathogen DNA, which uses fewer chemical and labile products, reduces processing steps and provides faster results while maintaining accuracy, specificity and reliability. The prior art is also deficient in methods to determine absolute copy numbers of pathogen-specific DNA in an unpurified nucleic acid sample comprising a multiplicity of pathogens. The present invention fulfills this long-standing need and desire in the art.

SUMMARY OF THE INVENTION

The present invention is directed to a method for determining the absolute copy number of DNA for one or more pathogens in a plant tissue sample. The method comprises adding a known copy number of a synthetic DNA as an internal reference standard to an unpurified sample comprising plant DNA and non-DNA nucleic acids. The synthetic DNA has a central region sequence that is distinct from signature sequence determinants in the pathogen DNA and 5' and 3' end sequences substantially identical to a consensus sequence in the pathogen DNA. A tandem, single assay first amplification (locus PCR) of both pathogen DNA and the synthetic DNA is performed, followed by a second amplification (labeling PCR) using the first amplification products as template and fluorescent labeled primers to generate fluorescent labeled pathogen-specific and synthetic DNA-specific amplicons. These fluorescent labeled amplicons are hybridized with pathogen DNA and synthetic DNA specific nucleic acid probes immobilized at known positions on a 3-dimensional lattice microarray via different fluorescent labeled bifunctional polymer linkers. A multi-color image of the microarray is obtained, the fluorescent signals superimposed and the sequence of nucleic acid probes at superimposed positions compared with a database of signature sequence determinants in pathogens to identify the pathogen. The fluorescent intensities of the hybridized pathogen-specific amplicons is correlated with that of the synthetic DNA-specific amplicons and the known copy number of synthetic DNA added to the sample to determine copy number of the pathogen of interest in the sample.

The present invention is also directed to a method for determining the absolute copy number of DNA for one or more pathogens and plants in a plant tissue sample. The method comprises adding a known copy number of a synthetic DNA as an internal reference standard to an unpurified sample comprising plant DNA and non-DNA nucleic acids. The synthetic DNA has a central region sequence that is distinct from signature sequence determinants in the pathogen DNA and 5' and 3' end sequences substantially identical to a consensus sequence in the pathogen DNA and plant DNA. A tandem, single assay first amplification (locus PCR) of the pathogen DNA, plant DNA and synthetic DNA is performed, followed by a second amplification (labeling PCR) using the first amplification products as template and fluorescent labeled primers to generate fluorescent labeled pathogen-specific, plant-specific and synthetic DNA-specific amplicons. These fluorescent labeled amplicons are hybridized with pathogen DNA, plant DNA and synthetic DNA specific nucleic acid probes immobilized at known positions on a 3-dimensional lattice microarray via different fluorescent labeled bifunctional polymer linkers. A multi-color image of the microarray is obtained, the fluorescent signals superimposed and the sequence of nucleic acid probes at superimposed positions compared with a database of signature sequence determinants in pathogens and plants to identify the pathogen and plant respectively. The fluorescent intensities of the hybridized pathogen-specific amplicons and plant-specific amplicons is correlated with that of the synthetic DNA-specific amplicons and the known copy number of synthetic DNA added to the sample to determine copy number of the pathogen and plant in the sample.

BRIEF DESCRIPTION OF THE DRAWINGS

These and other features, aspects, and advantages of the embodiments of the present disclosure will become better understood when the following detailed description is read with reference to the accompanying drawings in which like characters represent like parts throughout the drawing, wherein:

FIG. 1A shows the components—unmodified nucleic acid probe, amine-functionalized (NH) bifunctional polymer linker and amine-functionalized (NH) fluorescently labeled bifunctional polymer linker in a solvent comprising water and a high boiling point water-miscible liquid, and a solid support with chemically activatable groups (X). FIG. 1B shows the first step reaction of the bifunctional polymer linker with the chemically activated solid support where the bifunctional polymer linker becomes covalently attached by the amine groups to the chemically activated groups on the solid support. FIG. 1C shows the second step of concentration via evaporation of water from the solvent to increase the concentration of the reactants—nucleic acid probes and bifunctional polymer linker. FIG. 1D shows the third step of UV crosslinking of the nucleic acid probes via thymidine base to the bifunctional polymer linker within evaporated surface, which in some instances also serves to covalently link adjacent bifunctional polymeric linkers together via crosslinking to the nucleic acid Probe.

FIG. 2A shows the components; unmodified nucleic acid probe and functionalized ($R_n$) bifunctional polymer linker and similarly functionalized fluorescent labeled bifunctional polymer linker in a solvent comprising water and a high boiling point water-miscible liquid, and a solid support, wherein the $R_n$ group is compatible for adsorbing to the solid support surface. FIG. 2B shows the first step adsorption of the bifunctional polymer linker on the solid support where the bifunctional polymer linkers become non-covalently attached by the $R_n$ groups to the solid support. FIG. 2C shows the second step of concentration via evaporation of water from the solvent to increase the concentration of the reactants—Nucleic acid probes and bifunctional polymer linker. FIG. 2D shows the third step of UV crosslinking of the nucleic acid probes via thymidine base to the bifunctional polymer linker and other nucleic acid probes within the evaporated surface which in some instances also serves to covalently link adjacent bifunctional polymeric linkers together via crosslinking to the nucleic acid Probe.

FIG. 3A shows an imaged microarray after hybridization and washing, as visualized at 635 nm. The 635 nm image is derived from signals from the (red) CY5 fluor attached to the 5' terminus of the bifunctional polymer linker (OligodT) which had been introduced during microarray fabrication as a positional marker in each microarray spot.

FIG. 3B shows a microarray imaged after hybridization and washing as visualized at 532 nm. The 532 nm image is derived from signals from the (green) CY3 fluor attached to the 5' terminus of PCR amplified DNA obtained during PCR Reaction #2 of a DNA containing sample.

FIG. 3C shows an imaged microarray after hybridization and washing as visualized with both the 532 nm and 635 nm images superimposed. The superimposed images display the utility of parallel attachment of a CY5-labelled OligodT positional marker relative to the sequence specific binding of the CY3-labelled PCR product.

FIG. 13 shows representative microarray hybridization data obtained from a representative raw *Cannabis* wash sample compared to a representative (raw) highly characterized, *candida* samples. In each case, the raw pathogen complement of each sample is PCR amplified, then hybridized on the microarray via the microarray probes described above. The data show that in this microarray format, specific fungal contaminants can be specifically identified via room temperature hybridization and washing on either raw *Cannabis* wash or cloned fungal sample.

DETAILED DESCRIPTION OF THE INVENTION

Figure 1A:
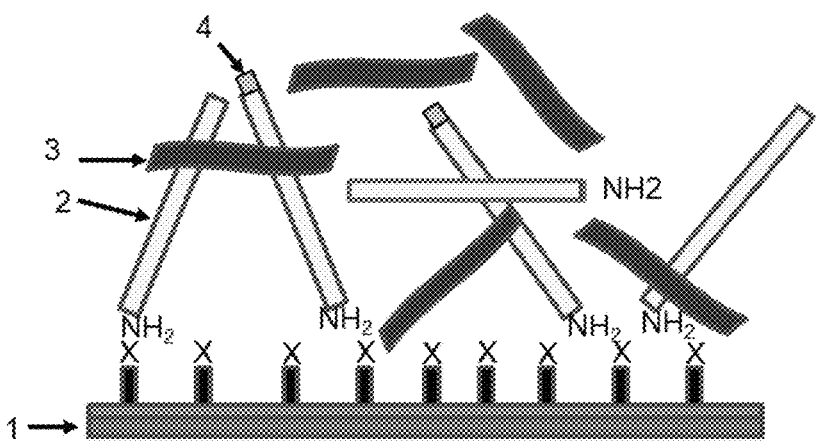
FIGS. 1A-1D illustrate a covalent microarray system comprising probes and bifunctional labels printed on an activated surface.

In one embodiment of this invention, there is provided a 3-dimensional lattice microarray system for screening a sample for the presence of a multiplicity of DNA. The system comprises a chemically activatable solid support, a bifunctional polymer linker and a plurality of nucleic acid probes designed to identify sequence determinants in plant, animal or pathogen DNA.

In this embodiment, the solid support may be made of any suitable material known in the art including but not limited to borosilicate glass, a thermoplastic acrylic resin such as poly(methylmethacrylate-VSUVT (PMMA-VSUVT), a cycloolefin polymers such as ZEONOR® 1060R, metals including, but not limited to gold and platinum, plastics including, but not limited to polyethylene terephthalate, polycarbonate, nylon, ceramics including, but not limited to $TiO_2$, and Indium tin oxide (ITO) and engineered carbon surfaces including, but not limited to graphene. The solid support has a front surface and a back surface and may be activated on the front surface with suitable chemicals which include but are not limited to epoxysilane, isocyanate, succinimide, carbodiimide, aldehyde and maleimide. These are well known in the art and one of ordinary skill in this art would be able to readily functionalize any of these supports as desired. In a preferred embodiment, the solid support is epoxysilane functionalized borosilicate glass support.

In this embodiment, the bifunctional polymer linker has a top domain and a bottom end. On the bottom end is attached a first reactive moiety that allows covalent attachment to the chemically activatable groups in the solid support. Examples of first reactive moieties include but are not limited to an amine group, a thiol group and an aldehyde group. Preferably, the first reactive moiety is an amine group. On the top domain of the bifunctional polymer linker is provided a second reactive moiety that allows covalent attachment to the oligonucleotide probe. Examples of second reactive moieties include but are not limited to nucleotide bases like thymidine, adenine, guanine, cytidine, uracil and bromodeoxyuridine and amino acid like cysteine, phenylalanine, tyrosine glycine, serine, tryptophan, cystine, methionine, histidine, arginine and lysine. The bifunctional polymer linker may be an oligonucleotide such as OligodT, an amino polysaccharide such as chitosan, a polyamine such as spermine, spermidine, cadaverine and putrescine, a polyamino acid, with a lysine or histidine, or any other polymeric compounds with dual functional groups which can be attached to the chemically activatable solid support on the bottom end, and the nucleic acid probes on the top domain. Preferably, the bifunctional polymer linker is OligodT having an amine group at the 5' end.

In this embodiment, the bifunctional polymer linker may be unmodified. Alternatively, the bifunctional polymer linker has a color or fluorescent label attached covalently. Examples of fluorescent labels include, but are not limited to the fluorescent dyes CY5, DYLIGHT™ DY647, ALEXA FLUOR® 647, CY3, DYLIGHT™ DY547, or ALEXA FLUOR® 550. These may be attached to any reactive group including but not limited to, amine, thiol, aldehyde, sugar amido and carboxy on the bifunctional polymer linker. The chemistries of such reactive groups are well known in the art and one or ordinary skill can readily identify a suitable group on a selected bifunctional polymer linker for attaching the fluorescent label. Preferably, the bifunctional polymer linker is CY5-labeled OligodT having an amino group attached at its 3' terminus for covalent attachment to an activated surface on the solid support.

Also in this embodiment, the present invention provides a plurality of nucleic acid probes designed with the purpose of identifying sequence determinants in plants, animals or pathogens. The nucleic acid probes are synthetic oligonucleotides and have terminal thymidine bases at their 5' and 3' end. The thymidine bases permit covalent attachment of the nucleic acid probes to the bifunctional polymer linker by any standard coupling procedures including but not limited to chemical, photochemical and thermal coupling. Preferably, covalent attachment of the nucleic acid probes to the bifunctional polymer linker is by photochemical means using ultraviolet light.

In this embodiment, the fluorescent label (fluorescent tag) attached to the bifunctional polymer linker is beneficial since it allows the user to image and detect the position of the individual nucleic acid probes ("spot") printed on the microarray. By using two different fluorescent labels, one for the bifunctional polymer linker and the second for the amplicons generated from the DNA being queried, the user can obtain a superimposed image that allows parallel detection of those nucleic acid probes which have been hybridized with amplicons. This is advantageous since it helps in identifying the plant or pathogen comprised in the sample using suitable computer and software, assisted by a database correlating nucleic acid probe sequence and microarray location of this sequence with a known DNA signature in plants, animals or pathogens. Any emitter/acceptor fluorescent label pairs known in the art may be used. For example, the bifunctional polymer linker may be labeled with emitters such as CY5, DYLIGHT™ DY647, or ALEXA FLUOR® 647, while the amplicons may be labeled with acceptors such as CY3, DYLIGHT™ DY547, or ALEXA FLUOR® 550. Preferably, the emitter is CY5 and the acceptor is CY3.

In another embodiment of this invention, there is provided a 3-dimensional lattice microarray system for screening a sample for the presence of a multiplicity of DNA. The system comprises a solid support, a fluorescent labeled bifunctional polymer linker and a plurality of nucleic acid probes designed to identify sequence determinants in plant, animal or pathogen DNA. In another aspect of this embodiment, there is provided a 3-dimensional lattice microarray system for quantitative screening of a sample for copy number of one or more types of DNA. The system comprises a bifunctional polymer linker, a plurality of nucleic acid probes designed to detect copy number of sequence determinants in plant, animal or pathogen DNA and, nucleic acid probes designed to detect copy number of an internal reference standard comprising a known copy number of synthetic DNA. The synthetic DNA has a central region with a nucleotide sequence distinct from signature sequence determinants in the unknown DNA being queried, and 5' and 3' ends sequences substantially identical to a consensus sequence in the unknown DNA. Such consensus sequences include but are not limited to the sequences shown in SEQ ID NO: 152 and 153. Such a structure for the synthetic DNA permits amplification of the synthetic DNA by the same pair of PCR primers used to amplify the hypervariable region of the unknown DNA being queried. Examples of such synthetic DNA which may be employed include but is not limited to the sequences shown in SEQ ID NOS: 154-157.

Further in this embodiment, the solid support may be made of any suitable material known in the art including but not limited to borosilicate glass, a thermoplastic acrylic resin such as poly(methylmethacrylate-VSUVT (PMMA-VSUVT), a cycloolefin polymers such as ZEONOR® 1060R, metals including, but not limited to gold and platinum, plastics including, but not limited to polyethylene terephthalate, polycarbonate, nylon, ceramics including, but not limited to $TiO_2$, and Indium tin oxide (ITO) and engineered carbon surfaces including, but not limited to graphene. The solid support has a front surface and a back surface and may be activated on the front surface with suitable chemicals which include but are not limited to epoxysilane, isocyanate, succinimide, carbodiimide, aldehyde and maleimide. These are well known in the art and one of ordinary skill in this art would be able to readily functionalize any of these supports as desired. In a preferred embodiment, the solid support is epoxysilane functionalized borosilicate glass support.

In this embodiment, the bifunctional polymer linker has a top domain and a bottom end. On the bottom end is attached a first reactive moiety that allows covalent attachment to the chemically activatable groups in the solid support. Examples of first reactive moieties include but are not limited to an amine group, a thiol group and an aldehyde group. Preferably, the first reactive moiety is an amine group. On the top domain of the bifunctional polymer linker is provided a second reactive moiety that allows covalent attachment to the oligonucleotide probe. Examples of second reactive moieties include but are not limited to nucleotide bases like thymidine, adenine, guanine, cytidine, uracil and bromodeoxyuridine and amino acid like cysteine, phenylalanine, tyrosine glycine, serine, tryptophan, cystine, methionine, histidine, arginine and lysine. The bifunctional polymer linker may be an oligonucleotide such as OligodT, an amino polysaccharide such as chitosan, a polyamine such as spermine, spermidine, cadaverine and putrescine, a polyamino acid, with a lysine or histidine, or any other polymeric compounds with dual functional groups which can be attached to the chemically activatable solid support on the bottom end, and the nucleic acid probes on the top domain. Preferably, the bifunctional polymer linker is OligodT having an amine group at the 5' end.

In one aspect of this embodiment, the bifunctional polymer linker is unmodified. Alternatively, the bifunctional polymer linker has a color or fluorescent label attached covalently. Examples of fluorescent labels include, but are not limited to the fluorescent dyes CY5, DYLIGHT™ DY647, ALEXA FLUOR® 647, CY3, DYLIGHT™ DY547, or ALEXA FLUOR® 550. These may be attached to any reactive group including but not limited to, amine, thiol, aldehyde, sugar amido and carboxy on the bifunctional polymer linker. The chemistries of such reactive groups are well known in the art and one or ordinary skill can readily identify a suitable group on a selected bifunctional polymer linker for attaching the fluorescent label. Preferably, the bifunctional polymer linker is CY5-labeled OligodT having an amino group attached at its 3'terminus for covalent attachment to an activated surface on the solid support.

Also, in this embodiment, the present invention provides a plurality of nucleic acid probes designed with the purpose of quantitating copy number of sequence determinants in plants, animals or pathogens and, nucleic acid probes designed to detect an internal reference standard comprising a known copy number of synthetic DNA. The nucleic acid probes are synthetic oligonucleotides and have terminal thymidine bases at their 5' and 3' end. The thymidine bases permit covalent attachment of the nucleic acid probes to the bifunctional polymer linker by any standard coupling procedures including but not limited to chemical, photochemical and thermal coupling. Preferably, covalent attachment of the nucleic acid probes to the bifunctional polymer linker is by photochemical means using ultraviolet light.

In this embodiment, the fluorescent label (fluorescent tag) attached to the bifunctional polymer linker is beneficial since it allows the user to image and detect the position of the individual nucleic acid probes ("spot") printed on the microarray. By using two different fluorescent labels, one for the bifunctional polymer linker and the second for the amplicons generated from the DNA being queried, the user can obtain a superimposed image that allows parallel detection of those nucleic acid probes which have been hybridized with amplicons. Furthermore, by using two different fluorescent labels, one for the bifunctional polymer linker and the second for the amplicons generated, one can quantitate copy number of the DNA being queried. This feature is advantageous since it allows; identification of the plant or pathogen comprised in the sample using suitable computer and software, assisted by a database correlating nucleic acid probe sequence and microarray location of this sequence with a known DNA signature in plants, animals or pathogens; and in addition, quantification of the copy number of the plant and/or pathogen DNA identified. Any emitter/acceptor fluorescent label pairs known in the art may be used for imaging and analysis. For example, the bifunctional polymer linker may be labeled with emitters such as CY5, DYLIGHT™ DY647, or ALEXA FLUOR® 647, while the amplicons may be labeled with acceptors such as CY3, DYLIGHT™ DY547, or ALEXA FLUOR® 550. Preferably, the emitter is CY5 and the acceptor is CY3.

In another embodiment of this invention, there is provided a 3-dimensional lattice microarray system for screening a sample for the presence of a multiplicity of DNA. The system comprises a solid support, a fluorescent labeled bifunctional polymer linker and a plurality of nucleic acid probes designed to identify sequence determinants in plant, animal or pathogen DNA.

In this embodiment, the solid support has a front surface and a back surface. The front surface has non-covalent adsorptive properties for specific functionalized group(s) present in the fluorescent labeled bifunctional polymer linker (described below). Examples of such solid support include, but are not limited to borosilicate glass, $SiO_2$, metals including, but not limited to gold and platinum, plastics including, but not limited to polyethylene terephthalate, polycarbonate, nylon, ceramics including, but not limited to $TiO_2$, and Indium tin oxide (ITO) and engineered carbon surfaces including, but not limited to graphene.

In this embodiment, the fluorescent labeled bifunctional polymer linker has a top domain and a bottom end. On the bottom end is attached one or more functional groups (designated by "$R_n$") that are compatible for non-covalent adsorptive attachment with the front surface of the solid support. Examples of compatible R groups include, but are not limited to, single stranded nucleic acids (example, OligodT), amine-polysaccharide (example, chitosan), extended planar hydrophobic groups (example, digoxigenin, pyrene, CY5 dye).

Further in this embodiment, on the top domain of the bifunctional polymer linker is provided a second reactive moiety that allows covalent attachment to the oligonucleotide probe. Examples of second reactive moieties include but are not limited to nucleotide bases like thymidine, adenine, guanine, cytidine, uracil and bromodeoxyuridine and amino acid like cysteine, phenylalanine, tyrosine glycine, serine, tryptophan, cystine, methionine, histidine, arginine and lysine. To the bottom end of the bifunctional polymer linker may be attached polymeric molecules including, but not limited to an oligonucleotide such as OligodT, an amino polysaccharide such as chitosan, a polyamine such as spermine, spermidine, cadaverine and putrescine, a polyamino acid, with a lysine or histidine, or OligodT that is modified at its 5' end with a digoxigenin, a pyrene or CY5 or any other polymeric molecules with or without chemical modification suitable for non-covalent attachment to the solid support. On the top domain of these bifunctional polymer linkers is attached, the nucleic acid probes. Preferably, the bifunctional polymer linker is OligodT.

In one aspect of this embodiment, the bifunctional polymer linker is unmodified. Alternatively, the bifunctional polymer linker may be a fluorescent labeled bifunctional polymer linker. The fluorescent label may be, but is not limited to the fluorescent dyes CY5, DYLIGHT™ DY647, ALEXA FLUOR® 647, CY3, DYLIGHT™ DY547, or ALEXA FLUOR® 550 attached to any reactive group including but not limited to, amine, thiol, aldehyde, sugar amido and carboxy on the bifunctional polymer linker. The chemistries of such reactive groups are well known in the art and one or ordinary skill can readily identify a suitable group on a selected bifunctional polymer linker for attaching the fluorescent label. Preferably, the bifunctional polymer linker is CY5-labeled OligodT.

Also, in one aspect of this embodiment, the present invention provides a plurality of nucleic acid probes designed with the purpose of identifying sequence determinants in plants, animals or pathogens. In another aspect of this embodiment, there is additionally provided nucleic acid probes that identify sequence determinants in a synthetic DNA added as an internal reference standard to the unpurified sample being queried (see below in the embodiments comprising the claimed methods) with the purpose of quantitating a DNA copy number for the identified plants, animals or pathogens. In either embodiment, the nucleic acid probes are synthetic oligonucleotides and have terminal thymidine bases at their 5' and 3' end. The thymidine bases permit covalent attachment of the nucleic acid probes to the bifunctional polymer linker by any standard coupling procedures including but not limited to chemical, photochemical and thermal coupling. Preferably, covalent attachment of the nucleic acid probes to the bifunctional polymer linker is by photochemical means using ultraviolet light.

Further in this embodiment, the fluorescent label (fluorescent tag) attached to the bifunctional polymer linker is beneficial since it allows the user to image and detect the position of the individual nucleic acid probes ("spot") printed on the microarray. By using two different fluorescent labels, one for the bifunctional polymer linker and the second for the amplicons generated from the DNA being queried, the user can obtain a superimposed image that allows parallel detection of those nucleic acid probes which have been hybridized with amplicons. This is advantageous since it helps in identifying the plant or pathogen comprised in the sample using suitable computer and software, assisted by a database correlating nucleic acid probe sequence and microarray location of this sequence with a known DNA signature in plants, animals or pathogens. Additionally, by using two different fluorescent labels, one for the bifunctional polymer linker and the second for the amplicons generated from the unknown DNA and the internal reference standard (synthetic DNA, which is added to the sample), one can quantitate copy number of the DNA being queried. This feature is advantageous since it allows; identification of the plant or pathogen comprised in the sample using suitable computer and software, assisted by a database of signature sequence determinants for correlating nucleic acid probe sequence and microarray location of this sequence to identify the plants, animals or pathogens; and in addition, quantification of the copy number of the plant and/or pathogen DNA identified.

Any emitter/acceptor fluorescent label pairs known in the art may be used. For example, the bifunctional polymer linker may be labeled with emitters such as CY5, DYLIGHT™ DY647, or ALEXA FLUOR® 647, while the amplicons may be labeled with acceptors such as CY3, DYLIGHT™ DY547, or ALEXA FLUOR® 550. Preferably, the emitter is CY5 and the acceptor is CY5.

In yet another embodiment of this invention, there is provided a method for fabricating a 3-dimensional lattice microarray system for the purpose of screening a sample for the presence of a multiplicity of DNA in a sample. The method comprises, contacting a solid support with a formulation comprising a plurality of nucleic acid probes, a plurality of fluorescent bifunctional polymer linkers and a solvent mixture comprising water and a high boiling point, water-miscible liquid, allowing a first attachment between the fluorescent bifunctional polymer linkers and the solid support to proceed, evaporating the water in the solvent mixture thereby concentrating the nucleic acid probes and fluorescent labeled bifunctional polymer linkers, allowing a second attachment between the nucleic acid probes and the fluorescent bifunctional polymer linker, and washing the solid support with at least once to remove unattached fluorescent bifunctional polymer linkers and nucleic acid probes.

In this embodiment, the contacting step is achieved by standard printing methods known in the art including, but not limited to piezo-electric printing, contact printing, ink jet printing and pipetting, which allow a uniform application of the formulation on the activated support. For this, any suitable solid support known in the art including but not limited to borosilicate glass, a polycarbonate, a graphene, a gold, a thermoplastic acrylic resin such as poly(methylmethacrylate-VSUVT (PMMA-VSUVT) and a cycloolefin polymer such as ZEONOR® 1060R may be employed.

In one aspect of this embodiment, the first attachment of the bifunctional polymer linker to the solid support is by non-covalent means such as by adsorption or electrostatic binding. In this case, the bifunctional polymer linkers with one or more functional groups (designated by "$R_n$") on the bottom end, that are compatible for attachment with the front surface of the solid support will be used. Examples of compatible R groups include, but are not limited to, single stranded nucleic acids (example, OligodT), amine-polysaccharide (example, chitosan), extended planar hydrophobic groups (example, digoxigenin, pyrene, CY5 dye). In another aspect of this embodiment, the first attachment of the bifunctional polymer linker to the solid support is by covalent coupling between chemically activatable groups on the solid support and a first reactive moiety on the bottom end of the bifunctional polymer linker. Suitable chemicals including but are not limited to epoxysilane, isocyanate, succinimide, carbodiimide, aldehyde and maleimide may be used for activating the support. These are well known in the art and one of ordinary skill in this art would be able to readily functionalize any of these supports as desired. In a preferred embodiment, a borosilicate glass support that is epoxysilane functionalized is used. Examples of first reactive moieties amenable to covalent first attachment include, but are not limited to an amine group, a thiol group and an aldehyde group. Preferably, the first reactive moiety is an amine group.

In this embodiment, the bifunctional polymer linker has a second reactive moiety attached at the top domain. Examples of second reactive moieties include but are not limited to nucleotide bases like thymidine, adenine, guanine, cytidine, uracil and bromodeoxyuridine and amino acid like cysteine, phenylalanine, tyrosine glycine, serine, tryptophan, cystine, methionine, histidine, arginine and lysine. Preferably, the second reactive moiety is thymidine. In this aspect of the invention, the bifunctional polymer linker may be an oligonucleotide such as OligodT, an amino polysaccharide such as chitosan, a polyamine such as spermine, spermidine, cadaverine and putrescine, a polyamino acid, with a lysine or histidine, or any other polymeric compounds with dual functional groups which can be attached to the chemically activatable solid support on the bottom end, and the nucleic acid probes on the top domain. Preferably, the bifunctional polymer linker is OligodT having an amine group at the 5' end.

In this embodiment, the bifunctional polymer linkers are modified with a fluorescent label. Examples of fluorescent labels include but are not limited to the fluorescent dyes CY5, DYLIGHT™ DY647, ALEXA FLUOR® 647, CY3, DYLIGHT™ DY547 and ALEXA FLUOR® 550 attached to any reactive group including but not limited to, amine, thiol, aldehyde, sugar amido and carboxy on the bifunctional polymer linker. The chemistries of such reactive groups are well known in the art and one or ordinary skill can readily identify a suitable group on a selected bifunctional polymer linker for attaching the fluorescent label. Preferably, the bifunctional polymer linker used for fabricating the microarray is CY5-labeled OligodT.

The method of fabricating the microarray requires use of a solvent mixture comprising water and a water-miscible liquid having a boiling point above 100° C. This liquid may be any suitable water-miscible liquid with a boiling point higher than that of water, so that all the solvent is not lost during the evaporation step. This allows the molecular reactants—nucleic acid probes and bifunctional linkers to be progressively concentrated during evaporation. Such controlled evaporation is crucial to the present invention since it controls the vertical spacing between nucleic acid probes their avoiding steric hindrance during the hybridization steps thereby improving accuracy and precision of the microarray. Examples of high boiling point water-miscible solvent include but are not limited to glycerol, DMSO and propanediol. The ratio or water to high boiling point solvent is kept between 10:1 and 100:1 whereby, in the two extremes, upon equilibrium, volume of the fluid phase will reduce due to water evaporation to between $\frac{1}{100}$th and $\frac{1}{10}^{th}$ of the original volume, thus giving rise to a 100-fold to 10-fold increase in reactant concentration. In a preferred embodiment, the water-miscible solvent is propanediol and the water to propanediol ratio is 100:1.

Further in this embodiment, the nucleic acid probes used in the method of microarray fabrication are designed with terminal thymidine bases at their 5' and 3' end. The thymidine bases permit covalent attachment of the nucleic acid probes to the bifunctional polymer linker by any standard coupling procedures including but not limited to chemical, photochemical and thermal coupling during the fabrication process. Preferably, coupling of the nucleic acid probes to the fluorescent labeled bifunctional polymer linkers is by photochemical covalent crosslinking.

In yet another embodiment of this invention, there is provided a customizable microarray kit. The kit comprises a solid support, a plurality of fluorescent labeled bifunctional polymer linkers, nucleic acid probes and a solvent mixture comprising water and one or more of a water-miscible liquid having a boiling point above 100° C., and instructions to use the kit. Each of the components comprising this kit may be individually customized prior to shipping based on the goals of the end user.

In this embodiment, the solid support has a front surface and a back surface and made of any suitable material known in the art including but not limited to borosilicate glass, a polycarbonate, a graphene, a gold, a thermoplastic acrylic resin such as poly(methylmethacrylate-VSUVT (PMMA-VSUVT) and a cycloolefin polymer such as ZEONOR® 1060R.

In one aspect of this embodiment, the solid support is unmodified and has properties capable of non-covalent attachment to groups in the bifunctional polymer linker. Alternatively, the solid support is activated on the front surface with chemically activatable groups which include but are not limited to epoxysilane, isocyanate, succinimide, carbodiimide, aldehyde and maleimide. These are well known in the art and one of ordinary skill in this art would be able to readily functionalize any of these supports as desired. In a preferred embodiment, the solid support is epoxysilane functionalized borosilicate glass support.

In this embodiment, the bifunctional polymer linker has a top domain and a bottom end. In one aspect of this embodiment, to the bottom end of the bifunctional polymer linker are attached one or more functional groups (designated by "$R_n$"), which are compatible for attachment with the front surface of the solid support in a non-covalent binding. Examples of such compatible R groups include, but are not limited to, single stranded nucleic acids (example, OligodT), amine-polysaccharide (example, chitosan), extended planar hydrophobic groups (example, digoxigenin, pyrene, CY5 dye). Alternatively, to the bottom end of the bifunctional polymer linker are attached a first reactive moiety that allows covalent attachment to chemically activatable groups in the solid support. Examples of first reactive moieties include but are not limited to an amine group, a thiol group and an aldehyde group. Preferably, the first reactive moiety is an amine group.

Further in this embodiment, on the top domain of the bifunctional polymer linker is provided a second reactive moiety that allows covalent attachment to the oligonucleotide probe. Examples of second reactive moieties include but are not limited to nucleotide bases like thymidine, adenine, guanine, cytidine, uracil and bromodeoxyuridine and amino acid like cysteine, phenylalanine, tyrosine glycine, serine, tryptophan, cystine, methionine, histidine, arginine and lysine. The bifunctional polymer linker may be an oligonucleotide such as OligodT, an amino polysaccharide such as chitosan, a polyamine such as spermine, spermidine, cadaverine and putrescine, a polyamino acid, with a lysine or histidine, or any other polymeric compounds with dual functional groups for attachment to the solid support from the bottom end, and the nucleic acid probes from the top domain.

In one aspect of this embodiment, the bifunctional polymer linkers are modified with a fluorescent label. Alternatively, the bifunctional polymer linker may be a fluorescent labeled bifunctional polymer linker where the fluorescent label is either of CY5, DYLIGHT™ DY647, ALEXA FLUOR® 647, CY3, DYLIGHT™ DY547, or ALEXA FLUOR® 550 attached to any reactive group including but not limited to, amine, thiol, aldehyde, sugar amido and carboxy on the bifunctional polymer linker. The chemistries of such reactive groups are well known in the art and one or ordinary skill can readily identify a suitable group on a selected bifunctional polymer linker for attaching the fluorescent label. Preferably, the bifunctional polymer linker is CY5-labeled OligodT.

Also in this embodiment, the present invention provides a plurality of nucleic acid probes designed with the purpose of identifying sequence determinants in plants, animals or pathogens. The nucleic acid probes are synthetic oligonucleotides and have terminal thymidine bases at their 5' and 3' end. The thymidine bases permit covalent attachment of the nucleic acid probes to the bifunctional polymer linker by any standard coupling procedures including but not limited to chemical, photochemical and thermal coupling. Preferably, covalent attachment of the nucleic acid probes to the bifunctional polymer linker is by photochemical means using ultraviolet light. In an alternative aspect of this embodiment, the present invention provides a plurality of nucleic acid probes designed with the purpose of identifying sequence determinants in plants, animals or pathogens and, a synthetic DNA internal reference standard, which is added to the sample to quantitate DNA copy number for the sequence determinants in plants, animals or pathogens. The synthetic DNA has a central region with a nucleotide sequence distinct from signature sequence determinants in the unknown DNA being queried, and 5' and 3' ends sequences substantially identical to a consensus sequence in the unknown DNA. Such consensus sequences include but are not limited to the sequences shown in SEQ ID NO: 152 and 153. Such a structure for the synthetic DNA permits amplification of the synthetic DNA by the same pair of PCR primers used to amplify the hypervariable region of the unknown DNA being queried. Examples of such synthetic DNA which may be employed include but is not limited to the sequences shown in SEQ ID NOs: 154-157. In either of these embodiment, the nucleic acid probes are synthetic oligonucleotides and have terminal thymidine bases at their 5' and 3' end. The thymidine bases permit covalent attachment of the nucleic acid probes to the bifunctional polymer linker by any standard coupling procedures including but not limited to chemical, photochemical and thermal coupling. Preferably, covalent attachment of the nucleic acid probes to the bifunctional polymer linker is by photochemical means using ultraviolet light.

In yet another embodiment of this invention there is provided a method for detecting the presence of one or more pathogens in a plant sample. In this embodiment, the pathogen may be a human pathogen, an animal pathogen or a plant pathogen, such as a bacterium, a fungus, a virus, a yeast, algae or a protozoan or a combination thereof. These pathogens may be present as constituents of the soil, soilless growth media, hydroponic growth media or water in which the plant sample was grown. The method comprises harvesting the pathogens from the plant sample, isolating total nucleic acids comprising pathogen DNA, performing a first amplification for generating one or more amplicons from the one or more pathogens present in the sample in a single, simultaneous step; performing a labeling amplification using as template, the one or more amplicons generated in the first amplification step to generate fluorescent labeled second amplicons; hybridizing the second amplicons with the nucleic acid probes immobilized on the fabricated self-assembled, 3-dimensional lattice microarray described above and imaging the microarray to detect the fluorescent signal, which indicates presence of the one or more pathogens in a plant sample. In this embodiment, the pathogens present on the plant surface may be harvested by washing the plant with water to recover the pathogens, followed by concentrating by filtration on a sterile 0.4 µm filter. In another aspect of this embodiment, pathogens within the plant tissue may be harvested by fluidizing the plant tissue sample and pathogens, followed by centrifuging to get a pellet of plant cells and pathogen cells. In either embodiment, the harvested sample is disrupted to release the total nucleic acids which is used in the subsequent steps without further purification.

Also in this embodiment, the sample comprising nucleic acids from pathogens (external pathogens) or nucleic acids from both pathogens and plant (internal pathogens) is used to perform a first amplification of pathogen DNA using pathogen-specific first primer pairs to obtain one or more pathogen-specific first amplicons. Any DNA amplification methodology, including loop-mediated isothermal amplification (LAMP) or polymerase chain reaction (PCR) that can selectively amplify the DNA complement in the sample may be employed. In a preferred embodiment, the amplification is by PCR. In one embodiment, the pathogen is a bacterium and the first primer pairs have sequences shown in SEQ ID NOS: 1-12. In another embodiment, the pathogen is a fungus and the first primer pairs have sequences shown in SEQ ID NOS: 13-16. An aliquot of first amplicons so generated is used as template for a second, labelling PCR amplification using fluorescent labeled second primer pairs. The second primer pairs are designed to amplify an internal flanking region in the one or more first amplicons to obtain one or more first fluorescent labeled second amplicons. In one embodiment, the pathogen is a bacterium and the second primer pairs have sequences shown in SEQ ID NOS: 19-30. In another embodiment, the pathogen is a fungus and the second primer pairs have sequences shown in SEQ ID NOS: 31-34.

Further in this embodiment, the fluorescent labeled second amplicons are hybridized on a 3-dimensional lattice microarray system having a plurality of nucleic acid probes as described in detail above. In this embodiment, the bifunctional polymer linker has a fluorescent label (that is different from the label on the second amplicon) attached whereby, imaging the microarray after hybridization and washing results in two distinct fluorescent signals—the signal from the fluorescent bifunctional polymer linker which is covalently linked to the nucleic acid probe during fabrication, which would be detected in each spot comprised in the microarray, and a second amplicon signal that would be detected only in those spots where the nucleic acid probe sequence is complementary to the second amplicon (originally derived by amplification from the pathogen DNA in the sample). Thus, superimposing the two images using a computer provides beneficial attributes to the system and method claimed in this invention since one can readily identify the plant or pathogen comprised in the sample from a database that correlates nucleic acid probe sequence and microarray location of this sequence with a known DNA signature in plants or pathogens. In a preferred embodiment, the bacterial nucleic acid probes having sequences shown in SEQ ID NOS: 37-85. and fungal nucleic acid probes having sequences shown in SEQ ID NOS: 86-125 may be used for this purpose.

Further to this embodiment is a method for detecting plant DNA. The plant may be a terrestrial plant such as a *Humulus* or a *Cannabis*, an aquatic plant, an epiphytic plant or a lithophytic plant that grows in soil, soilless media, hydroponic growth media or water. In a preferred aspect, the plant is a *Cannabis*. This method comprises the steps of performing an amplification on an unpurified complex nucleic acid sample using plant-specific first primer pairs to generate plant-specific first amplicons. In one aspect of this embodiment, the first primer pair has sequences shown in SEQ ID NOS: 17-18. Any DNA amplification methodology, including loop-mediated isothermal amplification (LAMP) or polymerase chain reaction (PCR) that can selectively amplify the DNA complement in the sample may be employed. Preferably the amplification is by PCR. The first amplicons so generated are used as template for a labeling amplification step using fluorescent labeled second primer pairs that are designed to amplify an internal flanking region in the one or more of first amplicons generated in the first amplification step to generate one or more first fluorescent labeled second amplicons. In one embodiment, the second primer pair has sequences shown in SEQ ID NOS: 35-36. The second amplicons are hybridized on a 3-dimensional lattice microarray system having a plurality of plant-specific nucleic acid probes, and the microarrays imaged and analyzed as described above for identifying pathogen DNA. In one aspect of this embodiment, the hybridization nucleic acid probes have sequences shown in SEQ ID NOS: 126-128.

In yet another embodiment of this invention, there is provided a method for simultaneously detecting resident pathogen DNA and plant DNA in a plant sample in a single assay. In this embodiment, the pathogen may be a human pathogen, an animal pathogen or a plant pathogen, which may be a bacterium, a fungus, a virus, a yeast, algae or a protozoan or a combination thereof. These pathogens may be present as constituents of the soil, soilless growth media, hydroponic growth media or water in which the plant sample was grown. The plant may be a terrestrial plant such as a *Humulus* or a *Cannabis*, an aquatic plant, an epiphytic plant or a lithophytic plant that grows in soil, soilless media, hydroponic growth media or water. Preferably, the plant is a *Cannabis*.

In this embodiment, the method comprises harvesting a plant tissue sample potentially comprising one or more pathogens, fluidizing the plant tissue sample and the one or more pathogens and isolating total nucleic acids comprising DNA from at least the plant tissue and DNA from the one or more pathogens. In one aspect of this embodiment, the step of isolating total nucleic acids comprises centrifuging the fluidized sample to get a pellet of plant cells and pathogen cells which are disrupted to release the total nucleic acids, which are used in the subsequent steps without further purification.

Further in this embodiment, a first amplification is performed on the unpurified total nucleic acid sample using one or more of a first primer pair each selective for the one or more pathogen DNA and one or more of a second primer pair selective for the plant DNA to generate one or more pathogen-specific first amplicons and one or more plant-specific second amplicons. Any DNA amplification methodology, including loop-mediated isothermal amplification (LAMP) or polymerase chain reaction (PCR) that can selectively amplify the DNA complement in the sample may be employed. In a preferred embodiment, the amplification is by PCR. In one embodiment, the pathogen is a bacterium and the first primer pairs have sequences shown in SEQ ID NOS: 1-12. In another embodiment, the pathogen is a fungus and the first primer pairs have sequences shown in SEQ ID NOS: 13-16. In either of these embodiments, the plant-specific second primer pairs have sequences shown in SEQ ID NOS: 35-36. An aliquot of the first and second amplicons so generated is used as a template for a second, labeling PCR amplification step using fluorescent labeled third primer pairs having a sequence complementary to an internal flanking region in the one or more pathogen-specific first amplicons and fluorescent labeled fourth primer pairs having a sequence complementary to an internal flanking region in the one or more plant-specific second amplicons. Any DNA amplification methodology, including loop-mediated isothermal amplification (LAMP) or polymerase chain reaction (PCR) that can selectively amplify the DNA complement in the sample may be employed. In a preferred embodiment, the amplification is by PCR. In one embodiment, the pathogen is a bacterium and the third primer pairs have sequences shown in SEQ ID NOS: 19-30. In another embodiment, the pathogen is a fungus and the third primer pairs have sequences shown in SEQ ID NOS: 31-34. In either of these embodiments, the plant-specific fourth primer pairs have sequences shown in SEQ ID NOS: 35-36. The labeling PCR step results in generation of first fluorescent labeled third amplicons and second fluorescent labeled fourth amplicons corresponding to the pathogen and plant DNA respectively in the original harvested sample. These amplicons are then hybridized on a 3-dimensional lattice microarray system having a plurality of nucleic acid probes specific to sequence determinants in pathogen DNA or plant DNA. Bacterial nucleic acid probes having sequences shown in SEQ ID NOS: 37-85, fungal nucleic acid probes having sequences shown in SEQ ID NOS: 86-125 and plant nucleic acid probes having sequences shown in SEQ ID NOS: 126-128. may be used for this purpose. After hybridization, unhybridized amplicons are removed by washing and the microarray imaged. Detection of the first fluorescent labeled third amplicon signal indicates presence of pathogens in the plant sample. Detecting the second fluorescent labeled fourth amplicon indicates presence of the plant DNA. Superimposing these two signals with the third fluorescent signal from the fluorescent bifunctional polymer linker-coupled nucleic acid probes allow simultaneous identification of the pathogen and plant in the sample by correlating nucleic acid probe sequence and microarray location of this sequence with a known DNA signature in plants or pathogens. These features provide beneficial attributes to the system and method claimed in this invention.

In yet another embodiment of this invention there is provided a method for both detecting the presence of one or more pathogens and quantitating the copy number of pathogen DNA and plant DNA in a plant sample by introducing a known copy number of a synthetic DNA sequence as an internal reference standard to the plant sample. In this embodiment, the pathogen may be a human pathogen, an animal pathogen or a plant pathogen, such as a bacterium, a fungus, a virus, a yeast, algae or a protozoan or a combination thereof. These pathogens may be present as constituents of the soil, soilless growth media, hydroponic growth media or water in which the plant sample was grown. The method comprises harvesting the pathogens from the plant sample, isolating total nucleic acids comprising pathogen DNA, performing a first amplification for generating one or more amplicons from the one or more pathogens present in the sample in a single, simultaneous step; performing a labeling amplification using as template, the one or more amplicons generated in the first amplification step to generate fluorescent labeled second amplicons; hybridizing the second amplicons with the nucleic acid probes immobilized on the fabricated self-assembled, 3-dimensional lattice microarray described above and imaging the microarray to detect the fluorescent signal, which indicates presence of the one or more pathogens in a plant sample. In this embodiment, the pathogens present on the plant surface may be harvested by washing the plant with water to recover the pathogens, followed by concentrating by filtration on a sterile 0.4 μm filter. In another aspect of this embodiment, pathogens within the plant tissue may be harvested by fluidizing the plant tissue sample and pathogens, followed by centrifuging to get a pellet of plant cells and pathogen cells. In either embodiment, the harvested sample is disrupted to release the total nucleic acids which is used in the subsequent steps without further purification.

In this embodiment, the synthetic DNA has a central region with a nucleotide sequence distinct from signature sequence determinants in the unknown DNA being queried, and 5' and 3' ends sequences substantially identical to a consensus sequence in the unknown DNA. Such consensus sequences include but are not limited to the sequences shown in SEQ ID NO: 152 and 153. Such a structure for the synthetic DNA permits amplification of the synthetic DNA by the same pair of PCR primers used to amplify the hypervariable region of the unknown DNA being queried. Examples of such synthetic DNA which may be employed include but is not limited to the sequences shown in SEQ ID NOs: 154 (fungus) and 155-157 (bacteria).

Also in this embodiment, a known copy number of a synthetic DNA is added to the sample comprising nucleic acids from pathogens (external pathogens) or nucleic acids from both pathogens and plant (internal pathogens) and a first amplification is performed using pathogen-specific first primer pairs to obtain one or more pathogen-specific first amplicons and synthetic DNA specific second amplicons. Any DNA amplification methodology, including loop-mediated isothermal amplification (LAMP) or polymerase chain reaction (PCR) that can selectively amplify the DNA complement in the sample may be employed. In a preferred embodiment, the amplification is by PCR. Any suitable first amplification primer pairs may be used for this purpose and one of skill in this art can easily design these primers based on the pathogen of interest. In one embodiment, the pathogen is a bacterium and the first primer pairs have sequences shown in SEQ ID NOS: 1 and 2, or SEQ ID NOS: 3 and 4, or SEQ ID NOS: 5 and 6 or SEQ ID NOS: 7 and 8, or SEQ ID NOS: 9 and 10, or SEQ ID NOS: 11 and 12, or SEQ ID NOS: 137 and 138. In another embodiment, the pathogen is a fungus and the first primer pairs have sequences shown in SEQ ID NOS: 13 and 14, or SEQ ID NOS: 15 and 16, or SEQ ID NOS: 135 and 136. An aliquot of first and second amplicons so generated is used as template for a second, labelling PCR amplification using fluorescent labeled second primer pairs. The second primer pairs are designed to amplify an internal flanking region in the one or more pathogen DNA-specific first amplicons and the synthetic DNA-specific second amplicons to obtain one or more first fluorescent labeled third amplicons and first fluorescent labeled fourth amplicons. Any suitable second amplification primer pairs may be used for this purpose and one of skill in this art can easily design these primers based on the pathogen of interest. In one embodiment, the pathogen is a bacterium and the second primer pairs have sequences shown in SEQ ID NOS: 19 and 20, or SEQ ID NOS: 21 and 22, or SEQ ID NOS: 23 and 24 or SEQ ID NOS: 25 and 26, or SEQ ID NOS: 27 and 28, or SEQ ID NOS: 29 and 30, or SEQ ID NOS: 141 and 30. In another embodiment, the pathogen is a fungus and the second primer pairs have sequences shown in SEQ ID NOS: 31 and 32, or SEQ ID NOS: 33 and 34, or SEQ ID NOS: 139 and 140.

Further in this embodiment, the fluorescent labeled second amplicons are hybridized on a 3-dimensional lattice microarray system having a plurality of nucleic acid probes specific to pathogen or synthetic DNA specific amplicons as described in detail above. Any suitable nucleic acid probes may be used for this purpose and one of skill in this art can easily design them based on the pathogen of interest. In one embodiment, the bacterial nucleic acid probes have sequences shown in SEQ ID NOS: 37-85 and the synthetic DNA has sequences shown in SEQ ID NO: 155, SEQ ID NO: 156 corresponding respectively to synthetic DNA specific nucleic acid probes having sequences shown in SEQ ID NO: 142, SEQ ID NO: 143 and SEQ ID NO: 144. In another embodiment, the fungal nucleic acid probes having sequences shown in SEQ ID NOS: 86-125, the synthetic DNA has sequences shown in SEQ ID NO: 154 that corresponds to synthetic DNA specific nucleic acid probes having sequences shown in SEQ ID NO: 145.

In this embodiment, the bifunctional polymer linker has a fluorescent label (that is different from the label on the second amplicon) attached whereby, imaging the microarray after hybridization and superimposing the image results in two fluorescent signals—the signal from the fluorescent bifunctional polymer linker which is covalently linked to the nucleic acid probe during fabrication, which would be detected in each spot comprised in the microarray, and the signal from fluorescent labeled third and fourth amplicons corresponding to pathogen and synthetic DNA respectively and which would be detected only in those positions (spots) where the nucleic acid probe sequence is complementary to the pathogen specific third amplicon (originally derived by amplification from the pathogen DNA in the sample) and synthetic DNA specific fourth amplicon. Thus, superimposing the signals using a computer provides beneficial attributes to the system and method claimed in this invention since one can readily identify the plant or pathogen comprised in the sample from a database that correlates nucleic acid probe sequence and microarray location of this sequence with a known DNA signature in plants or pathogens. Further to this embodiment, the relative fluorescence intensities (RFU) from the microarray image corresponding to fluorescent pathogen DNA-specific amplicons, fluorescent plant DNA-specific amplicons are analyzed and mathematically correlated with fluorescence intensity for the synthetic DNA-specific amplicons and the known copy number for the synthetic DNA added to the sample, to determine copy numbers of the pathogen DNA and plant DNA in the sample, the mathematical correlation being;

$$C_n/C_o = P(S_n/S_o)^x \text{ where,} \quad \text{Equation \#1}$$

$C_n$=the number of microbial DNA copies of each type (n) present in the original sample mixture added to the first of two tandem PCR reactions used to prepare amplicons for microarray analysis.

$C_o$=the number of known synthetic DNA copies (internal reference standard) added to the first of two PCR reactions used to prepare amplicons for microarray analysis. $C_o$ may be set at any value including but not limited to 100, 500, 3,000 and 5,000 depending on the range of unknown microbial copies which might be encountered. In a preferred embodiment $C_o$=3000.

$S_n$=relative fluorescence units (RFU) signal data obtained after PCR amplification, and microarray hybridization of the nth microbial species, followed by image analysis.

$S_o$=relative fluorescence units (RFU) signal data obtained after PCR amplification, and microarray hybridization of the synthetic DNA species, followed by image analysis.

X=a complex exponential factor which defines the functional relationship between the Experimental Microarray Data Ratio ($S_n/S_o$) to the underlying ratio of microbial DNA copies vs synthetic DNA standard copies present in the original sample ($C_n/C_o$). X may be a linear function or exponential or related functional form or a constant which is itself a function of amplification parameters and conditions of microarray analysis and imaging. In one aspect, X is an exponential factor ranging from about 1 to about 3.

P=A constant which relates the Experimental Microarray Data ratio ($S_n/S_o$) to the concentration of amplified PCR product which binds to the microarray. In one aspect, P may range from about 0.1 to about 10.

In yet another embodiment of this invention, there is provided a method for simultaneously detecting and quantitating resident pathogen DNA and plant DNA in a plant sample in a single assay by introducing a known copy number of a synthetic DNA sequence as an internal reference standard to the plant sample. In this embodiment, the pathogen may be a human pathogen, an animal pathogen or a plant pathogen, which may be a bacterium, a fungus, a virus, a yeast, algae or a protozoan or a combination thereof. These pathogens may be present as constituents of the soil, soilless growth media, hydroponic growth media or water in which the plant sample was grown. The plant may be a terrestrial plant such as a *Humulus* or a *Cannabis*, an aquatic plant, an epiphytic plant or a lithophytic plant that grows in soil, soilless media, hydroponic growth media or water. Preferably, the plant is a *Cannabis*.

In this embodiment, the method comprises harvesting a plant tissue sample potentially comprising one or more pathogens, fluidizing the plant tissue sample and the one or more pathogens and isolating total nucleic acids comprising DNA from at least the plant tissue and DNA from the one or more pathogens. In one aspect of this embodiment, the step of isolating total nucleic acids comprises centrifuging the fluidized sample to get a pellet of plant cells and pathogen cells which are disrupted to release the total nucleic acids, which are used in the subsequent steps without further purification. To this unpurified total nucleic acid sample is added a known copy number of synthetic DNA. The synthetic DNA has a central region with a nucleotide sequence distinct from signature sequence determinants in the unknown DNA being queried, and 5' and 3' ends sequences substantially identical to a consensus sequence in the unknown DNA. Such consensus sequences include but are not limited to the sequences shown in SEQ ID NO: 152 and 153. Such a structure for the synthetic DNA permits amplification of the synthetic DNA by the same pair of PCR primers used to amplify the hypervariable region of the unknown DNA being queried. Examples of such synthetic DNA which may be employed include but is not limited to the sequences shown in SEQ ID NOs: 154 (fungus) and 155-157 (bacteria).

Further in this embodiment, a first amplification is performed on the unpurified total nucleic acid sample using one or more of a first primer pair selective for the pathogen DNA and the synthetic DNA and one or more of a second primer pair selective for the plant DNA to generate one or more pathogen-specific first amplicons and one or more plant-specific second amplicons and synthetic DNA-specific third amplicons. Any DNA amplification methodology, including loop-mediated isothermal amplification (LAMP) or polymerase chain reaction (PCR) that can selectively amplify the DNA complement in the sample may be employed. In a preferred embodiment, the amplification is by PCR. Any suitable first amplification primer pairs may be used for this purpose and one of skill in this art can easily design these primers based on the pathogen and plant of interest. In one embodiment, the pathogen is a bacterium and the first primer pairs have sequences shown in SEQ ID NOS: 1 and 2, or SEQ ID NOS: 3 and 4, or SEQ ID NOS: 5 and 6 or SEQ ID NOS: 7 and 8, or SEQ ID NOS: 9 and 10, or SEQ ID NOS: 11 and 12, or SEQ ID NOS: 137 and 138. In another embodiment, the pathogen is a fungus and the first primer pairs have sequences shown in SEQ ID NOS: 13 and 14, or SEQ ID NOS: 15 and 16, or SEQ ID NOS: 135 and 136. In either of these embodiments, the plant-specific second primer pairs have sequences shown in SEQ ID NOS: 17 and 18. An aliquot of the first, second, and third amplicons so generated is used as a template for a second, labeling PCR amplification step using a first fluorescent labeled third primer pairs having a sequence complementary to an internal flanking region in the first amplicons and third amplicons and second fluorescent labeled fourth primer pairs having a sequence complementary to an internal flanking region in the one or more plant-specific second amplicons to obtain pathogen DNA-specific first fluorescent labeled fourth amplicons, plant DNA-specific second fluorescent labeled fifth amplicons and synthetic DNA-specific first fluorescent labeled sixth amplicons. Any DNA amplification methodology, including loop-mediated isothermal amplification (LAMP) or polymerase chain reaction (PCR) that can selectively amplify the DNA complement in the sample may be employed. In a preferred embodiment, the amplification is by PCR. Any suitable second amplification primer pairs may be used for this purpose and one of skill in this art can easily design these primers based on the pathogen and plant of interest. In one embodiment, the pathogen is a bacterium and the second primer pairs have sequences shown in SEQ ID NOS: 19 and 20, or SEQ ID NOS: 21 and 22, or SEQ ID NOS: 23 and 24 or SEQ ID NOS: 25 and 26, or SEQ ID NOS: 27 and 28, or SEQ ID NOS: 29 and 30, or SEQ ID NOS: 141 and 30. In another embodiment, the pathogen is a fungus and the second primer pairs have sequences shown in SEQ ID NOS: 31 and 32, or SEQ ID NOS: 33 and 34, or SEQ ID NOS: 139 and 140. In either of these embodiments, the plant-specific fourth primer pairs have sequences shown in SEQ ID NOS: 35-36.

Further in this embodiment, the fourth, fifth and sixth amplicons are then hybridized on a 3-dimensional lattice microarray system having a plurality of nucleic acid probes specific to sequence determinants in pathogen DNA, plant DNA or synthetic DNA. Any suitable nucleic acid probes may be used for this purpose and one of skill in this art can easily design them based on the pathogen of interest. In one embodiment, the bacterial nucleic acid probes have sequences shown in SEQ ID NOS: 37-85 and the synthetic DNA has sequences shown in SEQ ID NO: 155, SEQ ID NO: 156 corresponding respectively to synthetic DNA specific nucleic acid probes having sequences shown in SEQ ID NO: 142, SEQ ID NO: 143 and SEQ ID NO: 144. In another embodiment, the fungal nucleic acid probes having sequences shown in SEQ ID NOS: 86-125, the synthetic DNA has sequences shown in SEQ ID NO: 154 that corresponds to synthetic DNA specific nucleic acid probes having sequences shown in SEQ ID NO: 145. In either embodiment, plant nucleic acid probes having sequences shown in SEQ ID NOS: 126-128. In this embodiment, the nucleic acid probes are attached to the microarray via a third fluorescent label bifunctional polymer linker has a (third fluorescent label is different from the first and second fluorescent label on the amplicons). Thereby, imaging of the hybridized amplicons on the microarray gives fluorescent signals—the third fluorescent signal from the nucleic acid probes that are attached to the bifunctional polymer linker, first fluorescent signal from the hybridized pathogen-specific fourth, and synthetic DNA-specific sixth amplicons and second fluorescent signal from the hybridized plant-specific fifth amplicons. Superimposing each of the first and second fluorescent third signals with the third fluorescent signal from the nucleic acid probe using a computer provides beneficial attributes to the system and method claimed in this invention since one can readily identify the plant or pathogen comprised in the sample from a database that correlates nucleic acid probe sequence and microarray location of this sequence with a known DNA signature in plants or pathogens. Further to this embodiment, the relative fluorescence intensities (RFU) from the microarray image corresponding to fluorescent pathogen DNA-specific amplicons, fluorescent plant DNA-specific amplicons are analyzed and mathematically correlated with fluorescence intensity for the synthetic DNA-specific amplicons and the known copy number for the synthetic DNA added to the sample, to determine copy numbers of the pathogen DNA and plant DNA in the sample, the mathematical correlation being;

$$C_n/C_o = P(S_n/S_o)^x \text{ where,} \qquad \text{Equation \#1}$$

$C_n$=the number of microbial DNA copies of each type (n) present in the original sample mixture added to the first of two tandem PCR reactions used to prepare amplicons for microarray analysis.

$C_o$=the number of known synthetic DNA copies (internal reference standard) added to the first of two PCR reactions used to prepare amplicons for microarray analysis. $C_o$ may be set at any value including but not limited to 100, 500, 3,000 and 5,000 depending on the range of unknown microbial copies which might be encountered. In a preferred embodiment $C_o$=3000.

$S_n$=relative fluorescence units (RFU) signal data obtained after PCR amplification, and microarray hybridization of the nth microbial species, followed by image analysis.

$S_o$=relative fluorescence units (RFU) signal data obtained after PCR amplification, and microarray hybridization of the synthetic DNA species, followed by image analysis.

X=a complex exponential factor which defines the functional relationship between the Experimental Microarray Data Ratio ($S_n/S_o$) to the underlying ratio of microbial DNA copies vs synthetic DNA standard copies present in the original sample ($C_n/C_o$). X may be a linear function or exponential or related functional form or a constant which is itself a function of amplification parameters and conditions of microarray analysis and imaging. In one aspect, X is an exponential factor ranging from about 1 to about 3.

P=A constant which relates the Experimental Microarray Data ratio ($S_n/S_o$) to the concentration of amplified PCR product which binds to the microarray. In one aspect, P may range from about 0.1 to about 10.

In yet another embodiment of the present disclosure there is provided a method for DNA based pathogen analysis. The embodiments of the present disclosure use DNA amplification methodologies, including loop-mediated isothermal amplification (LAMP) or polymerase chain reaction (PCR) tests that can selectively amplify the DNA complement of that plant material using unpurified plant and pathogen material. The embodiments are also based on the use of aforementioned PCR-amplified DNA as the substrate for microarray-based hybridization analysis, wherein the hybridization is made simple because the nucleic acid probes used to interrogate the DNA of such pathogens are optimized to function at room temperature. This enables the use of the above-mentioned microarray test at ambient temperature, thus bypassing the prior art requirement that testing be supported by an exogenous temperature-regulating device.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Fabrication of 3-Dimensional Lattice Microarray Systems

The present invention teaches a way to link a nucleic acid probe to a solid support surface via the use of a bifunctional polymeric linker. The nucleic acid probe can be a PCR amplicon, synthetic oligonucleotides, isothermal amplification products, plasmids or genomic DNA fragment in a single stranded or double stranded form. The invention can be sub-divided into two classes, based on the nature of the underlying surface to which the nucleic acid probe would be linked.

Covalent Microarray System with Activated Solid Support

The covalent attachment of any one of these nucleic acid probes does not occur to the underlying surface directly, but is instead mediated through a relatively long, bi-functional polymeric linker that is capable of both chemical reaction with the surface and also capable of efficient UV-initiated crosslinking with the nucleic acid probe. The mechanics of this process is spontaneous 3D self assembly and is illustrated in FIG. 1A-FIG. 1D. As seen in FIG. 1A, the components required to fabricate this microarray system are:

(a) an unmodified nucleic acid probe 3 such as an oligonucleotide, PCR or isothermal amplicon, plasmid or genomic DNA;

(b) a chemically activatable surface 1 with chemically activatable groups (designated "X") compatible for reacting with a primary amine such as. epoxysilane, isocyanate, succinimide, carbodiimide, aldehyde.

(c) bifunctional polymer linkers 2 such as a natural or modified OligodT, amino polysaccharide, amino polypeptide suitable for coupling to chemically activatable groups on the support surface, each attached with a fluorescent label 4; and (d) a solvent comprising water and a high boiling point, water-miscible liquid such as glycerol, DMSO or propanediol (water to solvent ratio between 10:1 and 100:1).

Table 1 shows examples of chemically activatable groups and matched reactive groups on the bifunctional polymer linker for mere illustration purposes only and does not in any way preclude use of other combinations of matched reactive pairs.

TABLE 1

Covalent Attachment of Bifunctional Polymeric Linker to an Activated Surfaces

| Activated Surface Moiety | Matched Reactive Group on Bifunctional Linker | Specific Implementation as Bifunctional polymeric linker |
|---|---|---|
| Epoxysilane | Primary Amine | (1) Amine-modified OligodT (20-60 bases) |
|  |  | (2) Chitosan (20-60 subunits) |
|  |  | (3) Lysine containing polypeptide (20-60aa) |
| EDC Activated Carboxylic Acid | Primary Amine | (4) Amine-modified OligodT (20-60 bases) |
|  |  | (5) Chitosan (20-60 subunits) |
|  |  | (6) Lysine containing polypeptide (20-60aa) |
| N-hydroxysuccinimide (NHS) | Primary Amine | (7) Amine-modified OligodT (20-60 bases) |
|  |  | (8) Chitosan (20-60 subunits) |
|  |  | (9) Lysine containing polypeptide (20-60aa) |

When used in the present invention, the chemically activatable surface, bifunctional polymer linkers and unmodified nucleic acid probes are included as a solution to be applied to a chemically activated surface 4 by ordinary methods of fabrication used to generate DNA Hybridization tests such as contact printing, piezo electric printing, ink jet printing, or pipetting.

Figure 1B:
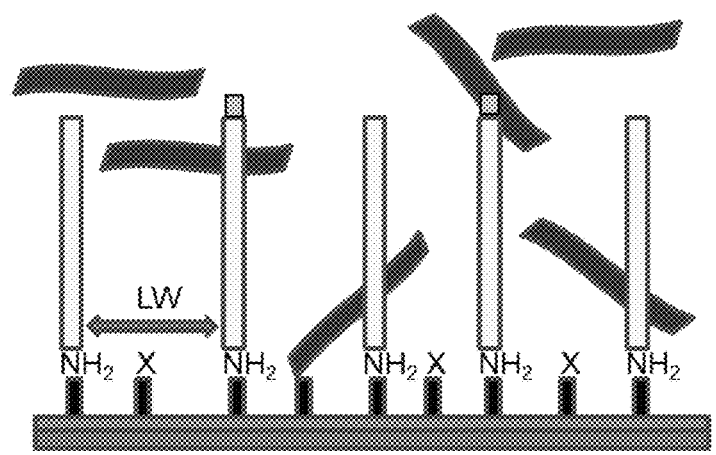

Microarray fabrication begins with application of a mixture of the chemically activatable surface, bifunctional polymer linkers and unmodified nucleic acid probes to the surface. The first step is reaction and covalent attachment of the bifunctional linker to the activated surface (FIG. 1B). In general, the chemical concentration of the bi-functional linker is set to be such that less than 100% of the reactive sites on the surface form a covalent linkage to the bi-functional linker. At such low density, the average distance between bi-functional linker molecules defines a spacing denoted lattice width ("LW" in FIG. 1B).

Figure 1C:
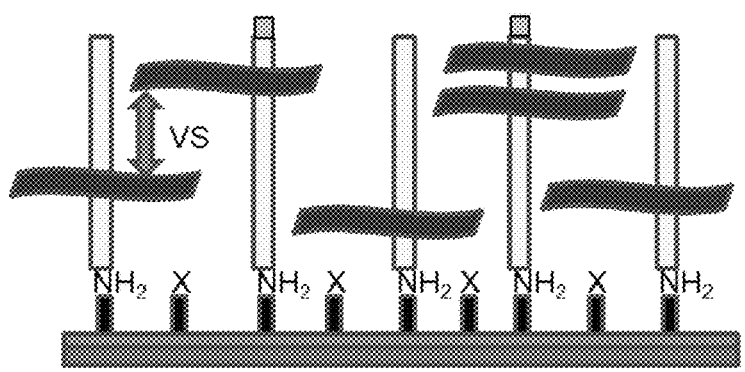

In the second step, the water in the solvent is evaporated to concentrate the DNA and bifunctional linker via evaporation of water from the solvent (FIG. 1C). Generally, use of pure water as the solvent during matrix fabrication is disadvantageous because water is quickly removed by evaporation due to a high surface area/volume ratio. To overcome this, in the present invention, a mixture of water with a high boiling point water-miscible solvent such as glycerin, DMSO or propanediol was used as solvent. In this case, upon evaporation, the water component will evaporate but not the high boiling point solvent. As a result, molecular reactants—DNA and bifunctional linker are progressively concentrated as the water is lost to evaporation. In the present invention, the ratio or water to high boiling point solvent is kept between 10:1 and 100:1. Thus, in the two extreme cases, upon equilibrium, volume of the fluid phase will reduce due to water evaporation to between $\frac{1}{100}$th and $\frac{1}{10}^{th}$ the original volume, thus giving rise to a 100-fold to 10-fold increase in reactant concentration. Such controlled evaporation is crucial to the present invention since it controls the vertical spacing (Vertical Separation, "VG" in FIG. 1C) between nucleic acid probes, which is inversely related to the extent of evaporative concentration.

Figure 1D:
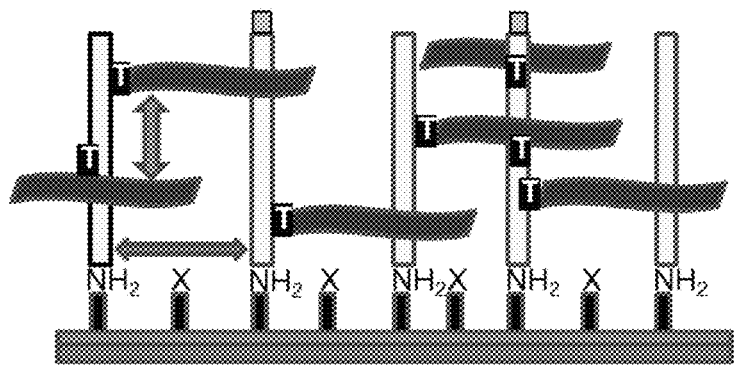

In the third step, the terminal Thymidine bases in the nucleic acid probes are UV crosslinked to the bifunctional linker within the evaporated surface (FIG. 1D). This process is mediated by the well-known photochemical reactivity of the Thymidine base that leads to the formation of covalent linkages to other thymidine bases in DNA or photochemical reaction with proteins and carbohydrates. If the bifunctional crosslinker is OligodT, then the crosslinking reaction will be bi-directional, that is, the photochemistry can be initiated in either the nucleic acid probe or the bifunctional OligodT linker. On the other hand, if the bifunctional linker is an amino polysaccharide such as chitosan or a polyamino acid, with a lysine or histidine in it, then the photochemistry will initiate in the nucleic acid probe, with the bifunctional linker being the target of the photochemistry.

Microarray System with Unmodified Solid Support for Non-Covalent Attachment

Figure 2A:
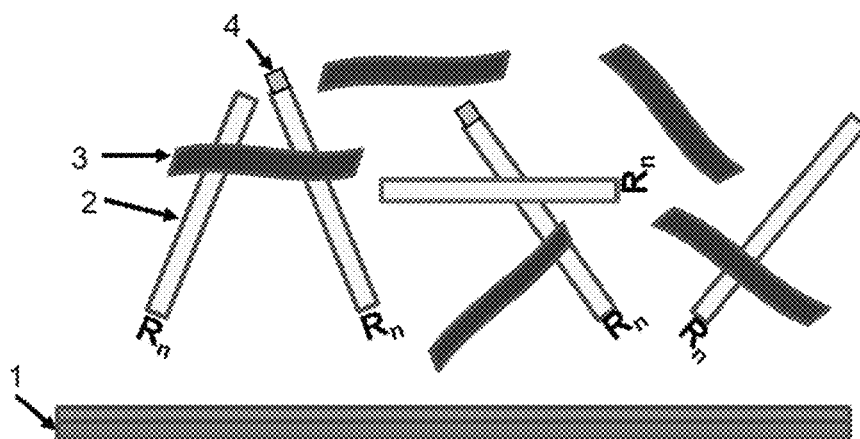
FIGS. 2A-2D illustrate an adsorptive microarray system comprising probes and bifunctional polymeric linkers.

In this microarray system, attachment of the nucleic acid probes does not occur to the underlying surface directly, but is instead mediated through a relatively long, bi-functional polymeric linker that binds non-covalently with the solid support, but covalently with the nucleic acid probes via UV-initiated crosslinking. The mechanics of this process is spontaneous 3D self assembly and is illustrated in FIGS. 2A-2D. As seen in FIG. 2A, the components required to fabricate this microarray system are:

(1) an unmodified nucleic acid probe 3 such as an oligonucleotide, PCR or isothermal amplicon, plasmid or genomic DNA;
(2) an unmodified solid support 1
(3) bifunctional polymer linkers 2 such as OligodT or a amino polysaccharide, amino polypeptide, that inherently have or are modified to have functional groups (designated "R") compatible for adsorptive binding to the solid support, each having a fluorescent label 4; and
(4) a solvent comprising water and a high boiling point, water-miscible liquid such as glycerol, DMSO or propanediol (water to solvent ratio between 10:1 and 100:1);

TABLE 2

Non-Covalent Attachment of Bi-Functional Polymeric Linker to an Inert Surface

| Representative support surface | Matched Adsorptive Group on Bifunctional Linker ($R_n$) | Specific Bifunctional polymeric linker |
|---|---|---|
| glass | Single Stranded Nucleic Acid > 10 bases | OligodT (30-60 bases) |
| glass | Amine-Polysaccharide | Chitosan (30-60 subunits) |
| glass | Extended Planar Hydrophobic Groups e.g. Digoxigenin | OligodT (30-60 bases)-5'-Digoxigenin |
| polycarbonate | Single Stranded Nucleic Acid > 10 bases | Oligo-dT (30-60 bases) |
| polycarbonate | Amine-Polysaccharide | Chitosan (30-60 subunits) |
| polycarbonate | Extended Planar Hydrophobic Groups e.g. Digoxigenin | OligodT (30-60 bases)-5'-Digoxigenin |
| graphene | Extended Planar Hydrophobic Groups e.g. pyrene | OligodT (30-60 bases)-5'pyrene |
| graphene | Extended Planar Hydrophobic Groups e.g. CY-5 dye | OligodT (30-60 bases)-5'-CY-5 dye |
| graphene | Extended Planar Hydrophobic | OligodT (30-60 bases)- |

TABLE 2-continued

Non-Covalent Attachment of Bi-Functional
Polymeric Linker to an Inert Surface

| Representative support surface | Matched Adsorptive Group on Bifunctional Linker ($R_n$) | Specific Bifunctional polymeric linker |
|---|---|---|
| gold | Extended Planar Hydrophobic Groups e.g. Digoxigenin | 5'-Digoxigenin OligodT (30-60 bases)-5'pyrene |
| gold | Extended Planar Hydrophobic Groups e.g. pyrene | OligodT (30-60 bases)-5' CY-5 dye |
| gold | Extended Planar Hydrophobic Groups e.g. CY-5 dye | OligodT (30-60 bases)-5' Digoxigenin |
| | Extended Planar Hydrophobic Groups e.g. Digoxigenin | |

Table 2 shows examples of unmodified support surfaces and matched absorptive groups on the bifunctional polymer linker for mere illustration purposes only and does not in any way precludes the use of other combinations of these.

When used in the present invention, components 1-3 are included as a solution to be applied to the solid support surface by ordinary methods of fabrication used to generate DNA Hybridization tests such as contact printing, piezo electric printing, ink jet printing, or pipetting.

Figure 2B:
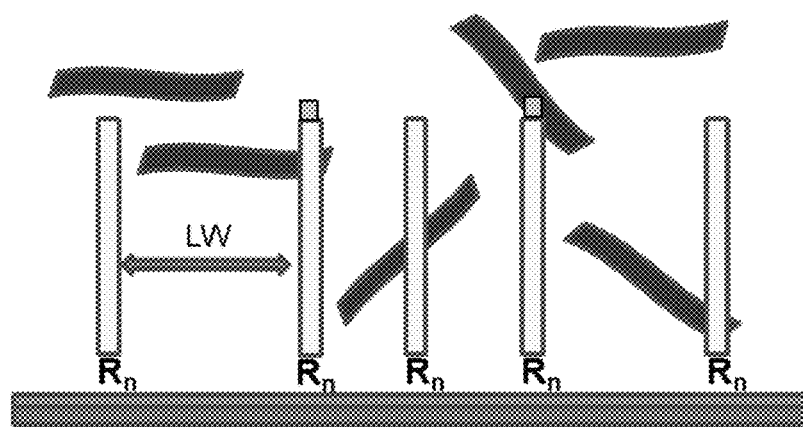

Microarray fabrication begins with application of a mixture of the components (1)-(3) to the surface. The first step is adsorption of the bifunctional linker to the support surface (FIG. 2B). The concentration of the bi-functional linker is set so the average distance between bi-functional linker molecules defines a spacing denoted as lattice width ("LW" in FIG. 2B).

Figure 2C:
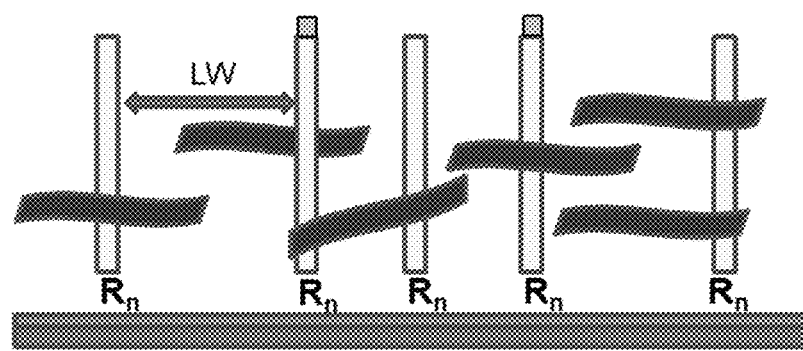

In the second step, the water in the solvent is evaporated to concentrate the DNA and bifunctional linker via evaporation of water from the solvent (FIG. 2C). Generally, use of pure water as the solvent during matrix fabrication is disadvantageous because water is quickly removed by evaporation due to a high surface area/volume ratio. To overcome this, in the present invention, a mixture of water with a high boiling point water-miscible solvent such as glycerin, DMSO or propanediol was used as solvent. In this case, upon evaporation, the water component will evaporate but not the high boiling point solvent. As a result, molecular reactants—DNA and bifunctional linker are progressively concentrated as the water is lost to evaporation. In the present invention, the ratio or water to high boiling point solvent is kept between 10:1 and 100:1. Thus, in the two extreme cases, upon equilibrium, volume of the fluid phase will reduce due to water evaporation to between $\frac{1}{100}$th and $\frac{1}{10}^{th}$ the original volume, thus giving rise to a 100-fold to 10-fold increase in reactant concentration.

Figure 2D:
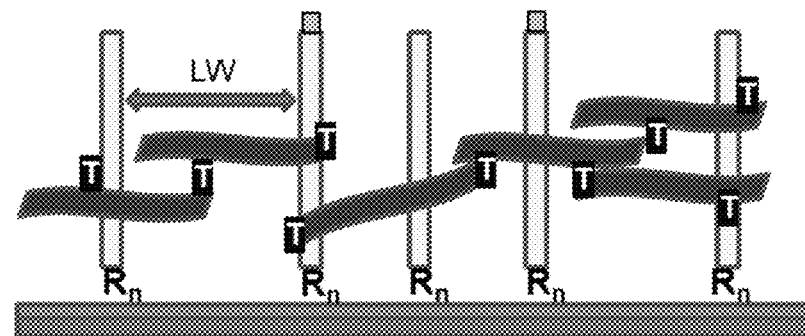

In the third step, the terminal Thymidine bases in the nucleic acid probes are UV crosslinked to the bifunctional linker within the evaporated surface (FIG. 2D). This process is mediated by the well-known photochemical reactivity of the Thymidine base that leads to the formation of covalent linkages to other thymidine bases in DNA or photochemical reaction with proteins and carbohydrates. If the bifunctional crosslinker is OligodT, then the crosslinking reaction will be bi-directional, that is, the photochemistry can be initiated in either the nucleic acid probe or the bifunctional OligodT linker. On the other hand, if the bifunctional linker is an amino polysaccharide such as chitosan or a polyamino acid, with a lysine or histidine in it, then the photochemistry will initiate in the nucleic acid probe, with the bifunctional linker being the target of the photochemistry.

Although such non-covalent adsorption described in the first step is generally weak and reversible, when occurring in isolation, in the present invention it is taught that if many such weak adsorptive events between the bifunctional polymeric linker and the underlying surface occur in close proximity, and if the closely packed polymeric linkers are subsequently linked to each other via Thymidine-mediated photochemical crosslinking, the newly created extended, multi-molecular (crosslinked) complex will be additionally stabilized on the surface, thus creating a stable complex with the surface in the absence of direct covalent bonding to that surface.

The present invention works efficiently for the linkage of synthetic oligonucleotides as nucleic acid probes to form a microarray-based hybridization device for the analysis of microbial DNA targets. However, it is clear that the same invention may be used to link PCR amplicons, synthetic oligonucleotides, isothermal amplification products, plasmid DNA or genomic DNA fragment as nucleic acid probes. It is also clear that the same technology could be used to manufacture hybridization devices that are not microarrays.

DNA nucleic acid probes were formulated as described in Table 3, to be deployed as described above and illustrated in FIG. 1 or FIG. 2. A set of 48 such probes (Table 4) were designed to be specific for various sequence determinants of microbial DNA and each was fabricated so as to present a string of 5-7 T bases at each end, to facilitate their UV-crosslinking to form a covalently linked microarray element, as described above and illustrated in FIG. 1. Each of the 48 different probes was printed in triplicate to form a 144 element (12×12) microarray having sequences shown in Table 3.

TABLE 3

Representative Conditions of use of the Present Invention

| | Unique sequence Oligonucleotide | 5' labelled OligodT Fluorescent marker 30 bases Long(marker) |
|---|---|---|
| Nucleic acid probe Type | 30-38 bases Long 7 T's at each end | |
| Nucleic acid probe Concentration | 50 mM | 0.15 mM |
| Bifunctional Linker | OligodT 30 bases long Primary amine at 3' terminus | |
| Bifunctional Linker Concentration | 1 mM | |
| High Boiling point Solvent | Water:Propanediol, 100:1 | |
| Surface | Epoxysilane on borosilicate glass | |
| UV Crosslinking Dose (mjoule) | 300 millijoule | |

TABLE 4

Nucleic acid probes Linked to the
Microarray Surface via the Present Invention

| SEQ ID NO: 132 | Negative control | TTTTTCTACTACCTATGCTGATTCACTCTTTTT |
| SEQ ID NO: 129 | Imager Calibration (High) | TTTTCTATGTATCGATGTTGAGAAATTTTTTT |
| SEQ ID NO: 130 | Imager Calibration (Low) | TTTTCTAGATACTTGTGTAAGTGAATTTTTTT |
| SEQ ID NO: 131 | Imager Calibration (Medium) | TTTTCTAAGTCATGTTGTTGAAGAATTTTTTT |
| SEQ ID NO: 126 | *Cannabis* ITS1 DNA Control 1 | TTTTTTAATCTGCGCCAAGGAACAATATTTTTT |
| SEQ ID NO: 127 | *Cannabis* ITS1 DNA Control 2 | TTTTTGCAATCTGCGCCAAGGAACAATATTTTTT |
| SEQ ID NO: 128 | *Cannabis* ITS1 DNA Control 3 | TTTATTTCTTGCGCCAAGGAACAATATTTTATTT |
| SEQ ID NO: 86 | Total Yeast and Mold (High sensitivity) | TTTTTTTTGAATCATCGARTCTTTGAACGCATTTTTTT |
| SEQ ID NO: 87 | Total Yeast and Mold (Low sensitivity) | TTTTTTTTGAATCATCGARTCTCCTTTTTTT |
| SEQ ID NO: 88 | Total Yeast and Mold (Medium sensitivity) | TTTTTTTTGAATCATCGARTCTTTGAACGTTTTTTT |
| SEQ ID NO: 132 | Negative control | TTTTTCTACTACCTATGCTGATTCACTCTTTTT |
| SEQ ID NO: 92 | *Aspergillus fumigatus* 1 | TTTCTTTTCGACACCCAACTTTATTTCCTTATTT |
| SEQ ID NO: 90 | *Aspergillus flavus* 1 | TTTTTTCGCAAATCAATCTTTTTCCAGTCTTTTT |
| SEQ ID NO: 95 | *Aspergillus niger* 1 | TTTTTTCGACGTTTTCCAACCATTTCTTTT |
| SEQ ID NO: 100 | *Botrytis* spp. | TTTTTTTCATCTCTCGTTACAGGTTCTCGGTTCTTTTTTT |
| SEQ ID NO: 108 | *Fusarium* spp. | TTTTTTTTAACACCTCGCRACTGGAGATTTTTTT |
| SEQ ID NO: 89 | *Alternaria* spp | TTTTTTCAAAGGTCTAGCATCCATTAAGTTTTTT |
| SEQ ID NO: 123 | *Rhodoturula* spp. | TTTTTTCTCGTTCGTAATGCATTAGCACTTTTTT |
| SEQ ID NO: 117 | *Penicillium paxilli* | TTTTTTCCCCTCAATCTTTAACCAGGCCTTTTTT |
| SEQ ID NO: 116 | *Penicillium oxalicum* | TTTTTTACACCATCAATCTTAACCAGGCCTTTTT |
| SEQ ID NO: 118 | *Penicillium* spp. | TTTTTTCAACCCAAATTTTTATCCAGGCCTTTTT |
| SEQ ID NO: 102 | *Candida* spp. Group 1 | TTTTTTTGTTTGGTGTTGAGCRATACGTATTTTT |
| SEQ ID NO: 103 | *Candida* spp. Group 2 | TTTTACTGTTTGGTAATGAGTGATACTCTCATTTT |
| SEQ ID NO: 124 | *Stachybotrys* spp | TTTCTTCTGCATCGGAGCTCAGCGCGTTTTATTT |
| SEQ ID NO: 125 | *Trichoderma* spp. | TTTTCCTCCTGCGCAGTAGTTTGCACATCTTTT |
| SEQ ID NO: 105 | *Cladosporium* spp. | TTTTTTTTGTGGAAACTATTCGCTAAAGTTTTTT |
| SEQ ID NO: 121 | *Podosphaera* spp. | TTTTTTTTAGTCAYGTATCTCGCGACAGTTTTTT |
| SEQ ID NO: 132 | Negative control | TTTTTCTACTACCTATGCTGATTCACTCTTTTT |
| SEQ ID NO: 37 | Total Aerobic bacteria (High) | TTTTTTTTTCCTACGGGAGGCAGTTTTTTT |
| SEQ ID NO: 38 | Total Aerobic bacteria (Medium) | TTTTTTTTCCCTACGGGAGGCATTTTTTTT |
| SEQ ID NO: 39 | Total Aerobic bacteria (Low) | TTTATTTTCCCTACGGGAGGCTTTTATTTT |
| SEQ ID NO: 47 | Bile-tolerant Gram-negative (High) | TTTTTCTATGCAGTCATGCTGTGTGTRTGTCTTTTT |

TABLE 4-continued

Nucleic acid probes Linked to the
Microarray Surface via the Present Invention

| SEQ ID NO: 48 | Bile-tolerant Gram-negative (Medium) | TTTTTCTATGCAGCCATGCTGTGTGTRTTTTTT |
| --- | --- | --- |
| SEQ ID NO: 49 | Bile-tolerant Gram-negative (Low) | TTTTTCTATGCAGTCATGCTGCGTGTRTTTTTT |
| SEQ ID NO: 53 | Coliform/Enterobacteriaceae | TTTTTTCTATTGACGTTACCCGCTTTTTT |
| SEQ ID NO: 81 | stx1 gene | TTTTTTCTTTCCAGGTACAACAGCTTTTTT |
| SEQ ID NO: 82 | stx2 gene | TTTTTTGCACTGTCTGAAACTGCCTTTTTT |
| SEQ ID NO: 59 | etuf gene | TTTTTTCCATCAAAGTTGGTGAAGAATCTTTTTT |
| SEQ ID NO: 132 | Negative control | TTTTTTCTACTACCTATGCTGATTCACTCTTTTT |
| SEQ ID NO: 65 | *Listeria* spp. | TTTTCTAAGTACTGTTGTTAGAGAATTTTT |
| SEQ ID NO: 56 | *Aeromonas* spp. | TTATTTTCTGTGACGTTACTCGCTTTTATT |
| SEQ ID NO: 78 | *Staphylococcus aureus* 1 | TTTATTTTCATATGTGTAAGTAACTGTTTTATTT |
| SEQ ID NO: 49 | *Campylobacter* spp. | TTTTTTATGACACTTTTCGGAGCTCTTTTT |
| SEQ ID NO: 72 | *Pseudomonas* spp. 3 | TTTATTTTAAGCACTTTAAGTTGGGATTTTATTT |
| SEQ ID NO: 53 | *Clostridium* spp. | TTTTCTGGAMGATAATGACGGTACAGTTTT |
| SEQ ID NO: 42 | *Escherichia coli*/Shigella 1 | TTTTCTAATACCTTTGCTCATTGACTCTTT |
| SEQ ID NO: 74 | *Salmonella enterica*/Enterobacter 1 | TTTTTTTGTTGTGGTTAATAACCGATTTTT |
| SEQ ID NO: 61 | invA gene | TTTTTTTATTGATGCCGATTTGAAGGCCTTTTTT |

The set of 48 different probes of Table 4 were formulated as described in Table 3, then printed onto epoxysilane coated borosilicate glass, using an Gentics Q-Array mini contact printer with Arrayit SMP pins, which deposit about 1 nL of formulation per spot. As described in FIG. 1, the arrays thus printed were then allowed to react with the epoxisilane surface at room temperature, and then evaporate to remove free water, also at room temperature. Upon completion of the evaporation step (typically overnight) the air-dried microarrays were then UV treated in a STATOLINKER® UV irradiation system: 300 mjoules of irradiation at 254 nm to initiate thymidine-mediated crosslinking. The microarrays are then ready for use, with no additional need for washing or capping.

Example 2

Using the 3-Dimensional Lattice Microarray System for DNA Analysis
Sample Processing
Harvesting Pathogens from plant surface comprises the following steps:

1. Wash the plant sample or tape pull in 1× phosphate buffered saline (PBS);
2. Remove plant material/tape;
3. Centrifuge to pellet cells and discard supernatant;
4. Resuspend in PathogenDx® Sample Prep Buffer premixed with Sample Digestion Buffer;
5. Heat at 55° C. for 45 minutes;
6. Vortex to dissipate the pellet;
7. Heat at 95° C. for 15 minutes; and
8. Vortex and centrifuge briefly before use in PCR.

Amplification by PCR

The sample used for amplification and hybridization analysis was a *Cannabis* flower wash from a licensed *Cannabis* lab. The washed flower material was then pelleted by centrifugation. The pellet was then digested with proteinase K, then spiked with a known amount of *Salmonella* DNA before PCR amplification.

TABLE 5

PCR Primers and PCR conditions used in amplification

PCR primers (P1) for PCR Reaction #1
Cannabis ITS1 1° FP*-
(SEQ ID NO: 17)
TTTGCAACAGCAGAACGACCCGTGA Cannabis ITS1 1° RP*-
(SEQ ID NO: 18)
TTTCGATAAACACGCATCTCGATTG Enterobacteriaceae 16S 1° FP-
(SEQ ID NO: 11)
TTACCTTCGGGCCTCTTGCCATCRGATGTG Enterobacteriaceae 16S 1° RP-
(SEQ ID NO: 12)
TTGGAATTCTACCCCCCTCTACRAGACTCAAGC PCR primers (P2) for PCR Reaction #2
Cannabis ITS1 2° FP-
(SEQ ID NO: 5)
TTTCGTGAACACGTTTTAAACAGCTTG Cannabis ITS1 2° RP-
(SEQ ID NO: 36)
(CY3)TTTCCACCGCACGAGCCACGCGAT Enterobacteriaceae 16S 2° FP-
(SEQ ID NO: 29)
TTATATTGCACAATGGGCGCAAGCCTGATG Enterobacteriaceae 16S 2° RP-
(SEQ ID NO: 30)
(CY3)TTTTGTATTACCGCGGCTGCTGGCA

| PCR Reagent | Primary PCR Concentration | Secondary PCR Concentration |
|---|---|---|
| PCR Buffer | 1X | 1X |
| $MgCl_2$ | 2.5 mM | 2.5 mM |
| BSA | 0.16 mg/mL | 0.16 mg/mL |
| dNTP's | 200 mM | 200 mM |
| Primer mix | 200 nM each | 50 nM-FP/ 200 nM RP |
| Taq Polymerase | 1.5 Units | 1.5 Units |

Program for PCR Reaction #1

| 95° C., 4 min | 98° C., 30s | 61° C., 30s 25X | 72° C., 60s | 72° C., 7 min |
|---|---|---|---|---|

Program for PCR Reaction #2

| 95° C., 4 min | 98° C., 20s | 61° C., 20s 25X | 72° C., 30s | 72° C., 7 min |
|---|---|---|---|---|

*FP, Forward Primer; *RP, Reverse Primer

The *Salmonella* DNA spiked sample was then amplified with PCR primers (P1-Table 5) specific for the 16s region of Enterobacteriaceae in a tandem PCR reaction to first isolate the targeted region (PCR Reaction #1) and also PCR primers (P1-Table 5) which amplify a segment of *Cannabis* DNA (ITS) used as a positive control.

The product of PCR Reaction #1 (1 μL) was then subjected to a second PCR reaction (PCR Reaction #2) which additionally amplified and labelled the two targeted regions (16s, ITS) with green CY3 fluorophore labeled primers (P2-Table 5). The product of the PCR Reaction #2 (504) was then diluted 1-1 with hybridization buffer (4×SSC+5×Denhardt's solution) and then applied directly to the microarray for hybridization.

Hybridization

Because the prior art method of microarray manufacture allows DNA to be analyzed via hybridization without the need for pre-treatment of the microarray surface, the use of the microarray is simple, and involves 6 manual or automated pipetting steps.

1) Pipette the amplified DNA+binding buffer onto the microarray
2) Incubate for 30 minutes to allow DNA binding to the microarray (typically at room temperature, RT)

3) Remove the DNA+binding buffer by pipetting
4) Pipette 50 uL of wash buffer onto the microarray (0.4×SSC+0.5×Denhardt's) and incubate 5 min at RT.
5) Remove the wash buffer by pipetting
6) Repeat steps 4 and 5
7) Perform image analysis at 532 nm and 635 nm to detect the probe spot location (532 nm) and PCR product hybridization (635 nm).

Image Analysis

Image Analysis was performed at two wavelengths (532 nm and 635 nm) on a raster-based confocal scanner: GenePix 4000B Microarray Scanner, with the following imaging conditions: 33% Laser power, 400 PMT setting at 532 nm/33% Laser Power, 700 PMT setting at 635 nm. FIG. 3 shows an example of the structure and hybridization performance of the microarray.

Figure 3A:
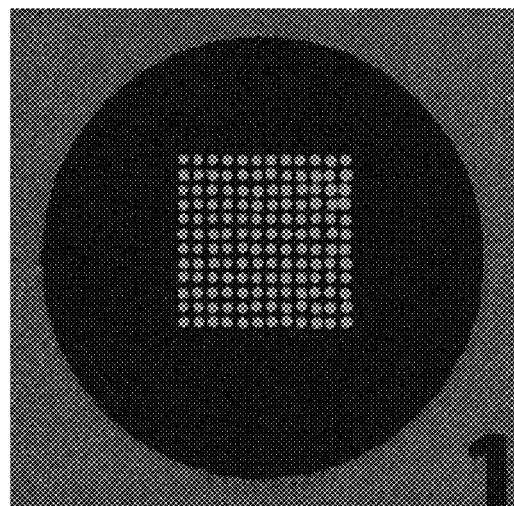
FIGS. 3A-3C show experimental data using the covalent microarray system. In this example of the invention the bifunctional polymeric linker was a chemically modified 40 base long oligo deoxythymidine (OligodT) having a CY5 fluorescent dye attached at its 5' terminus and an amino group attached at its 3' terminus, suitable for covalent linkage with a borosilicate glass solid support which had been chemically activated on its surface with epoxysilane. The nucleic acid probes comprised unmodified DNA oligonucleotides, suitable to bind to the solution state target, each oligonucleotide terminated with about 5 to 7 thymidines, to allow for photochemical crosslinking with the thymidines in the top domain of the polymeric (oligodT) linker.

FIG. 3A reveals imaging of the representative microarray, described above, after hybridization and washing, as visualized at 635 nm. The 635 nm image is derived from signals from the (red) CY5 fluor attached to the 5' terminus of the bifunctional polymer linker OligodT which had been introduced during microarray fabrication as a positional marker in each microarray spot (see FIG. 1 and Table 3). The data in FIG. 3A confirm that the CY5-labelled OligodT has been permanently linked to the microarray surface, via the combined activity of the bi-functional linker and subsequent UV-crosslinking, as described in FIG. 1.

Figure 3B:
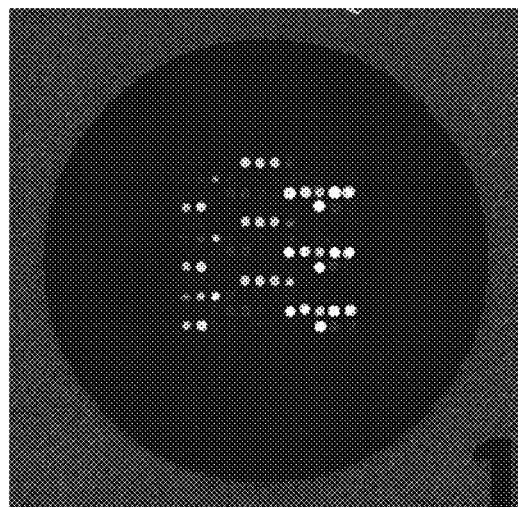

FIG. 3B reveals imaging of the representative microarray described above after hybridization and washing as visualized at 532 nm. The 532 nm image is derived from signals from the (green) CY3 fluor attached to the 5' terminus of PCR amplified DNA obtained during PCR Reaction #2. It is clear from FIG. 3B that only a small subset of the 48 discrete probes bind to the CY3-labelled PCR product, thus confirming that the present method of linking nucleic acid probes to form a microarray (FIG. 1) yields a microarray product capable of sequence specific binding to a (cognate) solution state target. The data in FIG. 3B reveal the underlying 3-fold repeat of the data (i.e., the array is the same set of 48 probes printed three times as 3 distinct sub-arrays to form the final 48×3=144 element microarray. The observation that the same set of 48 probes can be printed 3-times, as three repeated sub-domains show that the present invention generates microarray product that is reproducible.

Figure 3C:
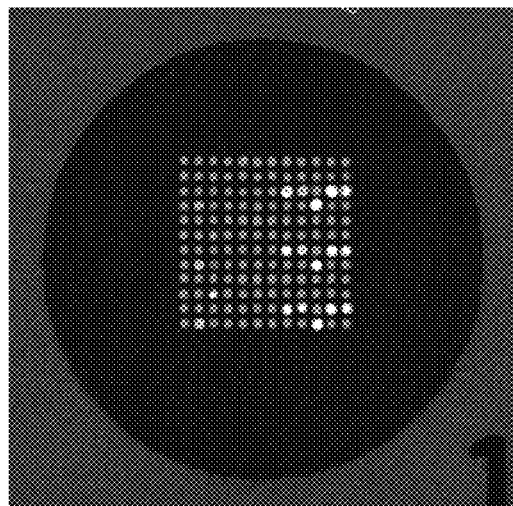

FIG. 3C reveals imaging of the representative microarray, described above, after hybridization and washing, as visualized with both the 532 nm and 635 nm images superimposed. The superimposed images display the utility of parallel attachment of a CY5-labelled OligodT positional marker relative to the sequence specific binding of the CY3-labelled PCR product.

Example 3

First PCR Amplification Step

Figure 4A:
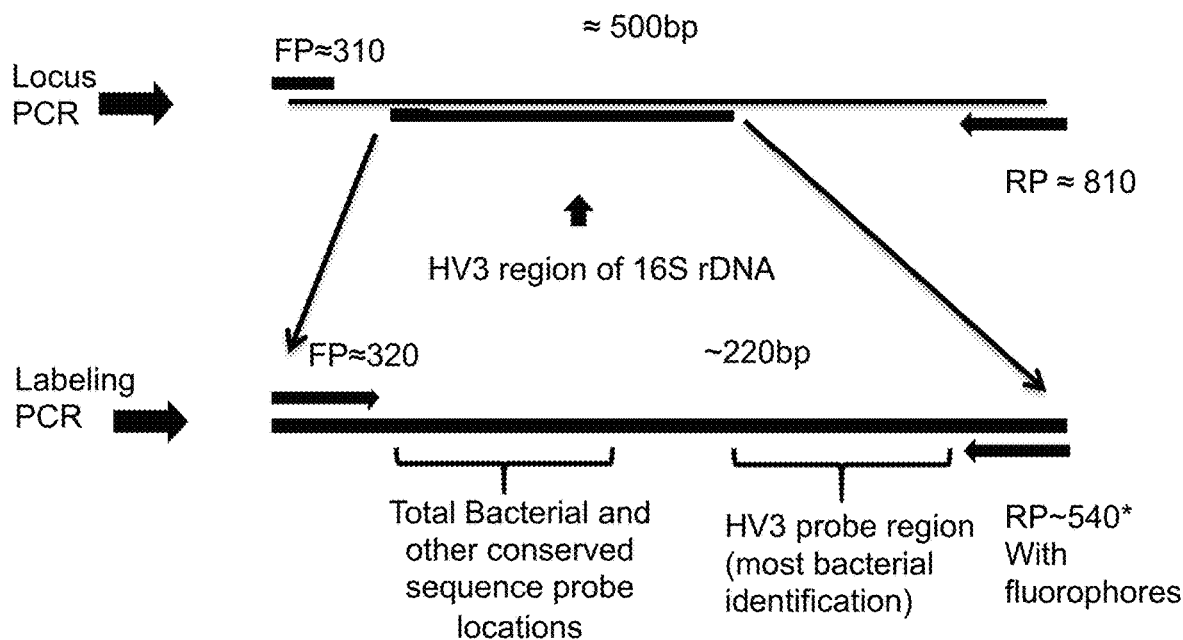
FIG. 4A is a graphical representation of the position of PCR primers employed within the 16s locus (all bacteria) to be used to PCR amplify unpurified bacterial contamination obtained from *Cannabis* wash and related plant wash. These PCR primers are used to amplify and dye label DNA from such samples for bacterial analysis via microarray hybridization.

FIG. 4A shows an exemplar of the first PCR step. As is standard, such PCR reactions are initiated by the administration of PCR Primers. Primers define the start and stopping point of the PCR based DNA amplification reaction. In this embodiment, a pair of PCR reactions is utilized to support the needed DNA amplification. In general, such PCR amplification is performed in series: a first pair of PCRs, with the suffix "P1" in FIG. 4A are used to amplify about 1 µL of any unpurified DNA sample, such as a raw *Cannabis* leaf wash for example. About 1 µL of the product of that first PCR reaction is used as the substrate for a second PCR reaction that is used to affix a fluorescent dye label to the DNA, so that the label may be used to detect the PCR product when it binds by hybridization to the microarray. The primer sequences for the first and second PCRs are shown in Table 6. The role of this two-step reaction is to avert the need to purify the pathogen DNA to be analyzed. The first PCR reaction, with primers "P1" is optimized to accommodate the raw starting material, while the second PCR primer pairs "P2" are optimized to obtain maximal DNA yield, plus dye labeling from the product of the first reaction. Taken in the aggregate, the sum of the two reactions obviates the need to either purify or characterize the pathogen DNA of interest.

FIG. 4A reveals at low resolution the 16s rDNA region which is amplified in an embodiment, to isolate and amplify a region which may be subsequently interrogated by hybridization. The DNA sequence of this 16s rDNA region is known to vary greatly among different bacterial species. Consequently, having amplified this region by two step PCR, that sequence variation may be interrogated by the subsequent microarray hybridization step.

TABLE 6

First and Second PCR Primers

| SEQ ID NO. | Primer target | Primer sequence |
|---|---|---|
| First PCR Primers (P1) for the first amplification step | | |
| SEQ ID NO: 1 | 16s rDNA HV3 Locus (Bacteria) | TTTCACAYTGGRACTGAGACACG |
| SEQ ID NO: 2 | 16s rDNA HV3 Locus (Bacteria) | TTTGACTACCAGGGTATCTAATCCTGT |
| SEQ ID NO: 3 | Stx1 Locus (Pathogenic *E. coli*) | TTTATAATCTACGGCTTATTGTTGAACG |
| SEQ ID NO: 4 | Stx1 Locus (Pathogenic *E. coli*) | TTTGGTATAGCTACTGTCACCAGACAATG |
| SEQ ID NO: 5 | Stx2 Locus (Pathogenic *E. coli*) | TTTGATGCATCCAGAGCAGTTCTGCG |
| SEQ ID NO: 6 | Stx2 Locus (Pathogenic *E. coli*) | TTTGTGAGGTCCACGTCTCCCGGCGTC |

TABLE 6-continued

First and Second PCR Primers

| SEQ ID NO. | Primer target | Primer sequence |
| --- | --- | --- |
| SEQ ID NO: 7 | InvA Locus (*Salmonella*) | TTTATTATCGCCACGTTCGGGCAATTCG |
| SEQ ID NO: 8 | InvA Locus (*Salmonella*) | TTTCTTCATCGCACCGTCAAAGGAACCG |
| SEQ ID NO: 9 | tuf Locus (All *E. coli*) | TTTCAGAGTGGGAAGCGAAAATCCTG |
| SEQ ID NO: 10 | tuf Locus (All *E. coli*) | TTTACGCCAGTACAGGTAGACTTCTG |
| SEQ ID NO: 11 | 16s rDNA *Enterobacteriaceae* HV3 Locus | TTACCTTCGGGCCTCTTGCCATCRGATGTG |
| SEQ ID NO: 12 | 16s rDNA *Enterobacteriaceae* HV3 Locus | TTGGAATTCTACCCCCCTCTACRAGACTCAAGC |
| SEQ ID NO: 13 | ITS2 Locus (All Yeast, Mold/Fungus) | TTTACTTTYAACAAYGGATCTCTTGG |
| SEQ ID NO: 14 | ITS2 Locus (All Yeast, Mold/Fungus) | TTTCTTTTCCTCCGCTTATTGATATG |
| SEQ ID NO: 15 | ITS2 Locus (*Aspergillus* species) | TTTAAAGGCAGCGGCGGCACCGCGTCCG |
| SEQ ID NO: 16 | ITS2 Locus (*Aspergillus* species) | TTTTCTTTTCCTCCGCTTATTGATATG |
| SEQ ID NO: 17 | ITS1 Locus (*Cannabis*/Plant) | TTTGCAACAGCAGAACGACCCGTGA |
| SEQ ID NO: 18 | ITS1 Locus (*Cannabis*/Plant) | TTTCGATAAACACGCATCTCGATTG |

Second PCR Primers (P2) for the second labeling amplification step

| SEQ ID NO. | Primer target | Primer sequence |
| --- | --- | --- |
| SEQ ID NO: 19 | 16s rDNA HV3 Locus (All Bacteria) | TTTACTGAGACACGGYCCARACTC |
| SEQ ID NO: 20 | 16s rDNA HV3 Locus (All Bacteria) | TTTGTATTACCGCGGCTGCTGGCA |
| SEQ ID NO: 21 | Stx1 Locus (Pathogenic *E. coli*) | TTTATGTGACAGGATTTGTTAACAGGAC |
| SEQ ID NO: 22 | Stx1 Locus (Pathogenic *E. coli*) | TTTCTGTCACCAGACAATGTAACCGCTG |
| SEQ ID NO: 23 | Stx2 Locus (Pathogenic *E. coli*) | TTTTGTCACTGTCACAGCAGAAG |
| SEQ ID NO: 24 | Stx2 Locus (Pathogenic *E. coli*) | TTTGCGTCATCGTATACACAGGAGC |
| SEQ ID NO: 25 | InvA Locus (All *Salmonella*) | TTTTATCGTTATTACCAAAGGTTCAG |
| SEQ ID NO: 26 | InvA Locus (All *Salmonella*) | TTTCCTTTCCAGTACGCTTCGCCGTTCG |
| SEQ ID NO: 27 | tuf Locus (All *E. coli*) | TTTGTTGTTACCGGTCGTGTAGAAC |
| SEQ ID NO: 28 | tuf Locus (All *E. coli*) | TTTCTTCTGAGTCTCTTTGATACCAACG |

TABLE 6-continued

First and Second PCR Primers

| SEQ ID NO. | Primer target | Primer sequence |
|---|---|---|
| SEQ ID NO: 29 | 16s rDNA Enterobacteriaceae HV3 Locus | TTATATTGCACAATGGGCGCAAGCCTGATG |
| SEQ ID NO: 30 | 16s rDNA Enterobacteriaceae HV3 Locus | TTTTGTATTACCGCGGCTGCTGGCA |
| SEQ ID NO: 31 | ITS2 Locus (All Yeast, Mold/Fungus) | TTTGCATCGATGAAGARCGYAGC |
| SEQ ID NO: 32 | ITS2 Locus (All Yeast, Mold/Fungus) | TTTCCTCCGCTTATTGATATGC |
| SEQ ID NO: 33 | ITS2 Locus (Aspergillus species) | TTTCCTCGAGCGTATGGGGCTTTGTC |
| SEQ ID NO: 34 | ITS2 Locus (Aspergillus species) | TITTTCCTCCGCTTATIGATATGC |
| SEQ ID NO: 35 | ITS1 Locus (Cannabis/Plant) | TTTCGTGAACACGTTTTAAACAGCTTG |
| SEQ ID NO: 36 | ITS1 Locus (Cannabis/Plant) | TTTCCACCGCACGAGCCACGCGAT |

Figure 4B:
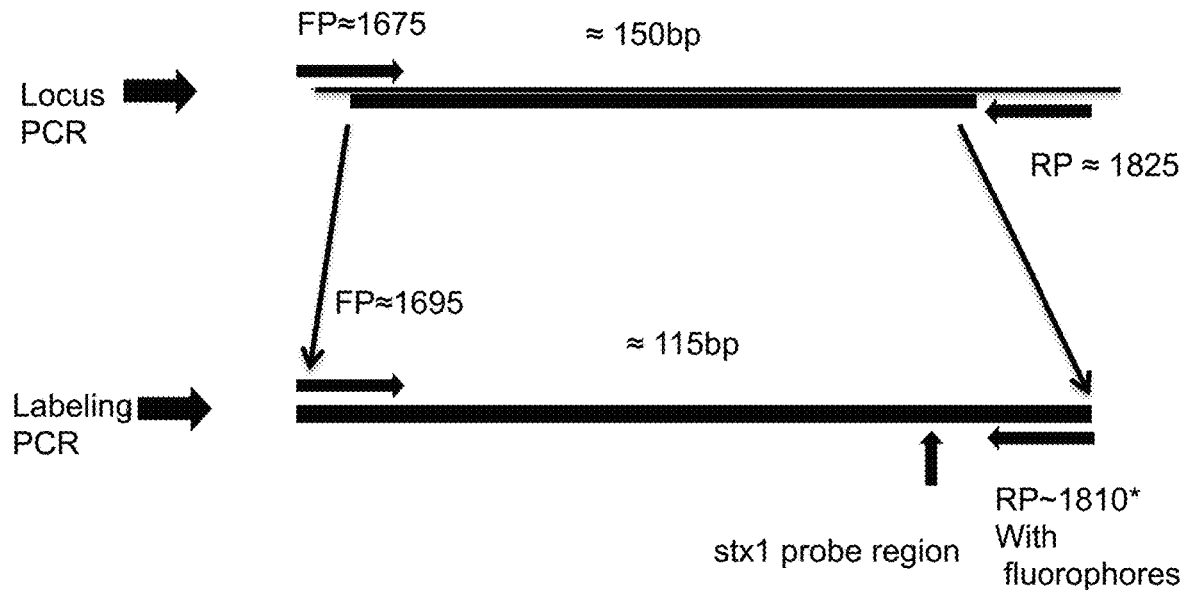
FIG. 4B is a graphical representation of the position of PCR primers employed within the stx1 locus (pathogenic *E. coli*) to be used to PCR amplify unpurified bacterial contamination obtained from *Cannabis* wash and related plant wash. These PCR primers are used to amplify and dye label DNA from such samples for bacterial analysis via microarray hybridization.

FIG. 4B displays the stx1 gene locus which is present in the most important pathogenic strains of *E coli* and which encodes Shigatoxin 1. Employing the same two-step PCR approach, a set of two PCR primer pairs were designed which, in tandem, can be used to amplify and label unprocessed bacterial samples to present the stx1 locus for analysis by microarray-based DNA hybridization.

Figure 5A:
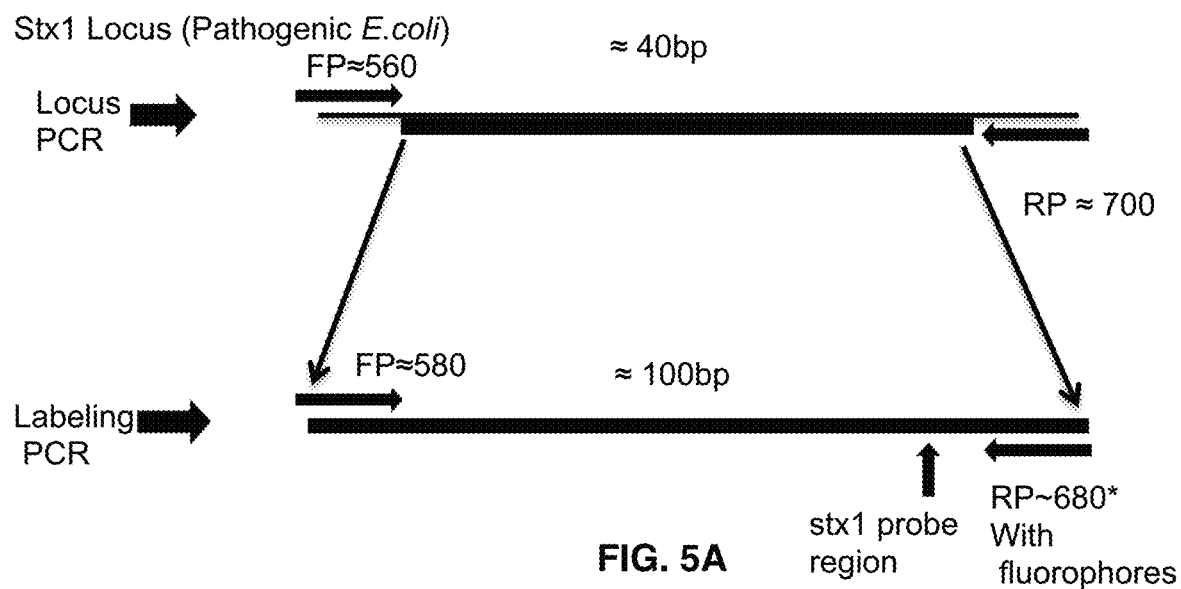
FIG. 5A is a graphical representation of the position of PCR primers employed as a two stage PCR reaction within the stx2 locus (pathogenic *E. coli*) to be used to PCR amplify unpurified bacterial contamination obtained from *Cannabis* wash and related plant wash. These PCR primers are used to amplify and dye label DNA from such samples for bacterial analysis via microarray hybridization.

FIG. 5A displays the stx2 gene locus which is also present in the most important pathogenic strains of *E coli* and which encodes Shigatoxin 2. Employing the same two-step PCR approach, a set of two PCR primer pairs were designed which, in tandem, can be used to amplify and label unprocessed bacterial samples so as to present the stx2 locus for analysis by microarray-based DNA hybridization.

Figure 5B:
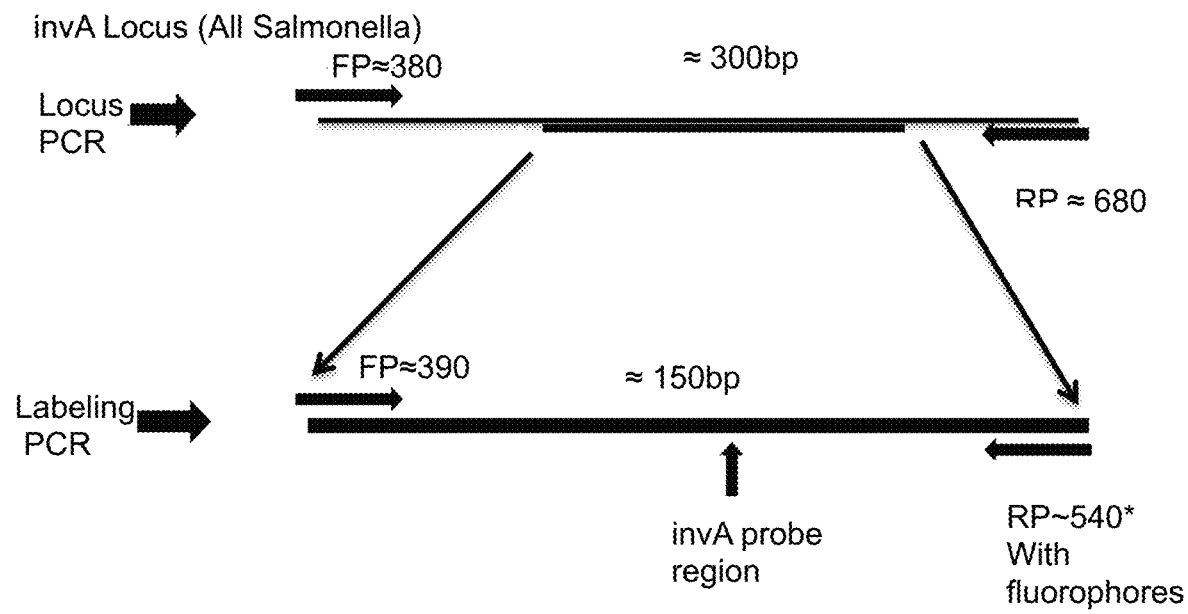
FIG. 5B is a graphical representation of the position of PCR primers employed within the invA locus (*Salmonella*) to be used to PCR amplify unpurified bacterial contamination obtained from *Cannabis* wash and related plant wash. These PCR primers are used to amplify and dye label DNA from such samples for bacterial analysis via microarray hybridization.

FIG. 5B displays the invA gene locus which is present in all strains of *Salmonella* and which encodes the InvAsion A gene product. Employing the same two-step PCR approach, a set of two PCR primer pairs were designed which, in tandem, can be used to amplify and label unprocessed bacterial samples so as to present the invA locus for analysis by microarray-based DNA hybridization.

Figure 6:
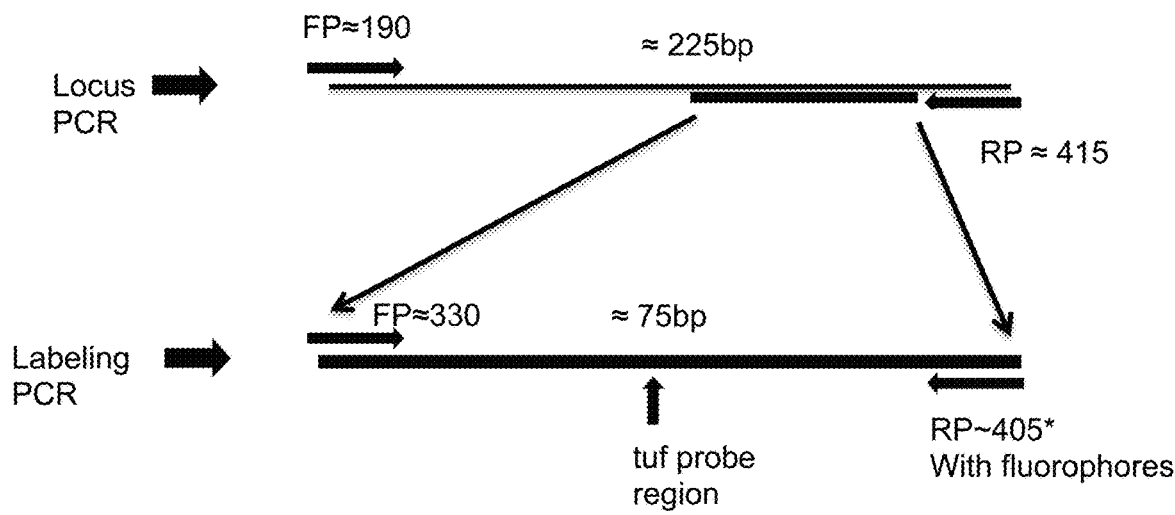
FIG. 6 is a graphical representation of the position of PCR primers employed within the tuf locus (*E. coli*) to be used to PCR amplify unpurified bacterial contamination obtained from *Cannabis* wash and related plant wash. These PCR primers are used to amplify and dye label DNA from such samples for bacterial analysis via microarray hybridization.

FIG. 6 displays the tuf gene locus which is present in all strains of *E coli* and which encodes the ribosomal elongation factor Tu. Employing the same two-step PCR approach, a set of two PCR primer pairs were designed which, in tandem, can be used to amplify and label unprocessed bacterial samples so as to present the tuf locus for analysis by microarray-based DNA hybridization.

Figure 7:
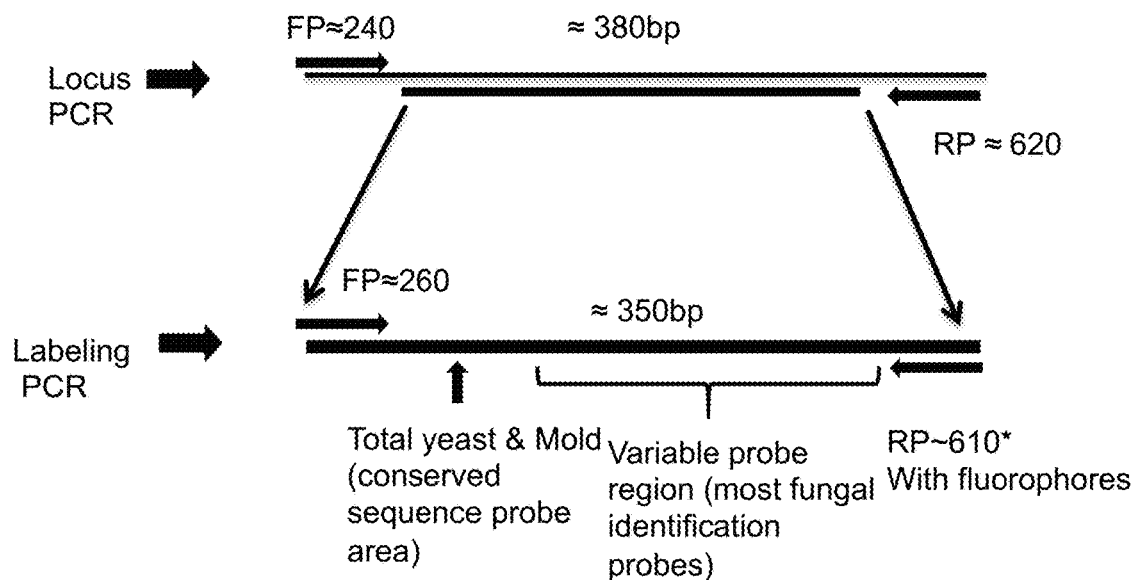
FIG. 7 is a graphical representation of the position of PCR primers employed within the ITS2 locus (yeast and mold) to be used to PCR amplify unpurified yeast, mold and fungal contamination obtained from *Cannabis* wash and related plant wash. These PCR primers are used to amplify and dye label DNA from such samples for yeast and mold analysis via microarray hybridization.

FIG. 7 displays the ITS2 locus which is present in all eukaryotes, including all strains of yeast and mold and which encodes the intergenic region between ribosomal genes 5.8S and 28S. ITS2 is highly variable in sequence and that sequence variation can be used to resolve strain differences in yeast, and mold. Employing the same two-step PCR approach, a set of two PCR primer pairs were designed which, in tandem, can be used to amplify and label unprocessed yeast and mold samples so as to present the ITS2 locus for analysis by microarray-based DNA hybridization.

Figure 8:
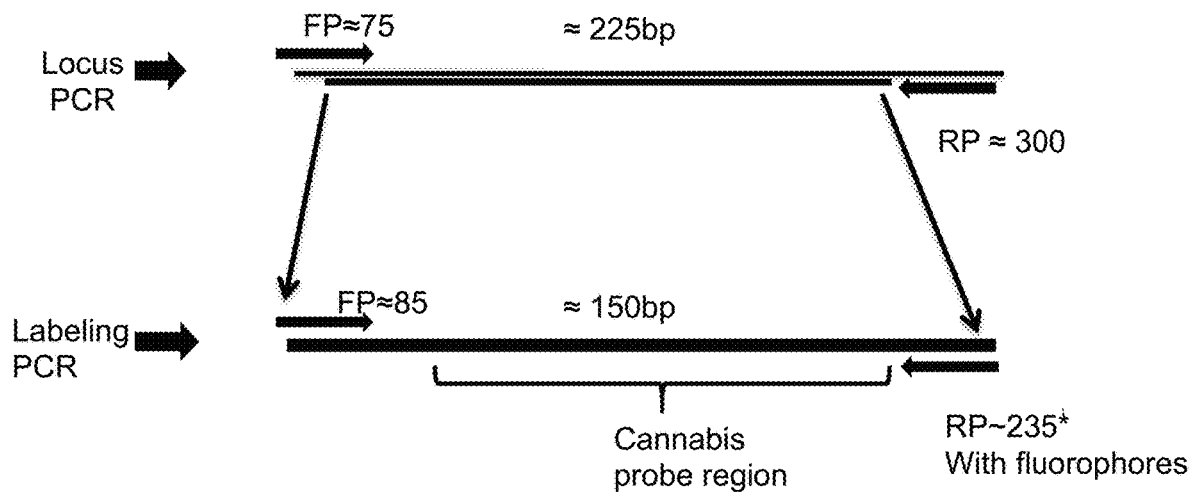
FIG. 8 is a graphical representation of the position of PCR primers employed within the ITS1 locus (*Cannabis* Plant Control) to be used to PCR amplify unpurified DNA obtained from *Cannabis* wash. These PCR primers are used to amplify and dye label DNA from such samples for DNA analysis via microarray hybridization. This PCR reaction is used to generate an internal plant host control signal, via hybridization, to be used to normalize bacterial, yeast, mold and fungal signals obtained by microarray analysis on the same microarray.

FIG. 8 displays the ITS1 gene locus which is present in all eukaryotes, including all plants and animals, which encodes the intergenic region between ribosomal genes 18S and 5.8S. ITS1 is highly variable in sequence among higher plants and that sequence variation can be used to identify plant species. Employing the same two-step PCR approach, a set of two PCR primer pairs were designed which, in tandem, can be used to amplify and label unprocessed *Cannabis* samples so as to present the ITS1 locus for analysis by microarray-based DNA hybridization. The identification and quantitation of the *Cannabis* sequence variant of ITS1 is used as an internal normalization standard in the analysis of pathogens recovered from the same *Cannabis* samples.

Table 7 displays representative oligonucleotide sequences which are used as microarray probes in an embodiment for DNA microarray-based analysis of bacterial 16s locus as described in FIG. 4. The sequence of those probes has been varied to accommodate the cognate sequence variation which occurs as a function of species difference among bacteria. In all cases, the probe sequences are terminated with a string of T's at each end, to enhance the efficiency of probe attachment to the microarray surface, at time of microarray manufacture. Table 8 shows sequences of the Calibration and Negative controls used in the microarray.

Table 9 displays representative oligonucleotide sequences which are used as microarray probes in an embodiment for DNA microarray-based analysis of eukaryotic pathogens (fungi, yeast and mold) based on their ITS2 locus as described in FIG. 7. Sequences shown in Table 8 are used as controls. The sequence of those probes has been varied to accommodate the cognate sequence variation which occurs as a function of species difference among fungi, yeast and mold. In all cases, the probe sequences are terminated with a string of T's at each end, to enhance the efficiency of probe attachment to the microarray surface, at time of microarray manufacture.

Table 10 displays representative oligonucleotide sequences which are used as microarray probes in an embodiment for DNA microarray-based analysis of *Cannabis* at the ITS1 locus (*Cannabis* spp.).

TABLE 7

| | Oligonucleotide probe sequence for the 16S Locus | |
|---|---|---|
| SEQ ID NO: 37 | Total Aerobic bacteria (High) | TTTTTTTTTCCTACGGGAGGCAGTTTTTTT |
| SEQ ID NO: 38 | Total Aerobic bacteria (Medium) | TTTTTTTTCCCTACGGGAGGCATTTTTTTT |
| SEQ ID NO: 39 | Total Aerobic bacteria (Low) | TTTATTTTCCCTACGGGAGGCTTTTATTTT |
| SEQ ID NO: 40 | *Enterobacteriaceae* (Low sensitivity) | TTTATTCTATTGACGTTACCCATTTATTTT |
| SEQ ID NO: 41 | *Enterobacteriaceae* (Medium sensitivity) | TTTTTTCTATTGACGTTACCCGTTTTTTTT |
| SEQ ID NO: 42 | *Escherichia coli/ Shigella* 1 | TTTTCTAATACCTTTGCTCATTGACTCTTT |
| SEQ ID NO: 43 | *Escherichia coli/ Shigella* 2 | TTTTTTAAGGGAGTAAAGTTAATATTTTTT |
| SEQ ID NO: 44 | *Escherichia coli/ Shigella* 3 | TTTTCTCCTTTGCTCATTGACGTTATTTTT |
| SEQ ID NO: 45 | *Bacillus* spp. Group1 | TTTTTCAGTTGAATAAGCTGGCACTCTTTT |
| SEQ ID NO: 46 | *Bacillus* spp. Group2 | TTTTTTCAAGTACCGTTCGAATAGTTTTTT |
| SEQ ID NO: 47 | Bile-tolerant Gram- negative (High) | TTTTTCTATGCAGTCATGCTGTGTGTRTGTCTT TTT |
| SEQ ID NO: 48 | Bile-tolerant Gram- negative (Medium) | TTTTTCTATGCAGCCATGCTGTGTGTRTTTTTTT |
| SEQ ID NO: 49 | Bile-tolerant Gram- negative (Low) | TTTTTCTATGCAGTCATGCTGCGTGTRTTTTTTT |
| SEQ ID NO: 50 | *Campylobacter* spp. | TTTTTTATGACACTTTTCGGAGCTCTTTTT |
| SEQ ID NO: 51 | *Chromobacterium* spp. | TTTTATTTTCCCGCTGGTTAATACCCTTTATTTT |
| SEQ ID NO: 52 | *Citrobacter* spp. Group1 | TTTTTTCCTTAGCCATTGACGTTATTTTTT |
| SEQ ID NO: 53 | *Clostridium* spp. | TTTTCTGGAMGATAATGACGGTACAGTTTT |
| SEQ ID NO: 54 | Coliform/*Entero- bacteriaceae* | TTTTTTCTATTGACGTTACCCGCTTTTTTT |
| SEQ ID NO: 55 | *Aeromonas salmonicida/hydrophilia* | TTTTTGCCTAATACGTRTCAACTGCTTTTT |
| SEQ ID NO: 56 | *Aeromonas* spp. | TTATTTTCTGTGACGTTACTCGCTTTTATT |
| SEQ ID NO: 57 | *Alkanindiges* spp. | TTTTTAGGCTACTGRTACTAATATCTTTTT |
| SEQ ID NO: 58 | *Bacillus pumilus* | TTTATTTAAGTGCRAGAGTAACTGCTATTTTATT |
| SEQ ID NO: 59 | etuf gene | TTTTTTCCATCAAAGTTGGTGAAGAATCTTTTTT |
| SEQ ID NO: 60 | *Hafnia* spp. | TTTTTTCTAACCGCAGTGATTGATCTTTTT |
| SEQ ID NO: 61 | invA gene | TTTTTTTATTGATGCCGATTTGAAGGCCTTTTTT |
| SEQ ID NO: 62 | *Klebsiella oxytoca* | TTTTTTCTAACCTTATTCATTGATCTTTTT |
| SEQ ID NO: 63 | *Klebsiella pneumoniae* | TTTTTTCTAACCTTGGCGATTGATCTTTTT |
| SEQ ID NO: 64 | *Legionella* spp. | TTTATTCTGATAGGTTAAGAGCTGATCTTTATTT |
| SEQ ID NO: 65 | *Listeria* spp. | TTTTCTAAGTACTGTTGTTAGAGAATTTTT |

TABLE 7-continued

Oligonucleotide probe sequence for the 16S Locus

| SEQ ID NO: 66 | Panteoa agglomerans | TTTTTTAACCCTGTCGATTGACGCCTTTTT |
| --- | --- | --- |
| SEQ ID NO: 67 | Panteoa stewartii | TTTTTTAACCTCATCAATTGACGCCTTTTT |
| SEQ ID NO: 68 | Pseudomonas aeruginosa | TTTTTGCAGTAAGTTAATACCTTGTCTTTTT |
| SEQ ID NO: 69 | Pseudomonas cannabina | TTTTTTTACGTATCTGTTTTGACTCTTTTT |
| SEQ ID NO: 70 | Pseudomonas spp. 1 | TTTTTTGTTACCRACAGAATAAGCATTTTT |
| SEQ ID NO: 71 | Pseudomonas spp. 2 | TTTTTTAAGCACTTTAAGTTGGGATTTTTT |
| SEQ ID NO: 72 | Pseudomonas spp. 3 | TTTATTTTAAGCACTTTAAGTTGGGATTTTATTT |
| SEQ ID NO: 73 | Salmonella bongori | TTTTTTTAATAACCTTGTTGATTGTTTTTT |
| SEQ ID NO: 74 | Salmonella enterica/Enterobacter 1 | TTTTTTTGTTGTGGTTAATAACCGATTTTT |
| SEQ ID NO: 75 | Salmonella enterica/Enterobacter 2 | TTTTTTTAACCGCAGCAATTGACTCTTTTT |
| SEQ ID NO: 76 | Salmonella enterica/Enterobacter 3 | TTTTTTCTGTTAATAACCGCAGCTTTTTTT |
| SEQ ID NO: 77 | Serratia spp. | TTTATTCTGTGAACTTAATACGTTCATTTTTATT |
| SEQ ID NO: 78 | Staphylococcus aureus 1 | TTTATTTTCATATGTGTAAGTAACTGTTTTATTT |
| SEQ ID NO: 79 | Staphylococcus aureus 2 | TTTTTTCATATGTGTAAGTAACTGTTTTTT |
| SEQ ID NO: 80 | Streptomyces spp. | TTTTATTTTAAGAAGCGAGAGTGACTTTATTTT |
| SEQ ID NO: 81 | stx1 gene | TTTTTTCTTTCCAGGTACAACAGCTTTTTT |
| SEQ ID NO: 82 | stx2 gene | TTTTTTGCACTGTCTGAAACTGCCTTTTTT |
| SEQ ID NO: 83 | Vibrio spp. | TTTTTTGAAGGTGGTTAAGCTAATTTTTTT |
| SEQ ID NO: 84 | Xanthamonas spp. | TTTTTTGTTAATACCCGATTGTTCTTTTTT |
| SEQ ID NO: 85 | Yersinia pestis | TTTTTTTGAGTTTAATACGCTCAACTTTTT |

TABLE 8

Calibration and Negative Controls

| SEQ ID NO: 129 | Imager Calibration (High) | TTTTCTATGTATCGATGTTGAGAAATTTTTT |
| --- | --- | --- |
| SEQ ID NO: 130 | Imager Calibration (Low) | TTTTCTAGATACTTGTGTAAGTGAATTTTTT |
| SEQ ID NO: 131 | Imager Calibration (Medium) | TTTTCTAAGTCATGTTGTTGAAGAATTTTTT |
| SEQ ID NO: 132 | Negative control | TTTTTTCTACTACCTATGCTGATTCACTCTTTTT |

TABLE 9

Oligonucleotide probe sequence for the ITS2 Locus

| SEQ ID NO: 86 | Total Yeast and Mold (High sensitivity) | TTTTTTTTGAATCATCGARTCTTTGAACGCATTTTTT |
| --- | --- | --- |
| SEQ ID NO: 87 | Total Yeast and Mold (Low sensitivity) | TTTTTTTTGAATCATCGARTCTCCTTTTTT |

TABLE 9-continued

Oligonucleotide probe sequence for the ITS2 Locus

| SEQ ID NO: 88 | Total Yeast and Mold (Medium sensitivity) | TTTTTTTTGAATCATCGARTCTTTGAACGTTTTTTT |
| --- | --- | --- |
| SEQ ID NO: 89 | Alternaria spp. | TTTTTTCAAAGGTCTAGCATCCATTAAGTTTTTT |
| SEQ ID NO: 90 | Aspergillus flavus 1 | TTTTTTCGCAAATCAATCTTTTTCCAGTCTTTTT |
| SEQ ID NO: 91 | Aspergillus flavus 2 | TTTTTTTCTTGCCGAACGCAAATCAATCTTTTTTTTTTT |
| SEQ ID NO: 92 | Aspergillus fumigatus 1 | TTTCTTTTCGACACCCAACTTTATTTCCTTATTT |
| SEQ ID NO: 93 | Aspergillus fumigatus 2 | TTTTTTTGCCAGCCGACACCCATTCTTTTT |
| SEQ ID NO: 94 | Aspergillus nidulans | TTTTTTGGCGTCTCCAACCTTACCCTTTTT |
| SEQ ID NO: 95 | Aspergillus niger 1 | TTTTTTCGACGTTTTCCAACCATTTCTTTT |
| SEQ ID NO: 96 | Aspergillus niger 2 | TTTTTTTTCGACGTTTTCCAACCATTTCTTTTTT |
| SEQ ID NO: 97 | Aspergillus niger 3 | TTTTTTTCGCCGACGTTTTCCAATTTTTTT |
| SEQ ID NO: 98 | Aspergillus terreus | TTTTTCGACGCATTTATTTGCAACCCTTTT |
| SEQ ID NO: 99 | Blumeria | TTTATTTGCCAAAAMTCCTTAATTGCTCTTTTTT |
| SEQ ID NO: 100 | Botrytis spp | TTTTTTTCATCTCTCGTTACAGGTTCTCGGTTCTTTTTTT |
| SEQ ID NO: 101 | Candida albicans | TTTTTTTTGAAAGACGGTAGTGGTAAGTTTTTT |
| SEQ ID NO: 102 | Candida spp. Group 1 | TTTTTTTGTTTGGTGTTGAGCRATACGTATTTTT |
| SEQ ID NO: 103 | Candida spp. Group 2 | TTTTACTGTTTGGTAATGAGTGATACTCTCATTTT |
| SEQ ID NO: 104 | Chaetomium spp. | TTTCTTTTGGTTCCGGCCGTTAAACCATTTTTTT |
| SEQ ID NO: 105 | Cladosporium spp | TTTTTTTTGTGGAAACTATTCGCTAAAGTTTTTT |
| SEQ ID NO: 106 | Erysiphe spp. | TTTCTTTTTACGATTCTCGCGACAGAGTTTTTTT |
| SEQ ID NO: 107 | Fusarium oxysporum | TTTTTTTCTCGTTACTGGTAATCGTCGTTTTTTT |
| SEQ ID NO: 108 | Fusarium spp | TTTTTTTTAACACCTCGCRACTGGAGATTTTTTT |
| SEQ ID NO: 109 | Golovinomyces | TTTTTTCCGCTTGCCAATCAATCCATCTCTTTTT |
| SEQ ID NO: 110 | Histoplasma capsulatum | TTTATTTTGTCGAGTTCCGGTGCCCTTTTATTT |
| SEQ ID NO: 111 | Isaria spp. | TTTATTTTCCGCGGCGACCTCTGCTCTTTATTT |
| SEQ ID NO: 112 | Monocillium spp. | TTTCTTTTGAGCGACGACGGGCCCAATTTTCTTT |
| SEQ ID NO: 113 | Mucor spp. | TTTTCTCCAVVTGAGYACGCCTGTTTCTTTT |
| SEQ ID NO: 114 | Myrothecium spp. | TTTATTTTCGGTGGCCATGCCGTTAAATTTTATT |

TABLE 9-continued

Oligonucleotide probe sequence for the ITS2 Locus

| | | | |
|---|---|---|---|
| SEQ ID NO: 115 | Oidiodendron spp. | | TTTTTTTGCGTAGTACATCTCTCGCTCATTTTTT |
| SEQ ID NO: 116 | Penicillium oxalicum | | TTTTTTACACCATCAATCTTAACCAGGCCTTTTT |
| SEQ ID NO: 117 | Penicillium paxilli | | TTTTTTCCCCTCAATCTTTAACCAGGCCTTTTTT |
| SEQ ID NO: 118 | Penicillium spp | | TTTTTTCAACCCAAATTTTTATCCAGGCCTTTTT |
| SEQ ID NO: 119 | Phoma/ Epicoccum spp. | | TTTTTTTGCAGTACATCTCGCGCTTTGATTTTTT |
| SEQ ID NO: 120 | Podosphaera spp | | TTTTTTGACCTGCCAAAACCCACATACCATTTTT |
| SEQ ID NO: 121 | Podosphaera spp. | | TTTTTTTTAGTCAYGTATCTCGCGACAGTTTTTT |
| SEQ ID NO: 122 | Pythium oligandrum | | TTTTATTTAAAGGAGACAACACCAATTTTTATTT |
| SEQ ID NO: 123 | Rhodoturula spp | | TTTTTTCTCGTTCGTAATGCATTAGCACTTTTTT |
| SEQ ID NO: 124 | Stachybotrys spp | | TTTCTTCTGCATCGGAGCTCAGCGCGTTTTATTT |
| SEQ ID NO: 125 | Trichoderma spp | | TTTTTCCTCCTGCGCAGTAGTTTGCACATCTTTT |

Table 11 displays representative oligonucleotide sequences which are used as microarray probes in an embodiment for DNA microarray-based analysis of bacterial pathogens (stx1, stx2, invA, tuf) and for DNA analysis of the presence host Cannabis at the ITS1 locus (Cannabis spp.). It should be noted that this same approach, with modifications to the ITS1 sequence, could be used to analyze the presence of other plant hosts in such extracts.

TABLE 10

Oligonucleotide probe sequence for the Cannabis ITS1 Locus

| | | |
|---|---|---|
| SEQ ID NO: 126 | Cannabis ITS1 DNA Control 1 | TTTTTTAATCTGCGCCA AGGAACAATATTTTTTT |
| SEQ ID NO: 127 | Cannabis ITS1 DNA Control 2 | TTTTTGCAATCTGCGCC AAGGAACAATATTTTTT |
| SEQ ID NO: 128 | Cannabis ITS1 DNA Control 3 | TTTATTTCTTGCGCCAA GGAACAATATTTTATTT |

TABLE 11

Representative Microarray Probe Design for the Present Invention: Bacterial Toxins, ITS1 (Cannabis)

| | | |
|---|---|---|
| SEQ ID NO: 81 | stx1 gene | TTTTTTCTTTCCAGGTA CAACAGCTTTTTT |
| SEQ ID NO: 82 | stx2 gene | TTTTTTGCACTGTCTGA AACTGCCTTTTTT |
| SEQ ID NO: 59 | etuf gene | TTTTTTCCATCAAAGTT GGTGAAGAATCTTTTTT |

TABLE 11-continued

Representative Microarray Probe Design for the Present Invention: Bacterial Toxins, ITS1 (Cannabis)

| | | |
|---|---|---|
| SEQ ID NO: 61 | invA gene | TTTTTTTATTGATGCCG ATTTGAAGGCCTTTTTT |
| SEQ ID NO: 126 | Cannabis ITS1 DNA Control 1 | TTTTTTAATCTGCGCCA AGGAACAATATTTTTTT |

Figure 9:
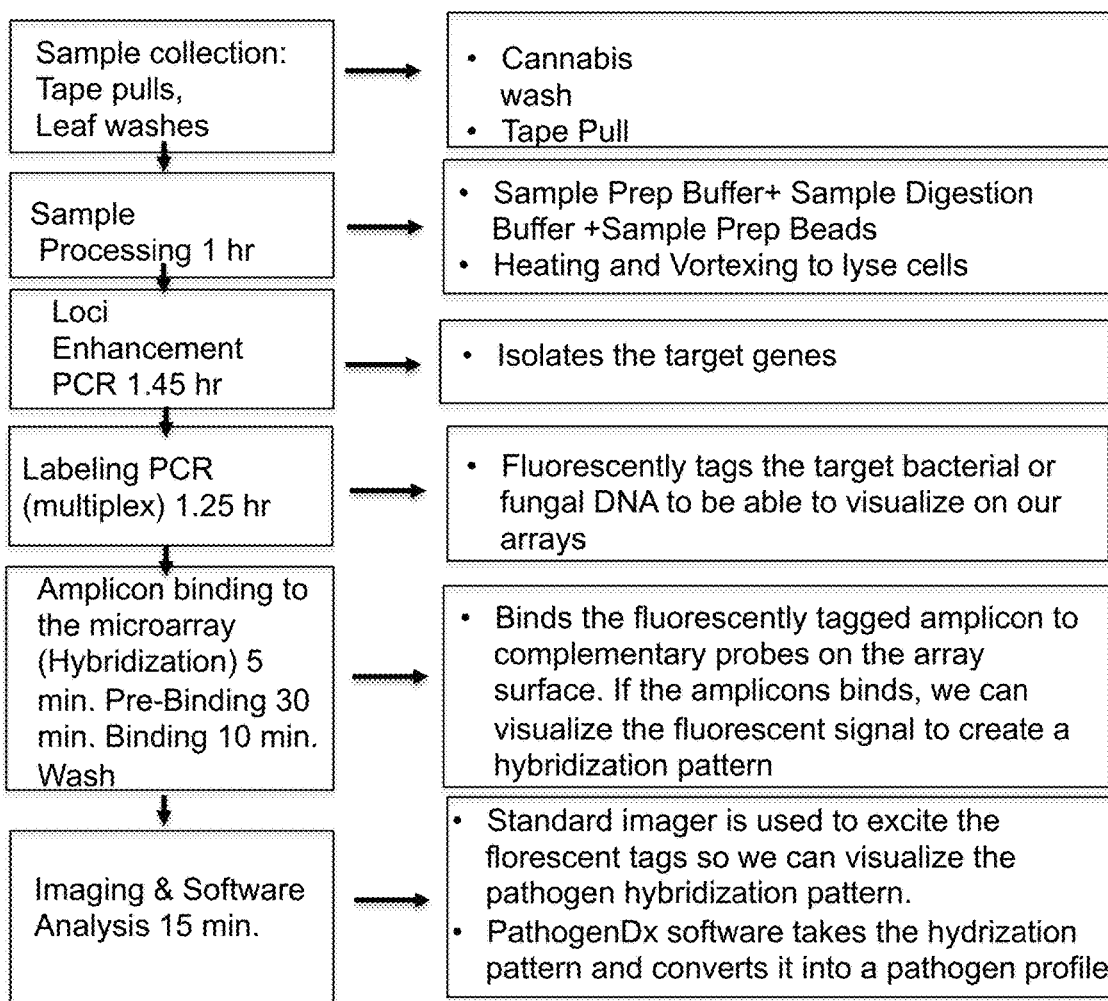
FIG. 9 is a flow diagram illustrating the processing of unpurified *Cannabis* wash or other surface sampling from *Cannabis* (and related plant material) so as to PCR amplify the raw *Cannabis* or related plant material, and then to perform microarray analysis on that material so as to analyze the pathogen complement of those plant samples

FIG. 9 shows a flow diagram to describe how an embodiment is used to analysis the bacterial pathogen or yeast and mold complement of a Cannabis or related plant sample. Pathogen samples can be harvested from Cannabis plant material by tape pulling of surface bound pathogen or by simple washing of the leaves or buds or stems, followed by a single multiplex "Loci Enhancement" Multiplex PCR reaction, which is then followed by a single multiplex "Labelling PCR". A different pair of two step PCR reactions is used to analyze bacteria, than the pair of two step PCR reactions used to analyze fungi, yeast and mold. In all cases, the DNA of the target bacteria or fungi, yeast and mold are PCR amplified without extraction or characterization of the DNA prior to two step PCR. Subsequent to the Loci Enhancement and Labelling PCR steps, the resulting PCR product is simply diluted into binding buffer and then applied to the microarray test. The subsequent microarray steps required for analysis (hybridization and washing) are performed at lab ambient temperature.

Figure 10:
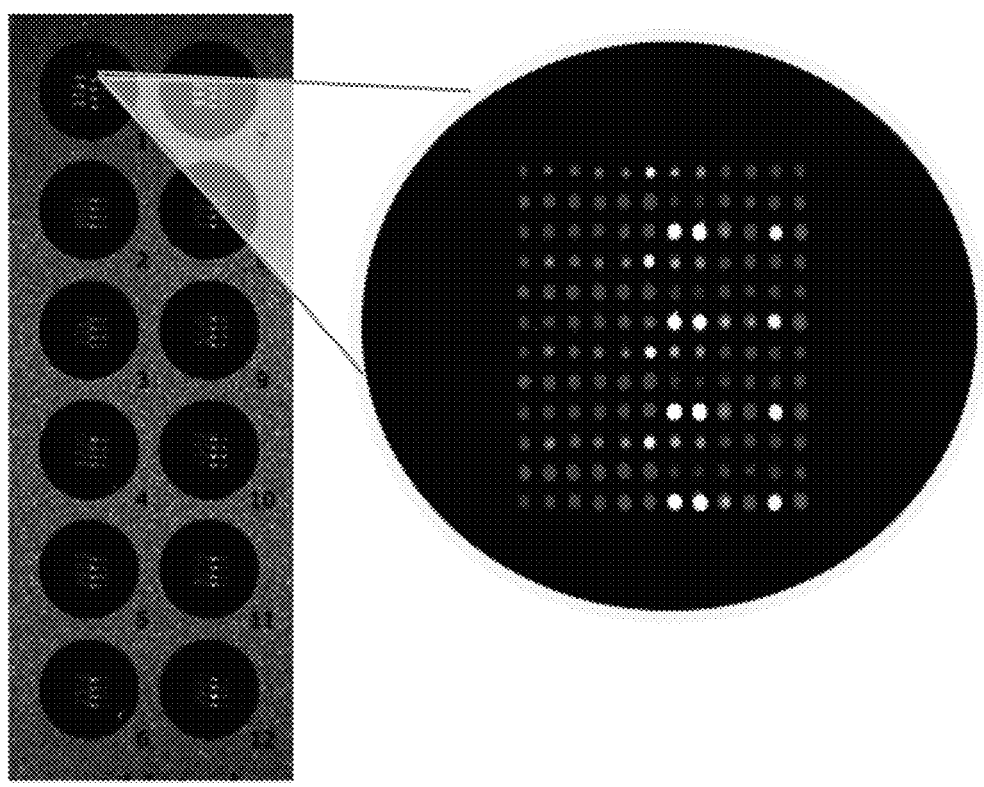
FIG. 10 is a representative image of the microarray format used to implement the nucleic acid probes. This representative format comprises 12 microarrays printed on a glass slide, each separated by a Teflon divider (left). Each microarray queries the full pathogen detection panel in quadruplicate. Also, shown is a blow-up (right) of one such microarray for the analysis of pathogens in *Cannabis* and related plant materials. The Teflon border about each microarray is fit to localize about 50 µL fluid sample for hybridization analysis where fluorescent labeled amplicons and placed onto the microarray for 30 min at room temperature, followed by washing at room temperature then microarray image scanning of the dye-labelled pathogen and host *Cannabis* DNA.

FIG. 10 provide images of a representative implementation of microarrays used in an embodiment. In this implementation, all nucleic acid probes required for bacterial analysis, along with Cannabis DNA controls (Tables 7 and 10) are fabricated into a single 144 element (12×12) microarray, along with additional bacterial and Cannabis probes such as those in Table 10. In this implementation, all nucleic acid probes required for fungi, yeast and mold analysis along with *Cannabis* DNA controls were fabricated into a single 144 element (12×12) microarray, along with additional fungal probes shown in Table 9. The arrays are manufactured on PTFE coated glass slides as two columns of 6 identical microarrays. Each of the 12 identical microarrays is capable of performing, depending on the nucleic acid probes employed, a complete microarray-based analysis bacterial analysis or a complete microarray-based analysis of fungi, yeast and mold. Nucleic acid probes were linked to the glass support via microfluidic printing, either piezoelectric or contact based or an equivalent. The individual microarrays are fluidically isolated from the other 11 in this case, by the hydrophobic PTFE coating, but other methods of physical isolation can be employed.

Figure 11A:
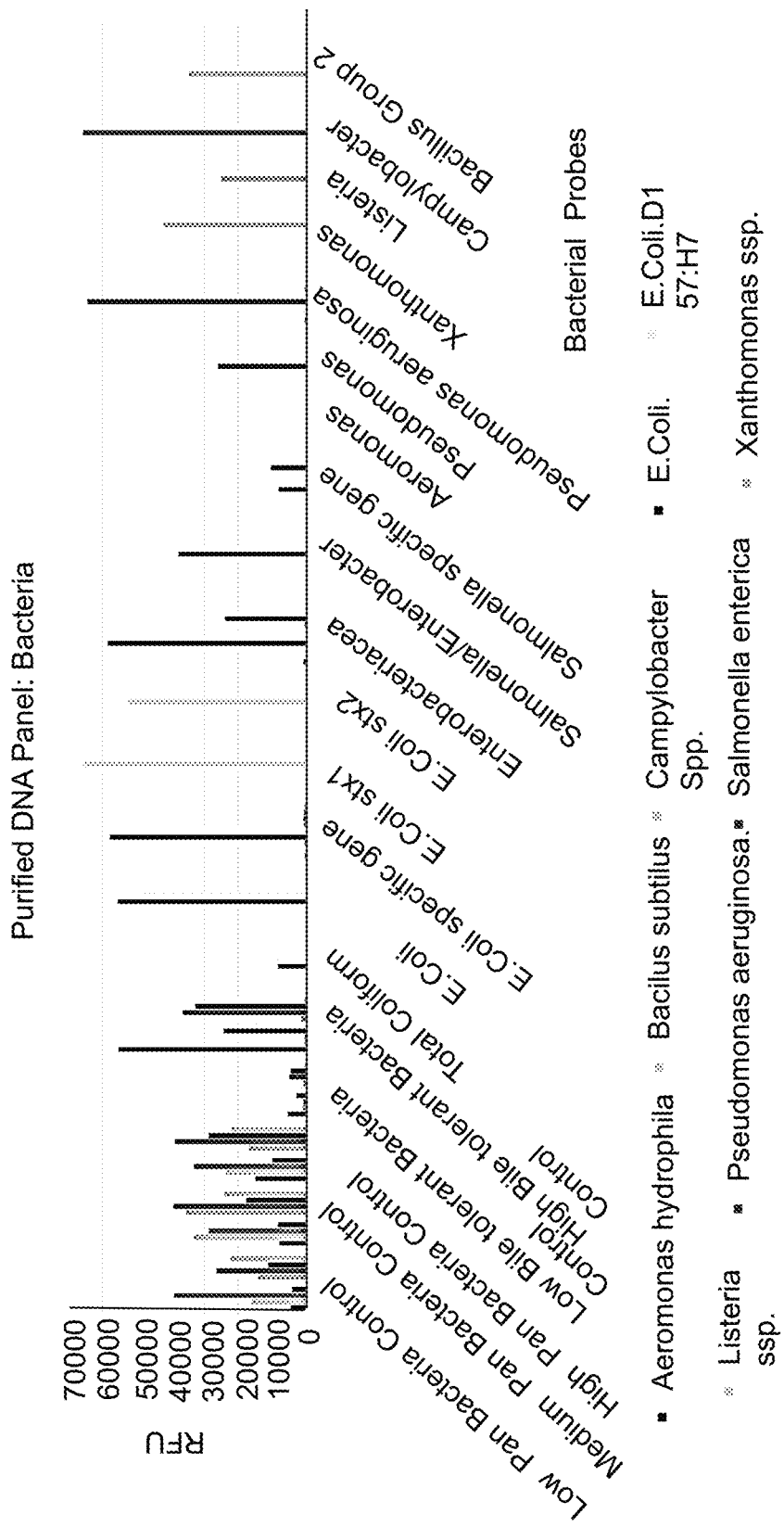
FIGS. 11A-11B shows representative microarray hybridization data obtained from purified bacterial DNA standards (FIG. 11A) and purified fungal DNA standards (FIG. 11B). In each case, the purified bacterial DNA is PCR amplified as though it were an unpurified DNA, then hybridized on the microarray via the microarray probes described above. The data show that in this microarray format, each of the bacteria can be specifically identified via room temperature hybridization and washing. Similarly, the purified fungal DNA is PCR amplified as though it were an unpurified DNA, then hybridized on the microarray via the microarray probes described above. The data show that in this microarray format, each of the fungal DNAs can be specifically identified via room temperature hybridization and washing.
Figure 11B:
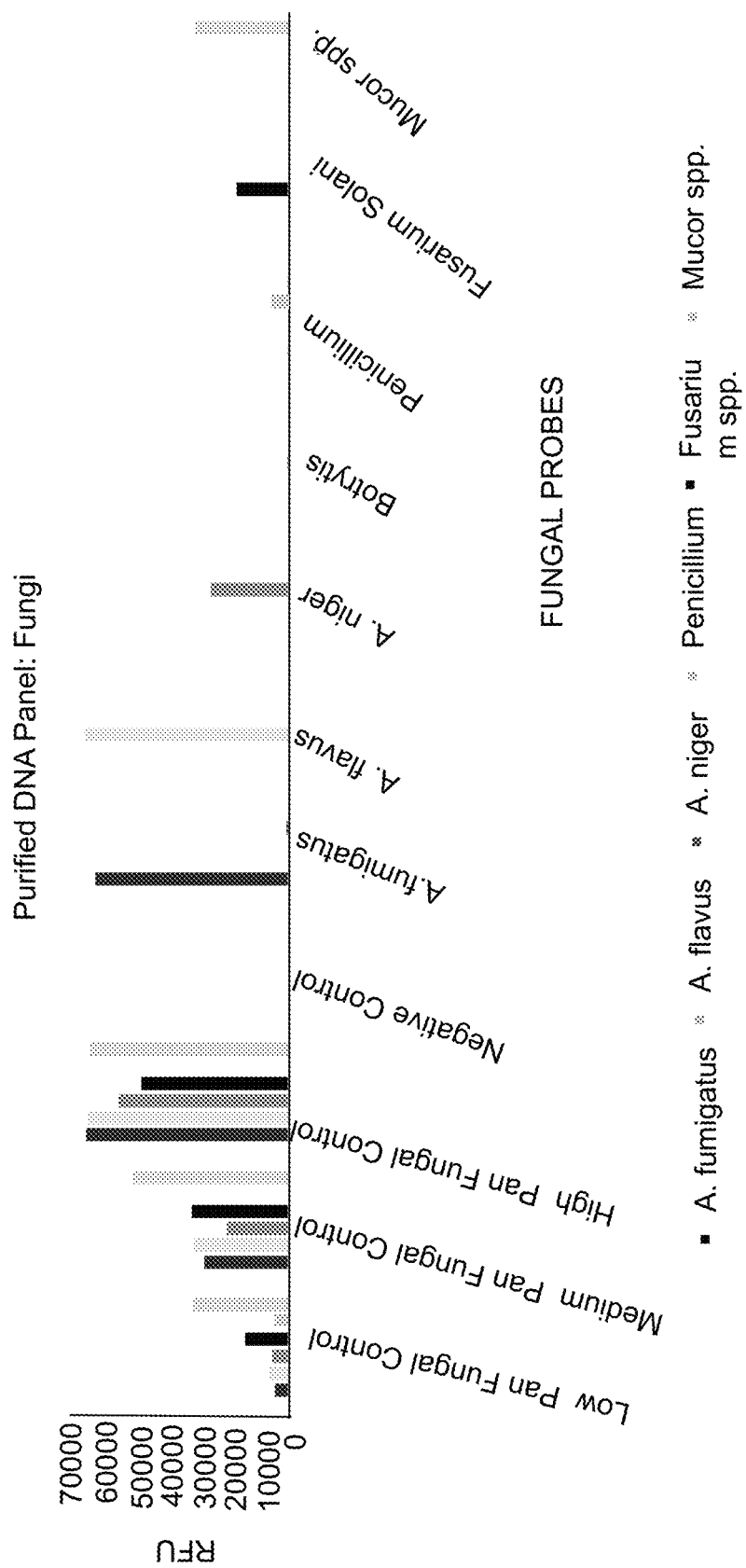
Figure 12:
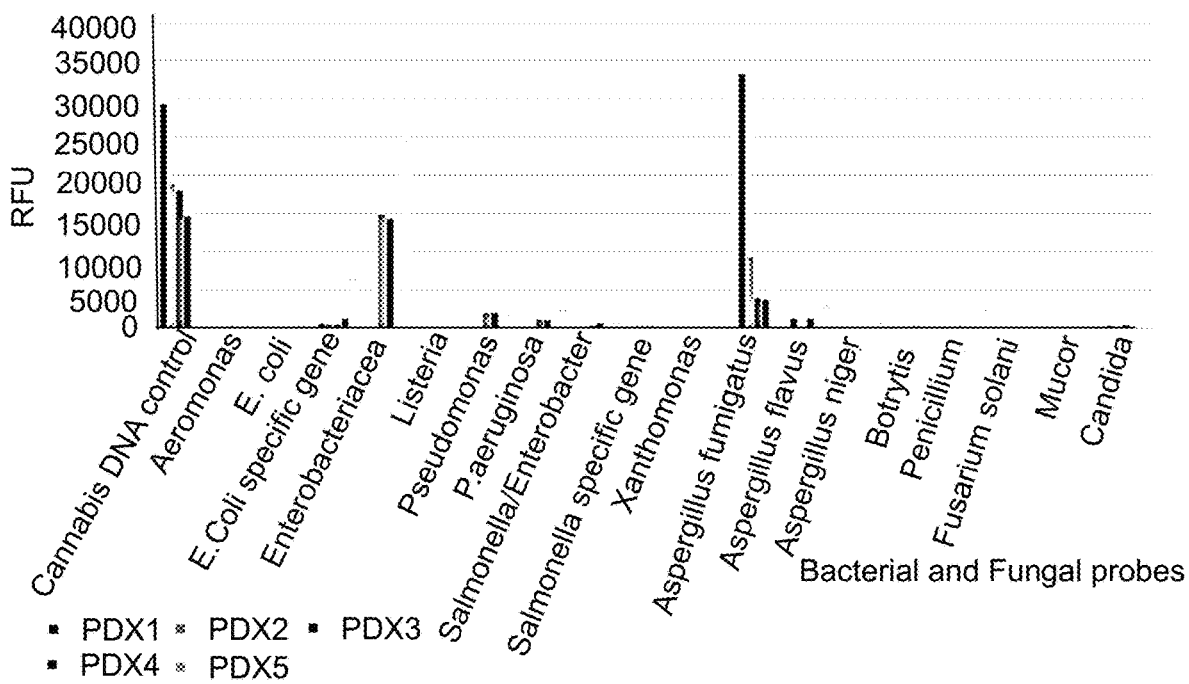
FIG. 12 shows representative microarray hybridization data obtained from 5 representative raw *Cannabis* wash samples. In each case, the raw pathogen complement of these 5 samples is PCR amplified, then hybridized on the microarray via the microarray probes described above. The data show that in this microarray format, specific bacterial, yeast, mold and fungal contaminants can be specifically identified via room temperature hybridization and washing.

FIGS. 11A-11B display representative DNA microarray analysis of an embodiment. In this case, purified bacterial DNA or purified fungal DNA has been used, to test for affinity and specificity subsequent to the two-step PCR reaction and microarray-based hybridization analysis. As can be seen, the nucleic acid probes designed to detect each of the bacterial DNA (top) or fungal DNA (bottom) have bound to the target DNA correctly via hybridization and thus have correctly detected the bacterium or yeast (Table 12 and 13). FIG. 12 displays representative DNA microarray analysis of an embodiment. In this case, 5 different unpurified raw *Cannabis* leaf wash samples were used to test for affinity and specificity subsequent to the two-step PCR reaction and microarray-based hybridization analysis. Both bacterial and fungal analysis has been performed on all 5 leaf wash samples, by dividing each sample into halves and subsequently processing them each for analysis of bacteria or for analysis of fungi, yeast and mold. The data of FIG. 12 were obtained by combining the outcome of both assays. FIG. 12 shows that the combination of two step PCR and microarray hybridization analysis, as described in FIG. 9, can be used to analyze the pathogen complement of a routine *Cannabis* leaf wash. It is expected, but not shown that such washing of any plant material could be performed similarly.

TABLE 12

Representative microarray hybridization data obtained from purified bacterial DNA standards
PURIFIED DNA BACTERIA PANEL

|  | Aeromonas hydrophila | Bacillus subtilus | Campylobactor ssp. |
|---|---|---|---|
| Low Pan Bacteria Control | 4434 | 15943 | 38700 |
| Medium Pan Bacteria Control | 7893 | 33069 | 28705 |
| High Pan Bacteria Control | 14934 | 23469 | 32936 |
| Low Bile tolerant gram negative | 5364 | 947 | 867 |
| High Bile tolerant gram negative | 55228 | 339 | 422 |
| Total Coliform | 106 | 101 | 145 |
| E. coli | 104 | 121 | 127 |
| E. Coli specific gene | 318 | 255 | 422 |
| E. Coli Stx1 | 106 | 116 | 158 |
| E. Coli Stx2 | 100 | 100 | 126 |
| Enterobacteriacea | 885 | 125 | 211 |
| Salmonella/Enterobacter | 115 | 99 | 124 |
| Salmonella specific gene | 189 | 175 | 217 |
| Aeromonas | 10335 | 120 | 123 |
| Pseudomonas | 106 | 107 | 120 |

TABLE 12-continued

Representative microarray hybridization data obtained from purified bacterial DNA standards
PURIFIED DNA BACTERIA PANEL

| Pseudomonas aeruginosa | 169 | 228 | 173 |
|---|---|---|---|
| Xanthomonas | 98 | 188 | 122 |
| Listeria | 117 | 263 | 144 |
| Campylobacter | 148 | 120 | 65535 |
| Bacillus Group 2 | 143 | 34517 | 121 |

|  | E. coli | E. coli O157:H7 | Listeria ssp. |
|---|---|---|---|
| Low Pan Bacteria Control | 4215 | 1745 | 14140 |
| Medium Pan Bacteria Control | 8349 | 3638 | 35237 |
| High Pan Bacteria Control | 9827 | 4327 | 16726 |
| Low Bile tolerant gram negative | 2803 | 1801 | 817 |
| High Bile tolerant gram negative | 24172 | 14746 | 1482 |
| Total Coliform | 8276 | 9175 | 139 |
| E. coli | 55419 | 47805 | 151 |
| E. Coli specific gene | 57638 | 57112 | 521 |
| E. Coli Stx1 | 134 | 65535 | 151 |
| E. Coli Stx2 | 169 | 52041 | 135 |
| Enterobacteriacea | 58323 | 36641 | 179 |
| Salmonella/Enterobacter | 190 | 160 | 144 |
| Salmonella specific gene | 208 | 392 | 212 |
| Aeromonas | 127 | 139 | 163 |
| Pseudomonas | 130 | 126 | 133 |
| Pseudomonas aeruginosa | 318 | 1217 | 208 |
| Xanthomonas | 133 | 143 | 143 |
| Listeria | 136 | 128 | 24783 |
| Campylobacter | 139 | 153 | 224 |
| Bacillus Group 2 | 128 | 150 | 137 |

|  | Pseudomonas aeruginosa | Salmonella enterica | Xanthomonas ssp. |
|---|---|---|---|
| Low Pan Bacteria Control | 26431 | 11167 | 22152 |
| Medium Pan Bacteria Control | 39002 | 17682 | 24141 |
| High Pan Bacteria Control | 38682 | 28596 | 22072 |
| Low Bile tolerant gram negative | 4852 | 4453 | 461 |
| High Bile tolerant gram negative | 36337 | 32579 | 356 |
| Total Coliform | 145 | 204 | 196 |
| E. coli | 144 | 83 | 147 |
| E. Coli specific gene | 695 | 641 | 461 |
| E. Coli Stx1 | 142 | 196 | 145 |
| E. Coli Stx2 | 147 | 117 | 132 |
| Enterobacteriacea | 375 | 23847 | 204 |
| Salmonella/Enterobacter | 138 | 37520 | 144 |
| Salmonella specific gene | 211 | 8124 | 231 |
| Aeromonas | 142 | 99 | 146 |
| Pseudomonas | 25866 | 77 | 153 |
| Pseudomonas aeruginosa | 64437 | 135 | 424 |
| Xanthomonas | 221 | 80 | 41903 |
| Listeria | 144 | 79 | 131 |
| Campylobacter | 144 | 88 | 160 |
| Bacillus Group 2 | 139 | 81 | 134 |

TABLE 13

Representative microarray hybridization data
obtained from purified bacterial DNA standards
PURIFIED DNA FUNGAL PANEL

|  | A. fumigatus | A. flavus | A. niger | Fusarium spp. | Penicillium spp. | Mucor |
|---|---|---|---|---|---|---|
| Low Pan Fungal Control | 4269 | 6097 | 5252 | 13907 | 3929 | 3073 |
| Medium Pan Fungal Control | 27006 | 30445 | 19746 | 30972 | 30947 | 49986 |
| High Pan Fungal Control | 64940 | 64679 | 54483 | 47268 | 65535 | 63932 |
| Negative control | 119 | 127 | 151 | 107 | 117 | 118 |
| A. fumigatus | 62018 | 232 | 114 | 604 | 126 | 228 |
| A. flavus | 210 | 65535 | 116 | 102 | 115 | 128 |
| A. niger | 113 | 235 | 24867 | 108 | 115 | 112 |
| Botrytis | 189 | 205 | 435 | 101 | 126 | 121 |
| Penicillium | 171 | 282 | 121 | 100 | 5891 | 316 |
| F. solani | 112 | 131 | 174 | 16578 | 113 | 140 |
| Mucor | 118 | 127 | 113 | 150 | 113 | 29886 |

FIG. 13 displays representative DNA microarray analysis of an embodiment. In this case, one unpurified (raw) *Cannabis* leaf wash sample was used and was compared to data obtained from a commercially-obtained homogenous yeast vitroid culture of live *Candida* to test for affinity and specificity subsequent to the two-step PCR reaction and microarray-based hybridization analysis. Both *Cannabis* leaf wash and cultured fungal analysis have been performed by processing them each for analysis via probes specific for fungi (see Tables 9 and 11).

The data of FIG. 13 were obtained by combining the outcome of analysis of both the leaf wash and yeast vitroid culture samples. The data of FIG. 13 show that the combination of two step PCR and microarray hybridization analysis, as described in FIG. 9, can be used to interrogate the fungal complement of a routine *Cannabis* leaf wash as adequately as can be done with a pure (live) fungal sample. It is expected that fungal analysis via such washing of any plant material could be performed similarly.

Figure 14:
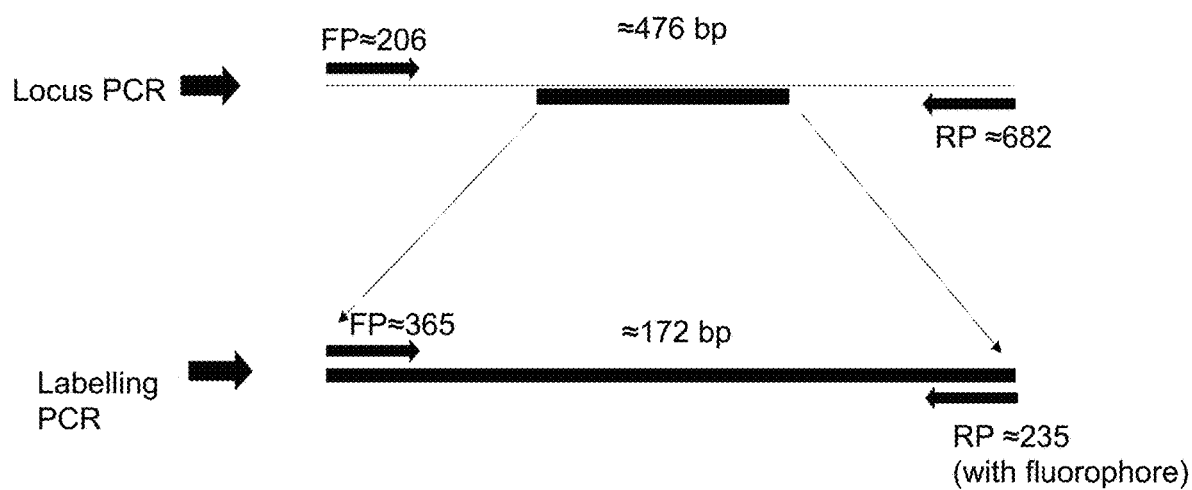
FIG. 14 shows a graphical representation of the position of PCR primers employed in a variation of an embodiment for low level detection of Bacteria in the Family Enterobacteriaceae including *E. coli*. These PCR primers are used to selectively amplify and dye label DNA from targeted organisms for analysis via microarray hybridization.

FIG. 14 shows a graphical representation of the position of PCR primers employed in a variation of an embodiment for low level detection of Bacteria in the Family Enterobacteriaceae including *E. coli*. These PCR primers are used to selectively amplify and dye label DNA from targeted organisms for analysis via microarray hybridization.

Figure 15A:
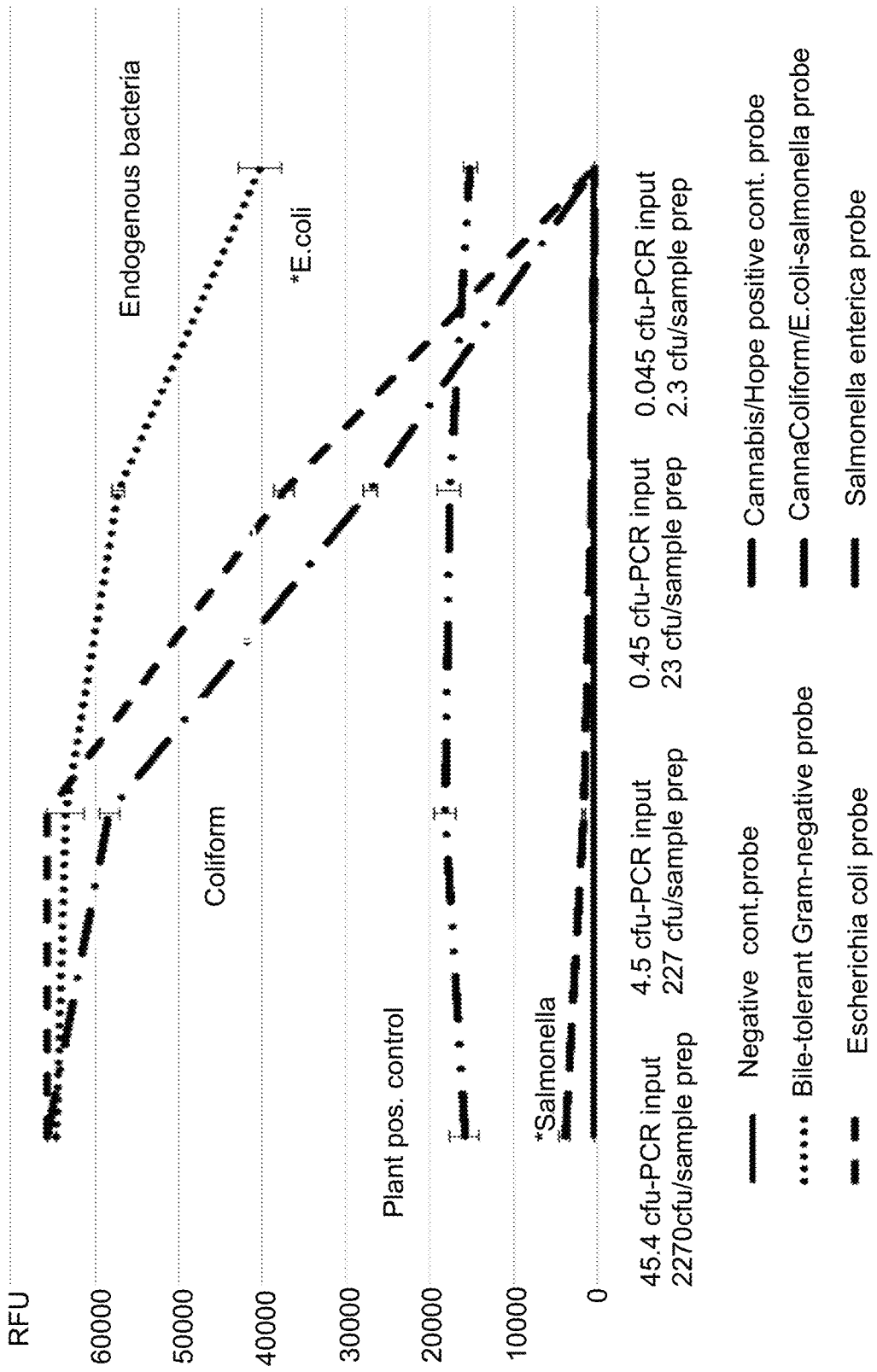
FIG. 15A is a graphical representation of microarray hybridization data demonstrating low level detection of *E. coli* O157:H7 from certified reference material consisting of enumerated colonies of specified bacteria spiked onto *Humulus lupulus*, (Hop plant).
Figure 15B:
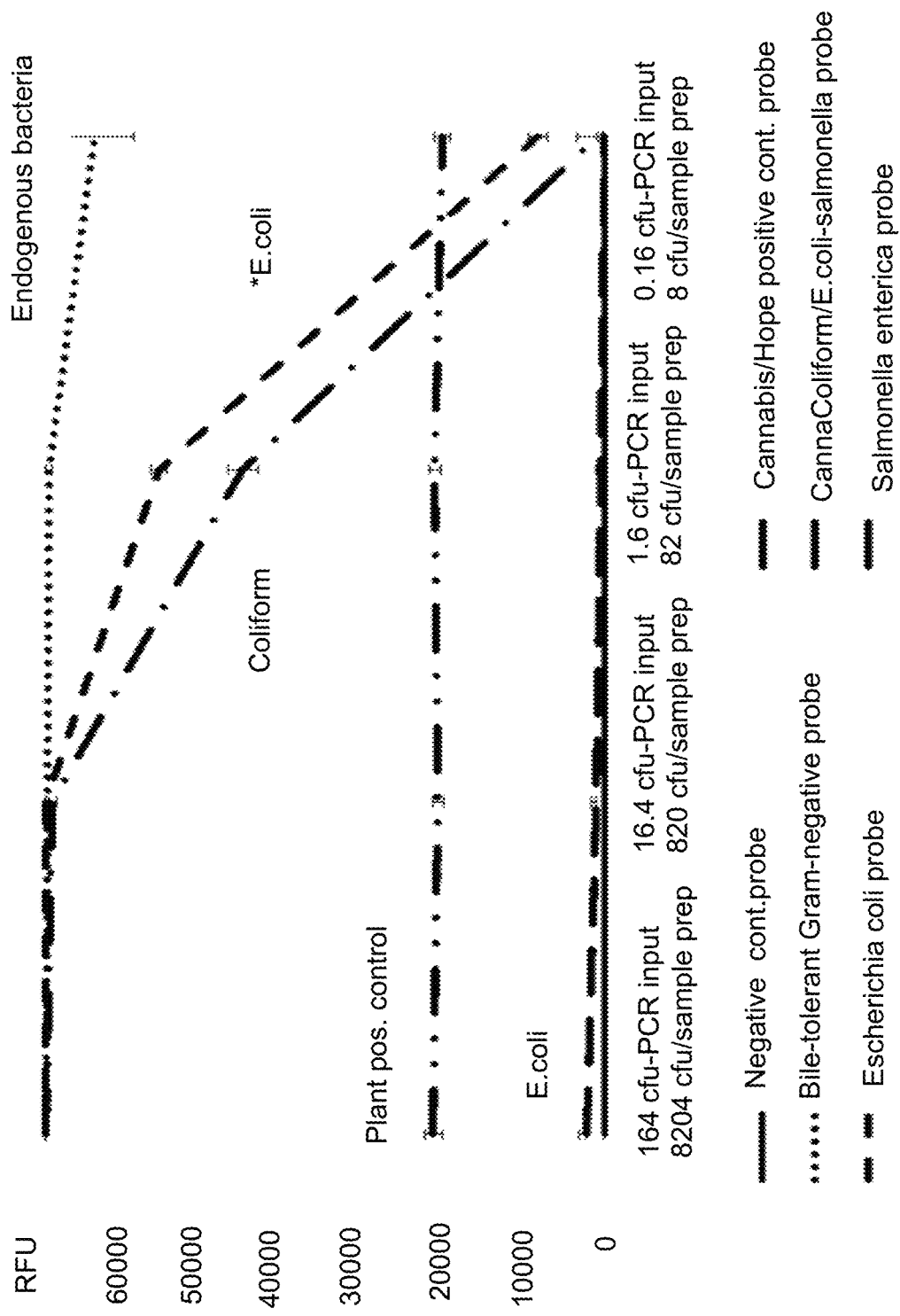
FIG. 15B is a graphical representation of microarray hybridization data demonstrating low level detection of *E. coli* O1111 from certified reference material consisting of enumerated colonies of specified bacteria spiked onto *Humulus lupulus*, (Hop plant).
Figure 15C:
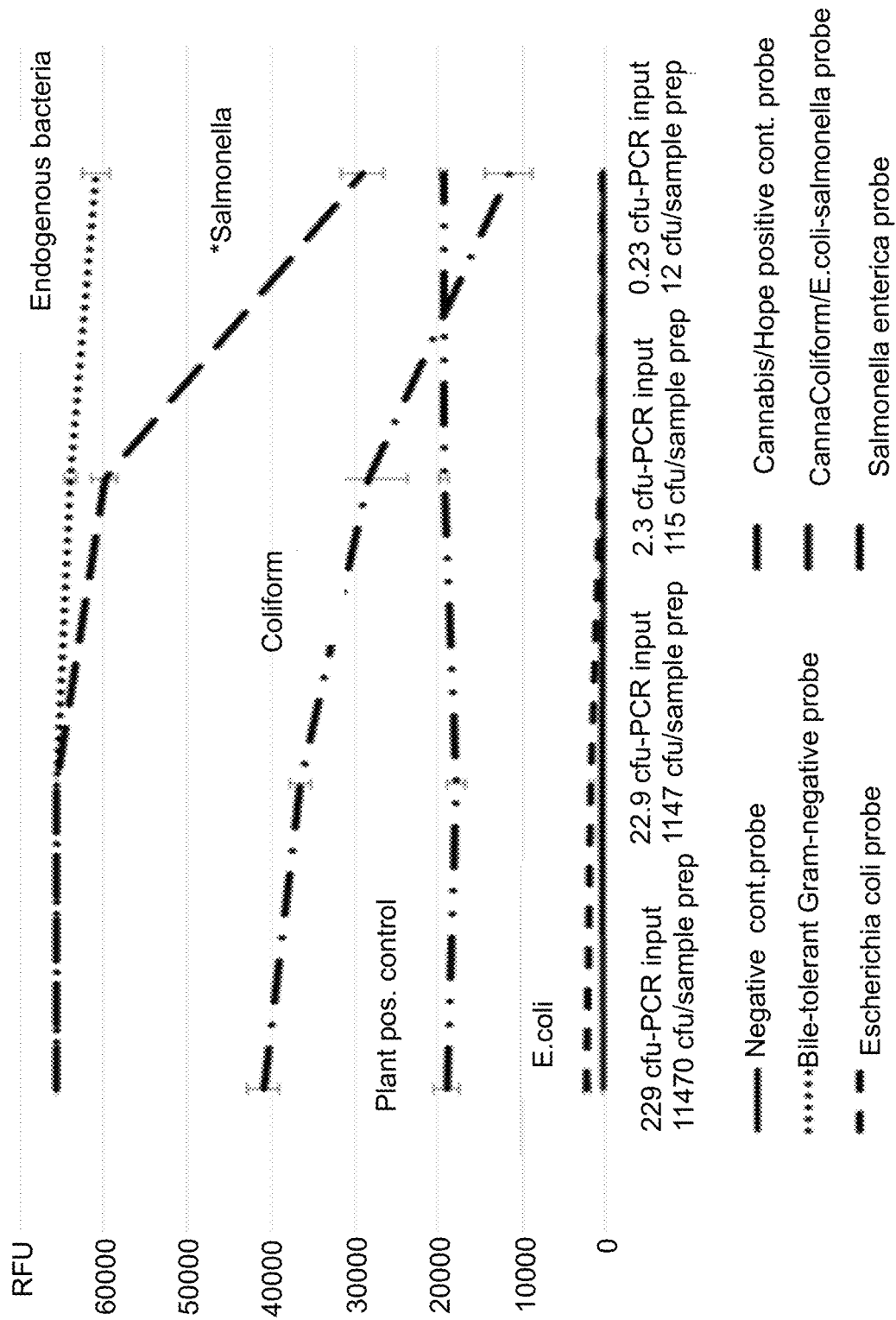
FIG. 15C is a graphical representation of microarray hybridization data demonstrating low level detection of *Salmonella enterica* from certified reference material consisting of enumerated colonies of specified bacteria spiked onto *Humulus lupulus*, (Hop plant).

FIGS. 15A-15C illustrate representative DNA microarray analysis demonstrating assay sensitivity over a range of microbial inputs. In this case, certified reference material consisting of enumerated bacterial colonies of *E. coli* O157: H7, *E. coli* O111 (FIGS. 15A-15B) and *Salmonella enterica* (FIG. 15C) were spiked as a dilution series onto a hops plant surrogate matrix then processed using the assay version described for FIG. 14. Hybridization results from relevant probes from FIG. 7 are shown. The larger numbers on the x-axis represents the total number of bacterial colony forming units (CFU) that were spiked onto each hops plant sample, whereas the smaller numbers on the x-axis represent the number of CFU's of the spiked material that were actually inputted into the assay. Only about ⅟₅₀ of the original spiked hops sample volume was actually analyzed. The smaller numbers upon the x-axis of FIGS. 15A-15C are exactly ⅟₅₀$^{th}$ that of the total (lower) values. As is seen, FIGS. 15A-15C show that the microarray test of an embodiment can detect less than 1 CFU per microarray assay. The nucleic acid targets within the bacterial genomes displayed in FIGS. 15A-15C comprise 16s rDNA. There are multiple copies of the 16s rDNA gene in each of these bacterial organisms, which enables detection at <1 CFU levels. Since a colony forming unit approximates a single bacterium in many cases, the data of FIGS. 15A-15C demonstrate that the present microarray assay has sensitivity which approaches the ability to detect a single (or a small number) of bacteria per assay. Similar sensitivity is expected for all bacteria and eukaryotic microbes in that it is known that they all present multiple copies of the ribosomal rDNA genes per cell.

Tables 14A and 14B show a collection of representative microarray hybridization data obtained from powdered dry food samples with no enrichment and 18-hour enrichment for comparison. The data shows that bacterial microbes were successfully detected on the microarrays of the present invention without the need for enrichment.

Figure 16:
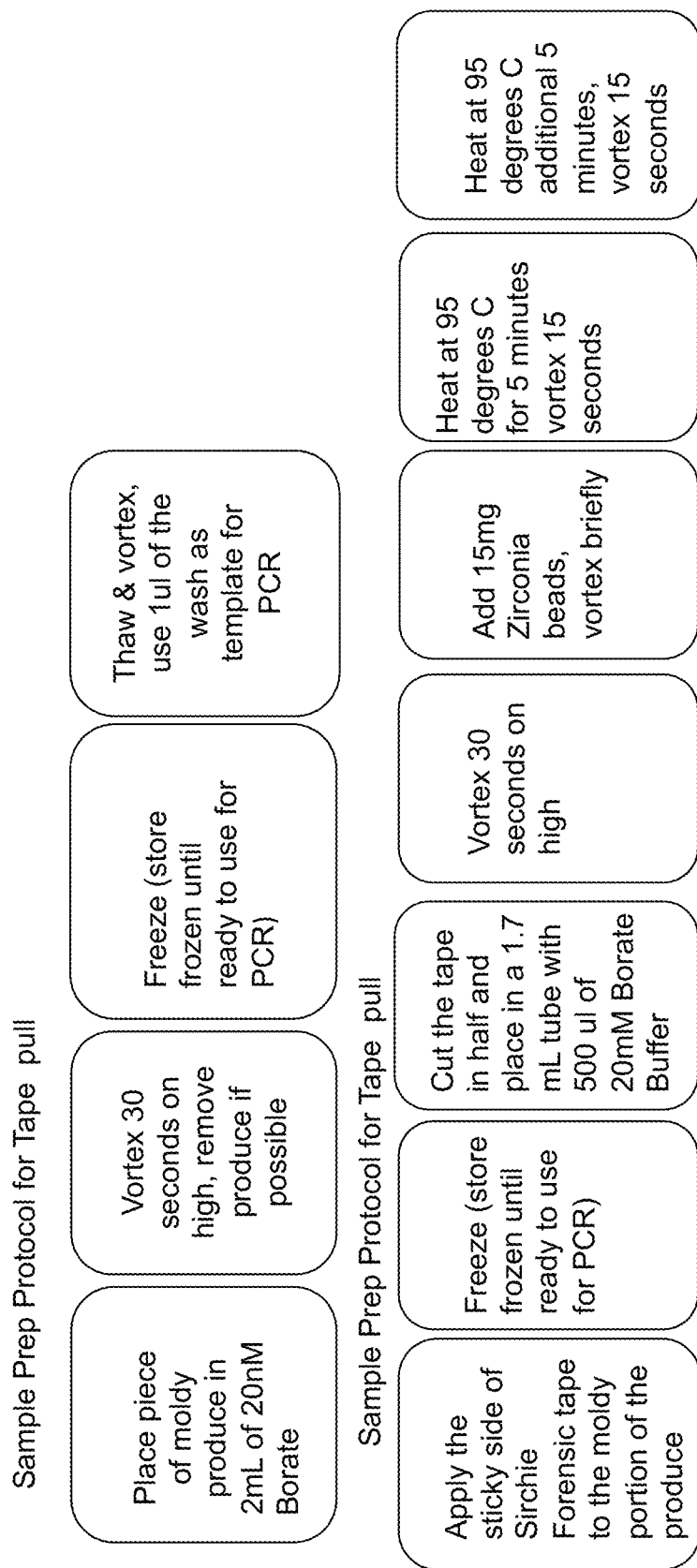
FIG. 16 shows diagrams for sample collection and preparation from two methods. Both the tape pull and wash method are used to process samples to provide a solution for microbial detection via microarray analysis.

FIG. 16 and Tables 15-17 describes embodiments for the analysis of fruit, embodiments for the analysis of vegetables and embodiments for the analysis of other plant matter. The above teaching shows, by example, that unprocessed leaf and bud samples in *Cannabis* and hops may be washed in an aqueous water solution, to yield a water-wash containing microbial pathogens which can then be analyzed via the present combination of RSG and microarrays.

If fresh leaf, flower, stem or root materials from fruit and vegetables are also washed in a water solution in that same way (when fresh, or after drying and grinding or other types or processing, then the present combination of RSG and microarray analysis would be capable of recovering and analyzing the DNA complement of those microbes in those other plant materials. At least two methods of sample collection are possible for fruit and vegetables. One method is the simple rinsing of the fruit, exactly as described for *Cannabis*, above. Another method of sample collection from fruits and vegetables is a "tape pull", wherein a piece of standard forensic tape is applied to the surface of the fruit, then pulled off. Upon pulling, the tape is then soaked in the standard wash buffer described above, to suspend the microbes attached to the tape. Subsequent to the tape-wash step, all other aspects of the processing and analysis (i.e., raw sample genotyping, PCR, then microarray analysis) are exactly as described above.

TABLE 14A

Representative microarray data obtained from powdered dry food samples

| | Sample Type | | | | | | | | | |
|---|---|---|---|---|---|---|---|---|---|---|
| | Whey Protein Shake Vanilla | | Whey Protein Shake Chocolate | | Chewable Berry Tablet | | Vanilla Shake | | Pea Protein | |
| | Enrichment time | | | | | | | | | |
| | 0 hours | 18 hours | 0 hours | 18 hours | 0 hours | 18 hours | 0 hours | 18 hours | 0 hours | 18 hours |
| Negative Control Probe | 289 | 318 | 349 | 235 | 327 | 302 | 358 | 325 | 321 | 299 |
| Total Aerobic Bacteria Probes | | | | | | | | | | |
| High sensitivity | 26129 | 38896 | 16629 | 11901 | 3686 | 230 | 32747 | 12147 | 41424 | 40380 |
| Medium sensitivity | 5428 | 6364 | 3308 | 2794 | 876 | 215 | 7310 | 2849 | 15499 | 8958 |
| Low sensitivity | 2044 | 3419 | 1471 | 990 | 446 | 181 | 2704 | 1062 | 4789 | 3887 |
| Bile-tolerant Gram-negative Probes | | | | | | | | | | |
| High sensitivity | 2639 | 350 | 1488 | 584 | 307 | 305 | 1041 | 472 | 15451 | 8653 |
| Medium sensitivity | 1713 | 328 | 892 | 493 | 322 | 362 | 615 | 380 | 6867 | 4997 |
| Low sensitivity | 974 | 600 | 749 | 621 | 595 | 688 | 821 | 929 | 2459 | 1662 |
| Total Enterobacteriaceae Probes | | | | | | | | | | |
| High sensitivity | 1131 | 306 | 363 | 310 | 346 | 318 | 273 | 331 | 4260 | 3149 |
| Medium sensitivity | 479 | 296 | 320 | 297 | 329 | 339 | 314 | 342 | 1489 | 990 |
| Low sensitivity | 186 | 225 | 203 | 165 | 205 | 181 | 207 | 200 | 216 | 259 |
| 16S rDNA Species Probes | | | | | | | | | | |
| *Escherichia coli/Shigella* spp. | 233 | 205 | 255 | 219 | 207 | 255 | 215 | 214 | 242 | 198 |
| *S. enterica/enterobacter* spp. | 203 | 183 | 186 | 281 | 212 | 299 | 197 | 257 | 308 | 303 |
| *Bacillus* spp. | 154 | 172 | 189 | 114 | 307 | 156 | 169 | 153 | 233 | 259 |
| *Pseudomonas* spp. | 549 | 201 | 202 | 251 | 148 | 216 | 303 | 276 | 2066 | 983 |
| Organism Specific Gene Probes | | | | | | | | | | |
| tuf gene(*E. coli*) | 204 | 129 | 180 | 272 | 158 | 190 | 191 | 183 | 186 | 192 |
| stx1 gene(*E. coli*) | 241 | 178 | 171 | 240 | 289 | 304 | 195 | 245 | 149 | 191 |
| stx2 gene(*E. coli*) | 145 | 96 | 136 | 125 | 182 | 224 | 130 | 142 | 85 | 127 |
| invA (*Salmonella* spp.) | 215 | 265 | 210 | 284 | 204 | 256 | 239 | 285 | 237 | 229 |

TABLE 14B

Representative microarray data obtained from powdered dry food samples

| | Sample Type | | | | | | | |
|---|---|---|---|---|---|---|---|---|
| | Rice Protein | | Work-out Shake FP | | Work-out Shake BR | | Vanilla Shake | |
| | Enrichment time | | | | | | | |
| | 0 hours | 18 hours | 0 hours | 18 hours | 0 hours | 18 hours | 0 hours | 18 hours |
| Negative Control Probe | 351 | 351 | 271 | 309 | 299 | 332 | 246 | 362 |
| Total Aerobic Bacteria Probes | | | | | | | | |
| High sensitivity | 471 | 288 | 17146 | 266 | 19207 | 261 | 41160 | 47198 |
| Medium sensitivity | 161 | 187 | 3120 | 229 | 3309 | 311 | 10060 | 22103 |
| Low sensitivity | 186 | 239 | 1211 | 261 | 1223 | 264 | 3673 | 6750 |
| Bile-tolerant Gram-negative Probes | | | | | | | | |
| High sensitivity | 326 | 372 | 375 | 380 | 412 | 363 | 1418 | 358 |
| Medium sensitivity | 304 | 362 | 341 | 391 | 308 | 356 | 699 | 394 |
| Low sensitivity | 683 | 942 | 856 | 689 | 698 | 864 | 848 | 665 |
| Total Enterobacteriaceae Probes | | | | | | | | |
| High sensitivity | 277 | 329 | 317 | 327 | 298 | 326 | 290 | 349 |
| Medium sensitivity | 326 | 272 | 296 | 291 | 297 | 263 | 262 | 307 |
| Low sensitivity | 215 | 207 | 204 | 288 | 213 | 269 | 195 | 247 |

TABLE 14B-continued

Representative microarray data obtained from powdered dry food samples

| | Sample Type | | | | | | | |
|---|---|---|---|---|---|---|---|---|
| | Rice Protein | | Work-out Shake FP | | Work-out Shake BR | | Vanilla Shake | |
| | Enrichment time | | | | | | | |
| | 0 hours | 18 hours | 0 hours | 18 hours | 0 hours | 18 hours | 0 hours | 18 hours |
| 16S rDNA Species Probes | | | | | | | | |
| *Escherichia coli/Shigella* spp. | 228 | 229 | 216 | 267 | 221 | 253 | 220 | 207 |
| *S. enterica/enterobacter* spp. | 226 | 281 | 238 | 268 | 197 | 254 | 255 | 216 |
| *Bacillus* spp. | 157 | 166 | 812 | 208 | 915 | 216 | 415 | 168 |
| *Pseudomonas* spp. | 199 | 225 | 247 | 251 | 211 | 259 | 277 | 225 |
| Organism Specific Gene Probes | | | | | | | | |
| tuf gene(*E. coli*) | 150 | 149 | 126 | 206 | 163 | 212 | 215 | 166 |
| stx1 gene(*E. coli*) | 270 | 247 | 211 | 299 | 239 | 307 | 175 | 185 |
| stx2 gene(*E. coli*) | 158 | 178 | 127 | 205 | 138 | 175 | 128 | 100 |
| invA (*Salmonella* spp.) | 257 | 241 | 249 | 264 | 220 | 258 | 239 | 245 |

The data of Tables 15-17 demonstrates that simple washing of the fruit and tape pull sampling of the fruit generate similar microbial data. The blueberry sample is shown to be positive for *Botrytis*, as expected, since *Botrytis* is a well-known fungal contaminant on blueberries. The lemon sample is shown to be positive for *Penicillium*, as expected, since *Penicillium* is a well-known fungal contaminant for lemons.

TABLE 15

Representative microarray hybridization data obtained from blueberry and lemon washes.

| | Sample | | | |
|---|---|---|---|---|
| | Blueberry | | Lemon | |
| | Collection Type Produce Wash Protocol | | | |
| | Wash 1 blueberry in 2 ml 20 mM Borate, vortex 30 seconds | | Wash 1 piece moldy lemon in 2 ml 20 mM Borate, vortex 30 seconds | |
| | Dilution Factor | | | |
| | NONE | 1:20 | NONE | 1:20 |
| *A. fumigatus* 1 | 65 | 61 | 62 | 57 |
| *A. fumigatus* 2 | 66 | 61 | 58 | 131 |
| *A. fumigatus* 3 | 69 | 78 | 55 | 127 |
| *A. fumigatus* 4 | 80 | 198 | 63 | 161 |
| *A. fumigatus* 5 | 98 | 68 | 59 | 70 |
| *A. flavus* 1 | 111 | 65 | 197 | 58 |
| *A. flavus* 2 | 64 | 66 | 71 | 49 |
| *A. flavus* 3 | 72 | 79 | 54 | 49 |
| *A. flavus* 4 | 95 | 71 | 66 | 125 |
| *A. flavus* 5 | 59 | 55 | 45 | 47 |
| *A. niger* 1 | 91 | 75 | 61 | 61 |
| *A. niger* 2 | 185 | 68 | 61 | 57 |
| *A. niger* 3 | 93 | 66 | 62 | 61 |
| *A. niger* 4 | 1134 | 74 | 75 | 64 |
| *Botrytis* spp. 1 | 26671 | 27605 | 60 | 55 |
| *Botrytis* spp. 2 | 26668 | 35611 | 59 | 57 |
| *Penicillium* spp. 1 | 63 | 69 | 2444 | 4236 |
| *Penicillium* spp. 2 | 71 | 69 | 4105 | 7426 |
| *Fusarium* spp. 1 | 175 | 69 | 59 | 78 |
| *Fusarium* spp. 2 | 71 | 73 | 84 | 62 |
| *Mucor* spp. 1 | 71 | 57 | 58 | 61 |
| *Mucor* spp. 2 | 61 | 290 | 66 | 61 |
| Total Yeast and Mold 1 | 20052 | 21412 | 8734 | 7335 |
| Total Yeast and Mold 2 | 17626 | 8454 | 5509 | 5030 |

TABLE 16

Representative microarray hybridization data obtained from blueberry washes and tape pulls Sample: Moldy Blueberry
Collection Type: Tape Pull

| ID | 1A1 | 1A1 | 1A2 | 1A2 | 1A3 | 1A3 | 1B1 | 1B1 | 1B2 | 1B2 | 1B3 | 1B3 |
|---|---|---|---|---|---|---|---|---|---|---|---|---|
| Collection Point 1 | 500 ul 20 mM Borate Buffer, vortex 30 seconds | | | | | | 500 ul 20 mM Borate + Triton Buffer, vortex 30 seconds | | | | | |
| Collection Point 2 | Add 15 mg zirconia beads, vortex, Heat 5 min 95° C., Vortex 15 seconds | | | | | | Add 15 mg zirconia beads, vortex, Heat 5 min 95° C., Vortex 15 seconds | | | | | |
| Collection Point 3 | | | | | Heat 5 min 95° C. vortex 15 seconds | | | | | | Heat 5 min 95° C. vortex 15 seconds | |
| Dilution Factor | NO | 1:20 | NO | 1:20 | NO | 1:20 | NO | 1:20 | NO | 1:20 | NO | 1:20 |
| A. fumigatus 1 | 66 | 388 | 83 | 77 | 97 | 313 | 95 | 68 | 76 | 55 | 75 | 60 |
| A. fumigatus 2 | 97 | 100 | 82 | 118 | 69 | 56 | 87 | 67 | 185 | 76 | 58 | 52 |
| A. fumigatus 3 | 77 | 94 | 82 | 1083 | 87 | 61 | 93 | 84 | 75 | 378 | 73 | 64 |
| A. fumigatus 4 | 84 | 151 | 94 | 118 | 96 | 80 | 115 | 85 | 85 | 93 | 190 | 88 |
| A. fumigatus 5 | 63 | 75 | 96 | 71 | 78 | 61 | 98 | 74 | 68 | 98 | 70 | 533 |
| A. flavus 1 | 200 | 107 | 113 | 61 | 204 | 58 | 105 | 73 | 62 | 68 | 64 | 65 |
| A. flavus 2 | 70 | 104 | 64 | 57 | 133 | 281 | 111 | 78 | 377 | 314 | 57 | 50 |
| A. flavus 3 | 83 | 90 | 94 | 150 | 99 | 90 | 96 | 222 | 1162 | 86 | 80 | 73 |
| A. flavus 4 | 76 | 125 | 92 | 146 | 87 | 174 | 241 | 78 | 115 | 69 | 105 | 85 |
| A. flavus 5 | 80 | 153 | 77 | 72 | 78 | 439 | 71 | 86 | 280 | 58 | 62 | 57 |
| A. niger 1 | 409 | 178 | 122 | 72 | 80 | 70 | 76 | 71 | 152 | 117 | 65 | 53 |
| A. niger 2 | 78 | 292 | 79 | 65 | 715 | 666 | 74 | 70 | 68 | 731 | 70 | 54 |
| A. niger 3 | 86 | 76 | 87 | 558 | 78 | 60 | 70 | 81 | 96 | 63 | 478 | 58 |
| A. niger 4 | 164 | 70 | 92 | 108 | 197 | 69 | 130 | 75 | 76 | 148 | 73 | 65 |
| Botrytis spp. 1 | 41904 | 26549 | 28181 | 29354 | 25304 | 25685 | 57424 | 33783 | 57486 | 49803 | 33176 | 32153 |
| Botrytis spp. 2 | 36275 | 25518 | 29222 | 27076 | 26678 | 27675 | 49480 | 32899 | 52817 | 34322 | 29693 | 32026 |
| Penicillium spp. 1 | 80 | 81 | 83 | 64 | 96 | 60 | 79 | 80 | 176 | 60 | 385 | 53 |
| Penicillium spp. 2 | 90 | 93 | 81 | 80 | 114 | 59 | 98 | 69 | 470 | 65 | 478 | 56 |
| Fusarium spp. 1 | 77 | 71 | 69 | 62 | 112 | 55 | 61 | 274 | 617 | 81 | 59 | 757 |
| Fusarium spp. 2 | 91 | 82 | 107 | 74 | 101 | 65 | 91 | 66 | 123 | 63 | 71 | 583 |
| Mucor spp. 1 | 90 | 314 | 73 | 88 | 105 | 61 | 77 | 79 | 741 | 180 | 172 | 74 |
| Mucor spp. 2 | 83 | 69 | 73 | 69 | 91 | 67 | 111 | 102 | 455 | 88 | 70 | 133 |
| Total Y & M 1 | 23637 | 18532 | 15213 | 17668 | 18068 | 19762 | 18784 | 15550 | 20625 | 17525 | 25813 | 18269 |
| Total Y & M 2 | 12410 | 8249 | 9281 | 11526 | 8543 | 13007 | 14180 | 14394 | 9905 | 8972 | 15112 | 12678 |

The data embodied in FIG. 16 and Tables 15-17 demonstrate the use of an embodiment, for the recovery and analysis of yeast microbes on the surface of fruit (blueberries and lemons in this case), but an embodiment could be extended to other fruits and vegetables for the analysis of both bacterial and fungal contamination.

TABLE 17

Representative microarray hybridization data obtained from lemon washes and tape pulls.

Sample: Moldy Lemon
Collection Type: Tape Pull

| ID | 1A1 Lemon | 1A2 Lemon | 1A3 Lemon | 1B1 Lemon | 1B2 Lemon |
|---|---|---|---|---|---|
| Collection Point 1 | 500 ul 20 mM Borate + Triton Buffer, vortex 30 seconds | | | | |
| Collection Point 2 | Add 15 mg zirconia beads, vortex, Heat 5 min 95° C., Vortex 15 seconds | | | Add 15 mg zirconia beads, vortex, Heat 5 min 95° C., Vortex 15 seconds | |
| Collection Point 3 | | | Heat 5 min 95° C. vortex 15 seconds | | |
| Dilution Factor | NONE | | | | |
| A. fumigatus 1 | 96 | 83 | 75 | 83 | 64 |
| A. fumigatus 2 | 221 | 73 | 71 | 66 | 101 |

TABLE 17-continued

Representative microarray hybridization data obtained from lemon washes and tape pulls.

Sample: Moldy Lemon
Collection Type: Tape Pull

| ID | 1A1 Lemon | 1A2 Lemon | 1A3 Lemon | 1B1 Lemon | 1B2 Lemon |
|---|---|---|---|---|---|
| A. fumigatus 3 | 87 | 88 | 85 | 92 | 122 |
| A. fumigatus 4 | 83 | 85 | 91 | 72 | 97 |
| A. fumigatus 5 | 448 | 100 | 84 | 114 | 78 |
| A. flavus 1 | 85 | 79 | 70 | 66 | 63 |
| A. flavus 2 | 77 | 82 | 77 | 79 | 63 |
| A. flavus 3 | 133 | 66 | 86 | 60 | 67 |
| A. flavus 4 | 96 | 85 | 81 | 98 | 88 |
| A. flavus 5 | 68 | 62 | 65 | 106 | 59 |
| A. niger 1 | 73 | 88 | 77 | 73 | 73 |
| A. niger 2 | 74 | 84 | 81 | 71 | 103 |
| A. niger 3 | 90 | 86 | 87 | 74 | 78 |
| A. niger 4 | 82 | 93 | 104 | 86 | 161 |
| Botrytis spp. 1 | 82 | 75 | 75 | 77 | 68 |
| Botrytis spp. 2 | 91 | 74 | 83 | 67 | 62 |
| Penicillium spp. 1 | 3824 | 5461 | 5500 | 4582 | 5290 |
| Penicillium spp. 2 | 7586 | 8380 | 11177 | 6528 | 8167 |
| Fusarium spp. 1 | 101 | 62 | 61 | 70 | 279 |
| Fusarium spp. 2 | 77 | 122 | 78 | 68 | 233 |
| Mucor spp. 1 | 74 | 110 | 89 | 76 | 57 |
| Mucor spp. 2 | 132 | 1302 | 90 | 84 | 61 |
| Total Yeast and Mold 1 | 8448 | 12511 | 9249 | 12844 | 8593 |
| Total Yeast and Mold 2 | 9275 | 8716 | 11585 | 10758 | 4444 |

Table 18 shows embodiments for the analysis of environmental water samples/specimens. The above teaching shows by example that unprocessed leaf and bud samples in *Cannabis* and hops may be washed in an aqueous water solution, to yield a water-wash containing microbial pathogens which can then be analyzed via the present combination of Raw Sample Genotyping (RSG) and microarrays. If a water sample containing microbes were obtained from environmental sources (such as well water, or sea water, or soil runoff or the water from a community water supply) and then analyzed directly, or after ordinary water filtration to concentrate the microbial complement onto the surface of the filter, that the present combination of RSG and microarray analysis would be capable of recovering and analyzing the DNA complement of those microbes.

TABLE 18

Representative microarray data from raw water filtrate.

| Sample ID | 2 H | 2 H | 9 D | 9 D | 21 | 21 | 23 | 23 | 25 | 25 | Negative Control |
|---|---|---|---|---|---|---|---|---|---|---|---|
| Imager Calibration High | 311 | 335 | 322 | 379 | 341 | 348 | 345 | 325 | 354 | 343 | 333 |
| Imager Calibration Med | 280 | 314 | 268 | 286 | 288 | 231 | 253 | 295 | 267 | 295 | 244 |
| Imager Calibration Low | 245 | 296 | 302 | 324 | 254 | 268 | 293 | 285 | 271 | 340 | 275 |
| Cannabis cont. | 310 | 330 | 313 | 255 | 323 | 368 | 313 | 322 | 274 | 332 | 322 |
| Cannabis cont. | 313 | 237 | 298 | 271 | 298 | 288 | 296 | 280 | 249 | 284 | 297 |
| Cannabis cont. | 208 | 265 | 276 | 250 | 267 | 327 | 255 | 258 | 253 | 282 | 370 |
| Total Yeast and Mold | 284 | 324 | 290 | 307 | 272 | 361 | 296 | 288 | 271 | 321 | 469 |
| Total Yeast and Mold | 251 | 259 | 294 | 290 | 309 | 308 | 285 | 281 | 275 | 299 | 293 |
| Total Yeast and Mold | 282 | 280 | 294 | 280 | 299 | 284 | 275 | 286 | 299 | 259 | 232 |
| Total Aerobic bacteria High | 40101 | 42007 | 47844 | 47680 | 45102 | 44041 | 43520 | 41901 | 46459 | 46783 | 135 |
| Total Aerobic bacteria Medium | 14487 | 12314 | 24189 | 26158 | 19712 | 16210 | 17943 | 15474 | 25524 | 18507 | 157 |
| Total Aerobic bacteria Low | 4885 | 5629 | 7625 | 6456 | 5807 | 4505 | 5316 | 6022 | 6264 | 6974 | 159 |
| Negative Control | 293 | 359 | 303 | 339 | 312 | 329 | 306 | 377 | 307 | 335 | 307 |
| Aspergillus fumigatus | 285 | 291 | 284 | 268 | 289 | 265 | 271 | 281 | 269 | 248 | 228 |
| Aspergillus flavus | 184 | 211 | 201 | 344 | 237 | 179 | 212 | 213 | 163 | 204 | 171 |
| Aspergillus niger | 226 | 213 | 228 | 273 | 190 | 195 | 245 | 206 | 222 | 209 | 172 |
| Botrytis spp. | 219 | 285 | 258 | 302 | 275 | 219 | 202 | 288 | 221 | 248 | 214 |
| Alternaria spp. | 81 | 97 | 76 | 89 | 58 | 76 | 75 | 175 | 117 | 174 | 167 |
| Penicillium paxilli | 135 | 162 | 215 | 142 | 127 | 161 | 103 | 115 | 238 | 190 | 200 |
| Penicillium oxalicum | 119 | 107 | 161 | 131 | 135 | 241 | 178 | 158 | 140 | 143 | 194 |
| Penicillium spp. | 50 | 123 | 179 | 177 | 128 | 138 | 146 | 163 | 148 | 115 | 184 |
| Can. alb/trop/dub | 261 | 236 | 235 | 230 | 250 | 213 | 276 | 244 | 245 | 237 | 194 |
| Can. glab/Sach & Kluv spp. | 146 | 165 | 196 | 128 | 160 | 215 | 185 | 217 | 215 | 177 | 225 |

TABLE 18-continued

Representative microarray data from raw water filtrate.

| | Sample ID | | | | | | | | | | Negative Control |
|---|---|---|---|---|---|---|---|---|---|---|---|
| | 2 H | 2 H | 9 D | 9 D | 21 | 21 | 23 | 23 | 25 | 25 | |
| Podosphaera spp. | 111 | 119 | 100 | 122 | 192 | 105 | 95 | 43 | 169 | 27 | 143 |
| Bile-tolerant Gram-negative High | 16026 | 9203 | 13309 | 8426 | 16287 | 14116 | 10557 | 17558 | 15343 | 14285 | 183 |
| Bile-tolerant Gram-negative Medium | 12302 | 11976 | 9259 | 10408 | 13055 | 10957 | 11242 | 8416 | 9322 | 11785 | 196 |
| Bile-tolerant Gram-negative Low | 5210 | 7921 | 3818 | 3984 | 7224 | 6480 | 4817 | 6933 | 5021 | 5844 | 240 |
| Total Enterobacteriaceae High | 193 | 248 | 389 | 357 | 215 | 214 | 198 | 220 | 276 | 208 | 210 |
| Total Enterobacteriaceae Med | 246 | 214 | 297 | 246 | 244 | 224 | 219 | 245 | 252 | 229 | 207 |
| Total Enterobacteriaceae Low | 165 | 140 | 158 | 119 | 151 | 180 | 150 | 167 | 182 | 174 | 132 |
| Total Coliform | 121 | 148 | 158 | 117 | 129 | 117 | 155 | 157 | 125 | 178 | 152 |
| Escherichia coli specific gene | 31821 | 115 | 132 | 155 | 127 | 62 | 86 | 121 | 59 | 90 | 234 |
| stx1 gene | 67 | 0 | 2 | 0 | 0 | 23 | 21 | 28 | 0 | 0 | 116 |
| stx2 gene | 17 | 36 | 174 | 0 | 61 | 47 | 0 | 51 | 33 | 0 | 85 |
| Salmonella specific gene | 181 | 172 | 245 | 172 | 178 | 212 | 157 | 243 | 174 | 156 | 146 |
| Bacillus spp. | 137 | 135 | 174 | 112 | 164 | 143 | 163 | 182 | 168 | 152 | 149 |
| Pseudomonas spp. | 271 | 74 | 332 | 56 | 366 | 133 | 91 | 114 | 60 | 179 | 555 |
| Escherichia coli/Shigella spp. | 103 | 124 | 221 | 124 | 90 | 144 | 130 | 121 | 137 | 143 | 158 |
| Salmonella enterica/enterobacter spp. | 124 | 98 | 131 | 119 | 136 | 88 | 121 | 77 | 128 | 140 | 124 |
| Erysiphe Group 2 | 278 | 221 | 237 | 230 | 245 | 254 | 250 | 220 | 205 | 236 | 233 |
| Trichoderma spp. | 105 | 157 | 204 | 152 | 180 | 154 | 130 | 161 | 201 | 180 | 150 |
| Escherichia coli | 429 | 431 | 551 | 576 | 549 | 406 | 407 | 484 | 556 | 551 | 293 |
| Aspergillus niger | 218 | 212 | 216 | 297 | 255 | 312 | 221 | 202 | 238 | 231 | 209 |
| Escherichia coli/Shigella spp. | 163 | 193 | 220 | 202 | 308 | 280 | 121 | 271 | 341 | 317 | 124 |
| Aspergillus fumigatus | 713 | 865 | 862 | 830 | 784 | 657 | 827 | 803 | 746 | 812 | 793 |
| Aspergillus flavus | 155 | 261 | 198 | 156 | 239 | 171 | 250 | 218 | 210 | 258 | 219 |
| Salmonella enterica | 136 | 98 | 85 | 43 | 109 | 47 | 23 | 123 | 70 | 100 | 135 |
| Salmonella enterica | 68 | 53 | 52 | 41 | 60 | 92 | 26 | 28 | 55 | 81 | 116 |

The data embodied in Table 18 were obtained from 5 well-water samples (named 2H, 9D, 21, 23, 25) along with 2 samples of milliQ laboratory water (obtained via reverse osmosis) referred to as "Negative Control". All samples were subjected to filtration on a sterile 0.4 um filter. Subsequent to filtration, the filters, with any microbial contamination that they may have captured, were then washed with the standard wash solution, exactly as described above for the washing of Cannabis and fruit. Subsequent to that washing, the suspended microbes in wash solution were then subjected to exactly the same combination of centrifugation (to yield a microbial pellet) then lysis and PCR of the unprocessed pellet-lysate (exactly as described above for Cannabis), followed by PCR and microarray analysis, also as described for Cannabis.

The data seen in Table 18 demonstrate that microbes collected on filtrates of environmental water samples can be analyzed via the same combination of raw sample genotyping, then PCR and microarray analysis used for Cannabis and fruit washes. The italicized elements of Table 18 demonstrate that the 5 unprocessed well-water samples all contain aerobic bacteria and bile tolerant gram-negative bacteria. The presence of both classes of bacteria is expected for unprocessed (raw) well water. Thus, the data of Table 18 demonstrate that this embodiment of the present invention can be used for the analysis of environmentally derived water samples.

The above teaching shows that unprocessed leaf and bud samples in Cannabis and hops may be washed in an aqueous water solution to yield a water-wash containing microbial pathogens which can then be analyzed via the present combination of RSG and microarrays. The above data also show that environmentally-derived well water samples may be analyzed by an embodiment. Further, if a water sample containing microbes were obtained from industrial processing sources (such as the water effluent from the processing of fruit, vegetables, grain, meat) and then analyzed directly, or after ordinary water filtration to concentrate the microbial complement onto the surface of the filter, that the present combination of RSG and microarray analysis would be capable of recovering and analyzing the DNA complement of those microbes.

Further, if an air sample containing microbes as an aerosol or adsorbed to airborne dust were obtained by air filtration onto an ordinary air-filter (such as used in the filtration of air in an agricultural or food processing plant, or on factory floor, or in a public building or a private home) that such air-filters could then be washed with a water solution, as has been demonstrated for plant matter, to yield a microbe-containing filter eluate, such that the present combination of Raw Sample Genotyping (RSG) and microarray analysis would be capable of recovering and analyzing the DNA complement of those microbes.

While the foregoing written description of an embodiments enables one of ordinary skill to make and use what is considered presently to be the best mode thereof, those of ordinary skill will understand and appreciate the existence of variations, combinations, and equivalents of the specific embodiment, method, and examples herein. The present disclosure should therefore not be limited by the above described embodiments, methods, and examples, but by all embodiments and methods within the scope and spirit of the present disclosure.

Example 4

Method of Using the 3-Dimensional Lattice Microarray System for Quantitative DNA Analysis.
Sample Processing
Harvesting Microbes from plant surface comprises the following steps:
 1. Wash the plant sample or tape pull in 1× phosphate buffered saline (PBS);

2. Remove plant material/tape;

3. Centrifuge to pellet cells and iscard supernatant;

3. Resuspend in PathogenDx® Sample Prep Buffer premixed with Sample Digestion Buffer;

3. Heat at 55° C. for 45 minutes;

3. Vortex to dissipate the pellet;

3. Heat at 95° C. for 15 minutes; and

3. Vortex and centrifuge briefly to obtain a sample comprising DNA from one or more types of microbes.

Addition of a Synthetic DNA to the Processed Sample

A known amount (known copy number) of synthetic DNA is added to the sample obtained in the sample processing step described above. The synthetic DNA has a length and sequence structure similar to that of the 16s (bacteria) or ITS2 (eukaryote) DNA sequence being amplified, but with a central region sequence that is distinct, to distinguish it from bacterial and eukaryotic DNA in the sample. The 5' and 3' end sequences of the synthetic DNA are designed to be substantially identical to a consensus sequence in the unknown bacterial or unknown eukaryotic DNA being queried, to allow amplification using the same pair of PCR primers used for amplification of the unknown DNA in the sample. Examples of such consensus sequences are shown in SEQ ID NO: 152 and SEQ ID NO: 153 (Table 19). These features allow unbiased amplification of both the synthetic DNA and the unknown microbial pool DNA in the sample. Examples of synthetic DNA sequences are shown in SEQ ID NO: 154 to SEQ ID NO: 157 (Table 19).

Amplification by PCR

The sample comprising the synthetic DNA sequence was amplified (PCR Reaction #1) using locus specific primer pairs (Tables 6 and 20). The product of PCR Reaction #1 (14) was then subjected to a second PCR reaction (PCR Reaction #2) using a pair of labeling primers (Tables 6 and 20), which additionally amplified and labeled the two targeted regions to generate fluorophore labeled amplicons. The product of the PCR Reaction #2 (504) was then diluted 1-1 with hybridization buffer (4×SSC+5×Denhardt's solution) and then applied directly to the microarray for hybridization.

Hybridization

Because the prior art method of microarray manufacture allows DNA to be analyzed via hybridization without the need for pre-treatment of the microarray surface, the use of the microarray is simple, and involves 6 manual or automated 1. Pipette the amplified DNA+binding buffer onto the microarray to which are immobilized oligonucleotide probe sequence for the pathogen gene being queried and the synthetic DNA used as internal reference standard (Tables 7-11 and 21).

2. Incubate for 30 minutes to allow DNA binding to the microarray (typically at room temperature, RT).

3. Remove the DNA+binding buffer by pipetting

4. Pipette 50 uL of wash buffer onto the microarray (0.4×SSC+0.5×Denhardt's) and incubate 5 min at RT.

5. Remove the wash buffer by pipetting.

6) Repeat steps 4 and 5

7) Perform image analysis at 532 nm and 635 nm to detect the probe spot location (532 nm) and PCR product hybridization (635 nm).

TABLE 19

Concensus sequences and Synthetic DNA sequences

SEQ ID NO: 152  Consensus sequence corresponding
                to the ITS2 domain in eukaryotes
                including yeast, mold fungi
                (TYM Quant Control)

NNNNNNNNNNNNNNNNNNNNNNNNNNNNNNNNNNNNNNNNACTTYCAAC
AAYGGATCTCTTGGTTCTGGCATCGATGAAGAACGCAGCNNNNNNNN
NNNNNNNNNNNNNNNNNNNNNNNNNNNNNGTGAATCATCGARTCTTT
GAACGCANNNNNNNNNNNNNNNNNNNNNNNNNNNNNNNNNNNNNNNN
NNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNN
NNNNNNNNNNNGCATATCAATAAGCGGAGGAAAANNNNNNNNNNNNN
NNNNNNNNNNNNNNNNNNNNNNNNNNN

SEQ ID NO: 153  Consensus sequence corresponding
                to the rDNA domain in prokaryotes NNNNNNNNNNNNNNNNNNNNNNNNNNNNNNNNNNNNNNNNCACAYTGGR
ACTGAGACACGGNNNNNNNCTCCTACGGGAGGCAGCAGTNNNNNNNN
NNNNNNNNNNNNNNNNNNNNNNNAYSSAGCMAYGCCGCGTGDRBGNN
NNNNNNNNNNNNNNNNNNNNNNNNNNNNNNNNNNNNNNNNNNNNNNN
NNNNNNNNNNNNNNNNNNNNNATTGACGTTACCCGCNNNNNNNNNNN
NNNNNNNNNNNNTGCCAGCAGCCGCGGTAATACNNNNNNNNNNNNNN
NNNNNNNNNNNNNNNNNNNNNNNNNNNNNNNNNNNNNNNNNNNNNNN
NNNNNNNNNNNN SEQ ID NO: 154  Synthetic DNA region compatible
                for use as an internal
                reference standard with the ITS2
                domain in eukaryotes TACTATTCAGCCTCTGTACGTGCTTCATGTAAATTGAACTTTCAAC
AACGGATCTCTTGGTTCTGGCATCGATGAAGAACGCAGCGACTTGC
GATAAGTAATGTGAATTGCAGAATTCAGTGCATCATAGAAACTATG
TACGCAAATTGCGCCCCTTGGTATTCCGGGGGGCATGCCTGTTCGA
GCGTCATTTCAACCCTCAAGCTTAGCTTGGTATTGAGTCTATGTCA
GTAATGGCAGGCTCTAAAATCAGTGGCGGCGCCGCTGGGTCCTGAA
CGTAGTAATATTTCTTGTCACCGTTTCTAGGTGTGCTTCTGTCTAT
ACCCAAATTCTTCTATGGTTGACCTCGGATCAGGTAGGGATACCCG
CTGAACTTAAGCATATCAATAAGCGGAGGAAAAGCACGCCGTCTAG
AAGCACGATCAGAGGCTGAATACTA SEQ ID NO: 155  Synthetic DNA region compatible
                for use as an internal
                reference standard with the rDNA
                domain in prokaryotes TACTATTCAGCCTCTGTACGTGCTTCATGTAAATTGACACACTGGA
ACTGAGACACGGTCCAGACTCCATCGGGAGCGAGCATGGGGGAATA
TTGCACAATGGGCGCAAGCCTGATGGACCCTAGCCGCCACTATGAA
GAAGGCCTTCGGGTTGTAAAGTACTTTCAGCGGGGAGGAGGGAATG
AAAGTATATACCTTTCGTCATGTACGTTACTCGCAGAAGAAGCACC
GGCTAACTCCGTGCCAGCAGCCGCGGTAATACGGAGGGTGCAAGCG
TTAATCGGAATTACTGGGCGCACGCCGTCTAGAAGCACGATCAGAG
GCTGAATACTA SEQ ID NO: 156  Synthetic DNA region compatible
                for use as an internal
                reference standard with the rDNA
                domain in prokaryotes
                including Bile-tolerant Gram-
                negative bacteria TACTATTCAGCCTCTGTACGTGCTTCATGTAAATTGACACACTGGA
ACTGAGACACGGTCCAGACTCCTGCAGGAGACGGCAGTGGGGAATA
TTGCACAATGGGCGCAAGCCTGATGTATCCCTGACGCAGATATGAA
GAAGGCCTTCGGGTTGTAAAGTACTTTCAGCGGGGAGGAAGGTCGT
AAAACTAATACACTTGCTGTTTGAACTTACCCAGAGAAGAAGCACC
GGCTAACTCCGTGCCAGCAGCCGCGGTAATACGGAGGGTGCAAGCG
TTAATCGGAATTACTGGGCGCACGCCGTCTAGAAGCACGATCAGAG
GCTGAATACTA

TABLE 19-continued

Concensus sequences and Synthetic DNA sequences

SEQ ID NO: 157   Synthetic DNA region compatible for use as an internal reference standard with the rDNA domain prokaryotes including the *Enterobacteriaceae* Family TACTATTCAGCCTCTGTACGTGCTTCATGTAAATTGACACACTGGA
ACTGAGACACGGTCCAGACTCCTAGCGGAGCGAGCAGTGGGGAATA
TTGCACAATGGGCGCAAGCCTGATGACGCCAGTCCGCTGGTATGAA
GAAGGCCTTCGGGTTGTAAAGTACTTTCAGCGGGGAGGAAGGAGGT
AAATGTAATACTCTTGCTACTTGAGCTTACCCCGAGAAGAAGCACC
GGCTAACTCCGTGCCAGCAGCCGCGGTAATACGGAGGGTGCAAGCG
TTAATCGGAATTACTGGGCGCACGCCGTCTAGAAGCACGATCAGAG
GCTGAATACTA

TABLE 20

Primers used for Locus PCR and Labeling PCR Amplification Reactions

| SEQ ID NO. | Primer target | Primer sequence |
|---|---|---|
| SEQ ID NO: 133 | Universal primers for preamplification of Fungal and Bacterial control fragments | TTCAGCCTCTGTACGTGCTTCATG |
| SEQ ID NO: 134 | Universal primers for preamplification of Fungal and Bacterial control fragments | TTCAGCCTCTGATCGTGCTTCTAG |
| SEQ ID NO: 135 | Fungal RSG Primers (All Fungus) | TTTACTTTCAACAAYGGATCTCTTGG |
| SEQ ID NO: 136 | Fungal RSG Primers (All Fungus) | CTTTTCCTCCGCTTATTGATATG |
| SEQ ID NO: 137 | Bacterial RSG Primers (All Bacteria) | TTTCACACTGGRACTGAGACACG |
| SEQ ID NO: 138 | Bacterial RSG Primers (All Bacteria) | TTTTGTATTACCGCGGCTGCTGGC |
| SEQ ID NO: 139 | Fungal Labeling Primers (All Fungus) | TTTGCATCGATGAAGAACGCAGC |
| SEQ ID NO: 140 | Fungal Labeling Primers (All Fungus) | TTTTCCTCCGCTTATTGATATGC |
| SEQ ID NO: 141 | Bacterial Labeling Primers | TTTCACACTGGRACTGAGACACGG |
| SEQ ID NO: 30 | Bacterial Labeling Primers | TTTTGTATTACCGCGGCTGCTGGCA |

TABLE 21

Oligonucleotide probe sequences

| SEQ ID NO: 132 | Negative control | TTTTTTCTACTACCTATGCTGATTCACTCTTTTT |
| --- | --- | --- |
| SEQ ID NO: 37 | Total Aerobic bacteria (High) | TTTTTTTTCCTACGGGAGGCAGTTTTTTT |
| SEQ ID NO: 38 | Total Aerobic bacteria (Medium) | TTTTTTTCCCTACGGGAGGCATTTTTTT |
| SEQ ID NO: 39 | Total Aerobic bacteria (Low) | TTTATTTTCCCTACGGGAGGCTTTTATTTT |
| SEQ ID NO: 47 | Bile-tolerant Gram-negative (High) | TTTTTCTATGCAGTCATGCTGTGTGTRTGTCTTTTT |
| SEQ ID NO: 48 | Bile-tolerant Gram-negative (Medium) | TTTTTCTATGCAGCCATGCTGTGTGTRTTTTTTT |
| SEQ ID NO: 49 | Bile-tolerant Gram-negative (Low) | TTTTTCTATGCAGTCATGCTGCGTGTRTTTTTTT |
| SEQ ID NO: 54 | Coliform/*Enterobacteriaceae* | TTTTTTCTATTGACGTTACCCGCTTTTTTT |
| SEQ ID NO: 41 | *Enterobacteriaceae* (Medium sensitivity) | TTTTTTCTATTGACGTTACCCGTTTTTTTT |
| SEQ ID NO: 40 | *Enterobacteriaceae* (Low sensitivity) | TTTATTCTATTGACGTTACCCATTTATTTT |
| SEQ ID NO: 86 | Total Yeast and Mold (High sensitivity) | TTTTTTTTGAATCATCGARTCTTTGAACGCATTTTTTT |
| SEQ ID NO: 88 | Total Yeast and Mold (Medium sensitivity) | TTTTTTTTGAATCATCGARTCTTTGAACGTTTTTTT |

TABLE 21-continued

Oligonucleotide probe sequences

| SEQ ID NO: 87 | Total Yeast and Mold (Low sensitivity) | TTTTTTTTGAATCATCGARTCTCCTTTTTT |
| SEQ ID NO: 142 | Total Aerobic Bacteria Quantitative Control (internal reference standard) | TTTTTTTTCCATCGGGAGCGAGTTTTTT |
| SEQ ID NO: 143 | Bile-tolerant Gram-negative Quantitative Control (internal reference standard) | TTTTTCTATGTATTCCTGATGTAGATRTGTCTTTTT |
| SEQ ID NO: 144 | Enterobacteriaceae/ Coliform Quantitative Control (internal reference standard) | TTTTTTCTCTTGAGCTTACCCCGTTTTTTT |
| SEQ ID NO: 145 | Total Yeast and Mold Quantitative Control (internal reference standard) | TTTTTTTTGCATCATAGAAACTTTGTACGCATTTTTT |
| SEQ ID NO: 103 | Candida spp. Group 2 | TTTTACTGTTTGGTAATGAGTGATACTCTCATTTT |
| SEQ ID NO: 146 | Golovinomyces spp. | TTTATTTAATCAATCCATCATCTCAAGTCTTTTT |
| SEQ ID NO: 108 | Fusarium spp | TTTTTTTTAACACCTCGCRACTGGAGATTTTTTT |
| SEQ ID NO: 107 | Fusarium oxysporum | TTTTTTTCTCGTTACTGGTAATCGTCGTTTTTTT |
| SEQ ID NO: 42 | Escherichia coli/ Shigella 1 | TTTTCTAATACCTTTGCTCATTGACTCTTT |
| SEQ ID NO: 74 | Salmonella enterica/Enterobacter 1 | TTTTTTTGTTGTGGTTAATAACCGATTTTT |
| SEQ ID NO: 72 | Pseudomonas spp. 3 | TTTATTTAAGCACTTTAAGTTGGGATTTTATTT |
| SEQ ID NO: 78 | Staphylococcus aureus 1 | TTTATTTTCATATGTGTAAGTAACTGTTTTATTT |
| SEQ ID NO: 147 | Listeria spp. | TTTATTTTGATAAGAGTAACTGCTTGCTTTATTT |
| SEQ ID NO: 45 | Bacillus spp. Group1 | TTTTTCAGTTGAATAAGCTGGCACTCTTTT |
| SEQ ID NO: 46 | Bacillus spp. Group2 | TTTTTTCAAGTACCGTTCGAATAGTTTTTT |
| SEQ ID NO: 90 | Aspergillus flavus 1 | TTTTTTCGCAAATCAATCTTTTTCCAGTCTTTTT |
| SEQ ID NO: 92 | Aspergillus fumigatus 1 | TTTCTTTTCGACACCCAACTTTATTTCCTTATTT |
| SEQ ID NO: 95 | Aspergillus niger 1 | TTTTTTCGACGTTTTCCAACCATTTCTTTT |
| SEQ ID NO: 100 | Botrytis spp | TTTTTTTCATCTCTCGTTACAGGTTCTCGGTTCTTTTTTT |
| SEQ ID NO: 116 | Penicillium oxalicum | TTTTTTACACCATCAATCTTAACCAGGCCTTTTT |
| SEQ ID NO: 117 | Penicillium paxilli | TTTTTTCCCCTCAATCTTTAACCAGGCCTTTTTT |
| SEQ ID NO: 118 | Penicillium spp | TTTTTTCAACCCAAATTTTTATCCAGGCCTTTTT |
| SEQ ID NO: 89 | Alternaria spp | TTTTTTCAAAGGTCTAGCATCCATTAAGTTTTTT |

TABLE 21-continued

Oligonucleotide probe sequences

| SEQ ID NO: 101 | Candida albicans | TTTTTTTTTGAAAGACGGTAGTGGTAAGTTTTTT |
| --- | --- | --- |
| SEQ ID NO: 105 | Cladosporium spp | TTTTTTTTGTGGAAACTATTCGCTAAAGTTTTTT |
| SEQ ID NO: 99 | Blumeria | TTTATTTGCCAAAAMTCCTTAATTGCTCTTTTTT |
| SEQ ID NO: 148 | Mucor spp. | TTTTTTCTCCAVVTGAGYACGCCTGTTTCAGTATCTTTTTT |
| SEQ ID NO: 120 | Podosphaera spp | TTTTTTGACCTGCCAAAACCCACATACCATTTTT |
| SEQ ID NO: 149 | Saccharomyces spp. | TTTATCTTAGGCGAACAATGTTCTTAAATCTTTT |
| SEQ ID NO: 150 | Aspergillus terreus | TTTTTTACGCATTTATTTGCAACTTGCCTTTTTT |
| SEQ ID NO: 151 | Podosphaera spp. | TTTTTCGTCCCCTAAACATAGTGGCTTTTT |

Image Analysis

Image Analysis was performed at two wavelengths (532 nm and 635 nm) on a raster-based confocal scanner: GenePix 4000B Microarray Scanner, with the following imaging conditions: 33% Laser power, 400 PMT setting at 532 nm/33% Laser Power, 700 PMT setting at 635 nm. FIG. 3 shows an example of the structure and hybridization performance of the microarray.

FIG. 3A reveals imaging of the representative microarray, described above, after hybridization and washing, as visualized at 635 nm. The 635 nm image is derived from signals from the (red) CY5 fluor attached to the 5' terminus of the bifunctional polymer linker OligodT which had been introduced during microarray fabrication as a positional marker in each microarray spot (see FIG. 1 and Table 3). The data in FIG. 3A confirm that the CY5-labelled OligodT has been permanently linked to the microarray surface, via the combined activity of the bi-functional linker and subsequent UV-crosslinking, as described in FIG. 1.

FIG. 3B reveals imaging of the representative microarray described above after hybridization and washing as visualized at 532 nm. The 532 nm image is derived from signals from the (green) CY3 fluor attached to the 5' terminus of PCR amplified DNA obtained during PCR Reaction #2. It is clear from FIG. 3B that only a small subset of the 48 discrete probes bind to the CY3-labelled PCR product, thus confirming that the present method of linking nucleic acid probes to form a microarray (FIG. 1) yields a microarray product capable of sequence specific binding to a (cognate) solution state target. The data in FIG. 3B reveal the underlying 3-fold repeat of the data (i.e., the array is the same set of 48 probes printed three times as 3 distinct sub-arrays to form the final 48×3=144 element microarray. The observation that the same set of 48 probes can be printed 3-times, as three repeated sub-domains show that the present invention generates microarray product that is reproducible.

FIG. 3C reveals imaging of the representative microarray, described above, after hybridization and washing, as visualized with both the 532 nm and 635 nm images superimposed. The superimposed images display the utility of parallel attachment of a CY5-labelled OligodT positional marker relative to the sequence specific binding of the CY3-labelled PCR product.

Example 5

Quantitation of Absolute DNA Copy Number

Figure 17A:
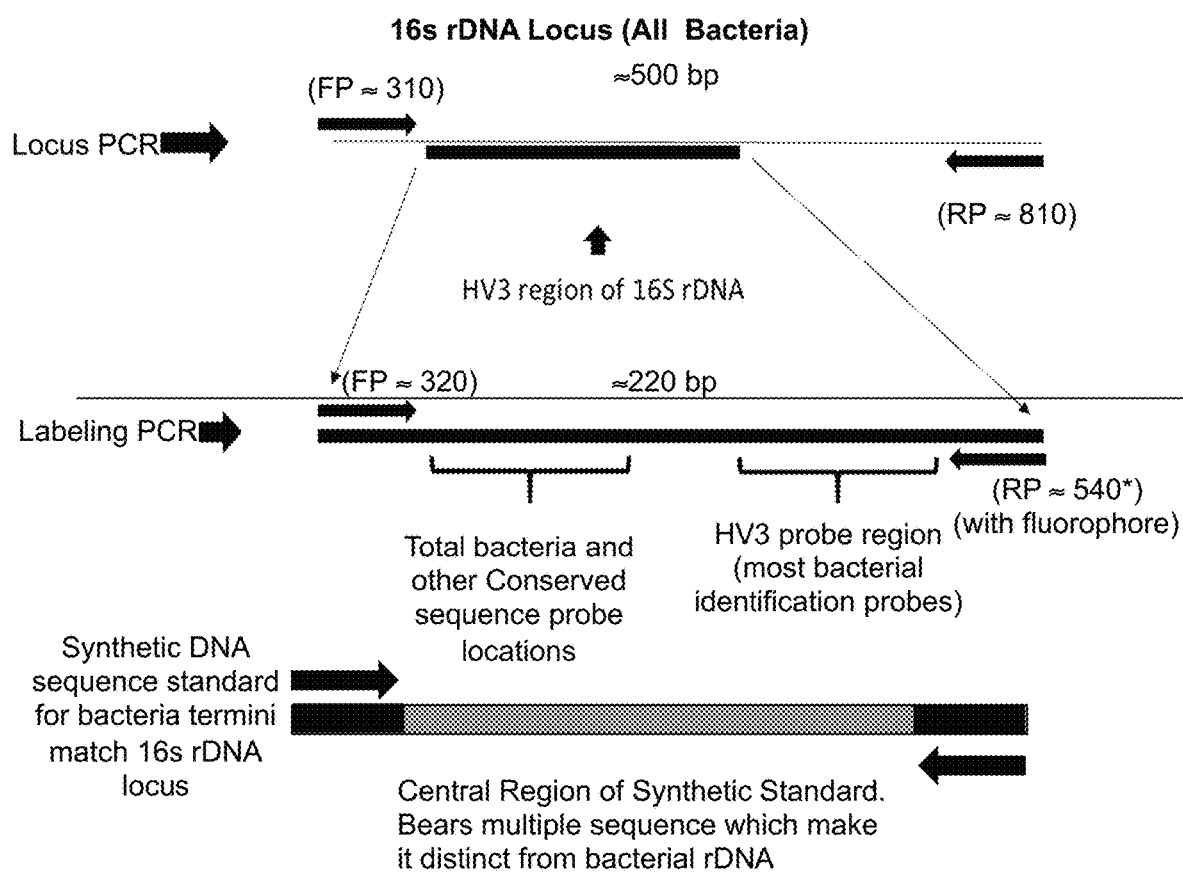
FIG. 17A is a graphical representation of the position of PCR primers used to PCR amplify unpurified bacterial contamination in a *Cannabis* wash or related plant wash. Two sets of PCR primers are used. The first set of forward primer (FP) and reverse primer (RP) support a "Locus PCR" step wherein amplification of bacterial recombinant DNA (rDNA) is based on the 16s locus present in all bacteria. The second set of primers support a "Labeling PCR" step wherein the primers are dye labeled and specific to the bacteria of interest. The two PCR steps in this invention differs from FIGS. 4A and 4B in the addition of a known copy number of a synthetic DNA sequence to the sample, as an internal reference standard, prior to performing the first PCR wherein, the synthetic DNA sequence is distinguishable from the bacterial sequences in the sample and have end sequences complementary to the sequence in the FP and the RP, so that the synthetic DNA sequence is co-amplified with the bacterial sequence in the sample.
Figure 17B:
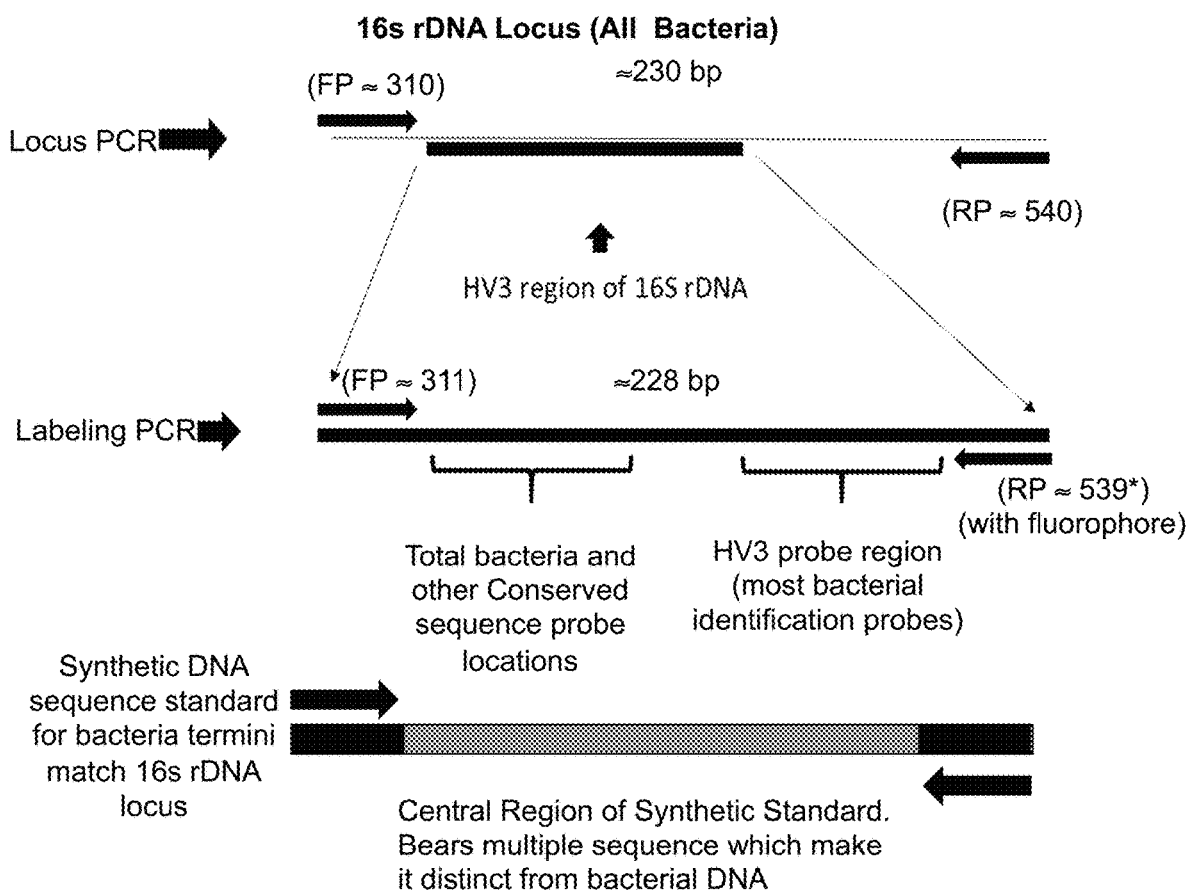
FIG. 17B is a graphical representation of the position of PCR primers used to PCR amplify unpurified bacterial contamination in a *Cannabis* wash or related plant wash. Two sets of PCR primers are used. The first set of forward primer (FP) and reverse primer (RP) support a "Locus PCR" step wherein amplification of bacterial genomic DNA (DNA) is based on the 16s locus present in all bacteria. The second set of primers support a "Labeling PCR" step wherein the primers are dye labeled and specific to the bacteria of interest. The two PCR steps in this invention differs from FIGS. 4A and 4B in the addition of a known copy number of a synthetic DNA sequence to the sample, as an internal reference standard, prior to performing the first PCR wherein, the synthetic DNA sequence is distinguishable from the bacterial sequences in the sample and have end sequences complementary to the sequence in the FP and the RP, so that the synthetic DNA sequence is co-amplified with the bacterial sequence in the sample.
Figure 18:
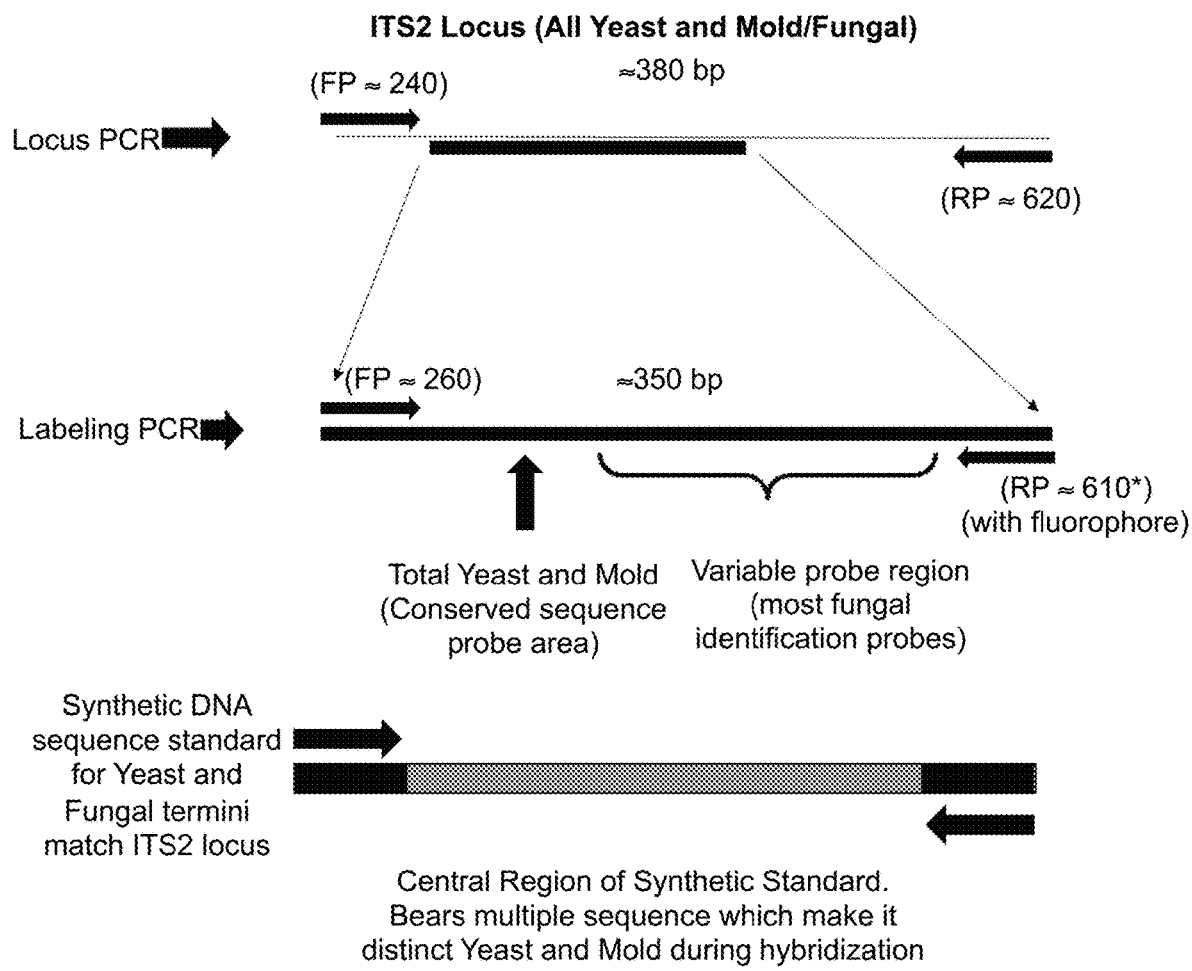
FIG. 18 is a graphical representation of the position of PCR primers used to PCR amplify unpurified eukaryotic (e.g. yeast or mold) contamination in a *Cannabis* wash or related plant wash. Two sets of PCR primers are used. The first set of forward primer (FP) and reverse primer (RP) support a "Locus PCR" step wherein amplification of the eukaryotic DNA is based on the ITS2 locus present in all eukaryotes. The second set of primers support a "Labeling PCR" step wherein the primers are dye labeled and specific to the eukaryotes of interest. The two PCR steps in this invention differs from FIGS. 4A and 4B in the addition of a known copy number of a synthetic DNA sequence to the sample, as an internal reference standard, prior to performing the first PCR wherein, the synthetic DNA sequence is distinguishable from the eukaryotic sequences in the sample and have end sequences complementary to the sequence in the FP and the RP, so that the synthetic DNA sequence is co-amplified with the eukaryotic sequence in the sample.

Quantitation of absolute DNA copy number for a microbe of interest in a sample as disclosed in the present invention is achieved by introducing into the sample, a known copy number of a synthetic DNA before the first PCR amplification step. The synthetic DNA has a length and sequence structure similar to that of the 16s (bacteria) or ITS2 (eukaryote) DNA amplicons generated in the first PCR (FIGS. 17A-17B and 18), but with a central region sequence that is distinct, to distinguish it from bacterial and eukaryotic DNA in the sample. The 5' and 3' end sequences of the synthetic DNA are designed to be substantially identical to a consensus sequence in the unknown bacterial or unknown eukaryotic DNA being queried, to allow amplification using the same pair of PCR primers used for amplification of the unknown DNA in the sample. These features allow the synthetic DNA to be amplified by the same pair of PCR primers used to amplify the hypervariable region of the unknown microbes which are being queried. As a result, the synthetic DNA is indistinguishable from the microbial pool DNA in the sample in terms of primer/template hybridization during the first and second PCR amplification reactions. This ensures unbiased amplification of the synthetic (internal reference standard) and microbial (unknown) DNA, such that signal intensity for amplicons from the queried DNA and synthetic DNA are proportional to the original copy number of each DNA respectively (discussed below). Examples of such consensus sequences are shown in SEQ ID NO: 152 and SEQ ID NO: 153 (Table 19). Examples of synthetic DNA sequences are shown in SEQ ID NO: 154 to SEQ ID NO: 157 (Table 19).

PCR, as deployed in the present microarray-based analysis is generally performed as a type of end-point PCR. Although in its simplest approximation, the polymerase chain reaction (PCR) has been described as a type of chain reaction because in the beginning of the PCR reaction process, when the DNA target strands are extremely dilute, each cycle of PCR will, in general lead to a geometric increase in product DNA, nearly exactly a 2-fold increase in amplified DNA product for each new PCR thermal cycle. If such a 2-fold increase were to occur indefinitely, the concentration of amplified DNA product should theoretically increase exponentially to infinity. In practice however, such a limitless DNA product increase does not occur, and one observes the well-known "S-shaped" sigmoidal PCR response curve wherein one or more components of the PCR reactant mixture or, one or more components of the PCR product mixture leads to a saturation in amplicon production. It is generally believed that such "leveled-off" S-shaped PCR curves occurs due to consumption of the PCR primers in the reaction mixture. Therefore, in the present invention, the concentration of PCR primers in both of the PCR reactions (first, locus PCR and second, labeling PCR, see FIGS. 17A, 17B and 18) is intentionally kept at a large molar excess, so that primer depletion cannot contribute to saturation of PCR amplification. However, even with an excess of PCR reactants, it was observed that amplicon generated from both PCRs continue to "level-off" to produce a complex "end-point" PCR wherein the number of amplicons will no longer increase despite increasing concentration of the reactants. This saturation in response occurs due to enzymatic end-product inhibition. In the present invention, such inhibition is enabled to generate a substantial amount of PCR product, so as to ensure that microarray hybridization remains highly selective and sensitive to low microbial density in the sample.

The key to the present invention is therefore based upon deployment of the above-mentioned synthetic DNA internal reference standards so that even as the PCR reaction saturates by means of end-product inhibition (or any other mechanism of PCR leveling) the relative abundance of any DNA derived from an unknown amount of its microbial source, can be directly compared to that of the internal reference standard, so that the abundance of the unknown DNA, relative to that of the known synthetic DNA (internal reference standard) becomes insensitive to the extent of PCR reaction. This effect was exploited in this invention with the understanding that as the PCR reaction approaches saturation (associated with end-product inhibition), the amounts of various amplified species begin to interact as discussed below:

i) Unknown DNA Copies=Standard DNA Copies

When the number of copies of the synthetic DNA (standard species) is equal to the number of copies of an microbial DNA (unknown species) in the original sample, the ratio of microbial DNA to synthetic DNA will be equal to 1 from the beginning of the PCR reaction (where amplification is exponential) to the end of the PCR reaction (where amplification begins to saturate via end-product inhibition).

$C_n/C_o = S_n/S_o$ where, $C_n$=the number of microbial DNA copies of each type (n) present in the original sample mixture added to the first of two tandem PCR reactions used to prepare amplicons for microarray analysis,
$C_o$=the number of known synthetic DNA copies (internal reference standard) added to the first of two PCR reactions used to prepare amplicons for microarray analysis,
$S_n$=relative fluorescence units (RFU) signal data obtained after PCR amplification, and microarray hybridization of the nth microbial species, followed by image analysis,
$S_o$=relative fluorescence units (RFU) signal data obtained after PCR amplification, and microarray hybridization of the synthetic DNA species, followed by image analysis, ii) Unknown DNA Copies>Standard DNA Copies When the microbial DNA (unknown species) were in large excess over the known synthetic DNA (standard species), the ratio of microbial DNA to synthetic DNA will be >1. In this situation, at the beginning of the PCR reaction, the relative abundance of amplicons (PCR product) will be a truthful representation of the original input strand ratio (unknown:standard). As the reaction proceeds towards saturation however, the more abundant species (unknown species in this case) will approach end-product saturation first, either due to consumption of one or more reactants or due to enzyme inhibition by PCR reaction products—pyrophosphate and/or amplicons. As a result, amplification of the relatively less abundant standard species will be inhibited. In this situation, abundance of amplified DNA product species will retain the correct qualitative relationship of "unknown species>standard species", whereas the ratio of DNA products will no longer be linearly related to the unknown: standard ratio in the original input sample.

$C_n/C_o \neq S_n/S_o$

Such a non-linear relationship between input and response is well known in chemical and physical analysis such as the relationship between grain density versus photon exposure in chemical film or in a charge-coupled device (CCD) where, the relative brightness of photographic inputs are maintained in relative rank order in the resulting image, yet a detailed understanding of the non-linear response is required to predict relative abundance of the original inputs (analogous to DNA copy number in the original sample) from the response data (analogous to PCR product signal after amplification and microarray hybridization).

iii) Unknown DNA Copies<Standard DNA Copies

When the microbial DNA (unknown species) were less than the known synthetic DNA (standard species), the ratio of microbial DNA to synthetic DNA will be <1. In this situation, at the beginning of the PCR reaction, the relative abundance of amplicons (PCR product) will be a truthful representation of the original input strand ratio (unknown: standard). As the reaction proceeds towards saturation however, the more abundant species (standard species in this case) will approach end-product saturation first, either due to consumption of one or more reactants or due to enzyme inhibition by PCR reaction products—pyrophosphate and/or amplicons. As a result, amplification of the relatively less abundant unknown species will be inhibited. In this situation, abundance of amplified DNA product species will retain the correct qualitative relationship of "unknown species>standard species", whereas the ratio of DNA products. will no longer be linearly related to the unknown: standard ratio in the original input sample;

$C_n/C_o \neq S_n/S_o$

Such a non-linear relationship between input and response is well known in chemical and physical analysis such as the relationship between grain density versus photon exposure in chemical film or in a charge-coupled device (CCD) where, the relative brightness of photographic inputs are maintained in relative rank order in the resulting image, yet a detailed understanding of the non-linear response is required to predict relative abundance of the original inputs (analogous to DNA copy number in the original sample) from the response data (analogous to PCR product signal after amplification and microarray hybridization).

The non-linear relationships described above are similar to that observed in chemical and physical analysis, such as the relationship between grain density versus photon exposure in chemical films or charge-coupled devices (CCD) where, the relative brightness of photographic inputs are maintained in relative rank order in the resulting image, yet a detailed understanding of the non-linear response is required to predict relative abundance of the original inputs (analogous to DNA copy number in the original sample) from the response data (analogous to PCR product signal after amplification and microarray hybridization). In the present invention, it is determined that the observed competition between unknown microbial DNA and standard DNA display a useful and generally unexpected "X-shaped" relationship, of the kind displayed in FIG. 19A.

P=A constant which relates the Experimental Microarray Data ratio ($S_n/S_o$) to the concentration of amplified PCR product which binds to the microarray. In general, for the examples presented here (FIGS. 19A and 19B), P=1.

In general X can be a linear function or exponential or related functional form or a constant which is itself a function of PCR parameters and conditions of microarray analysis and imaging. Based on representative data shown in the present invention, X is approximated as a constant with a value near to 2.

TABLE 22

Figure 19A:
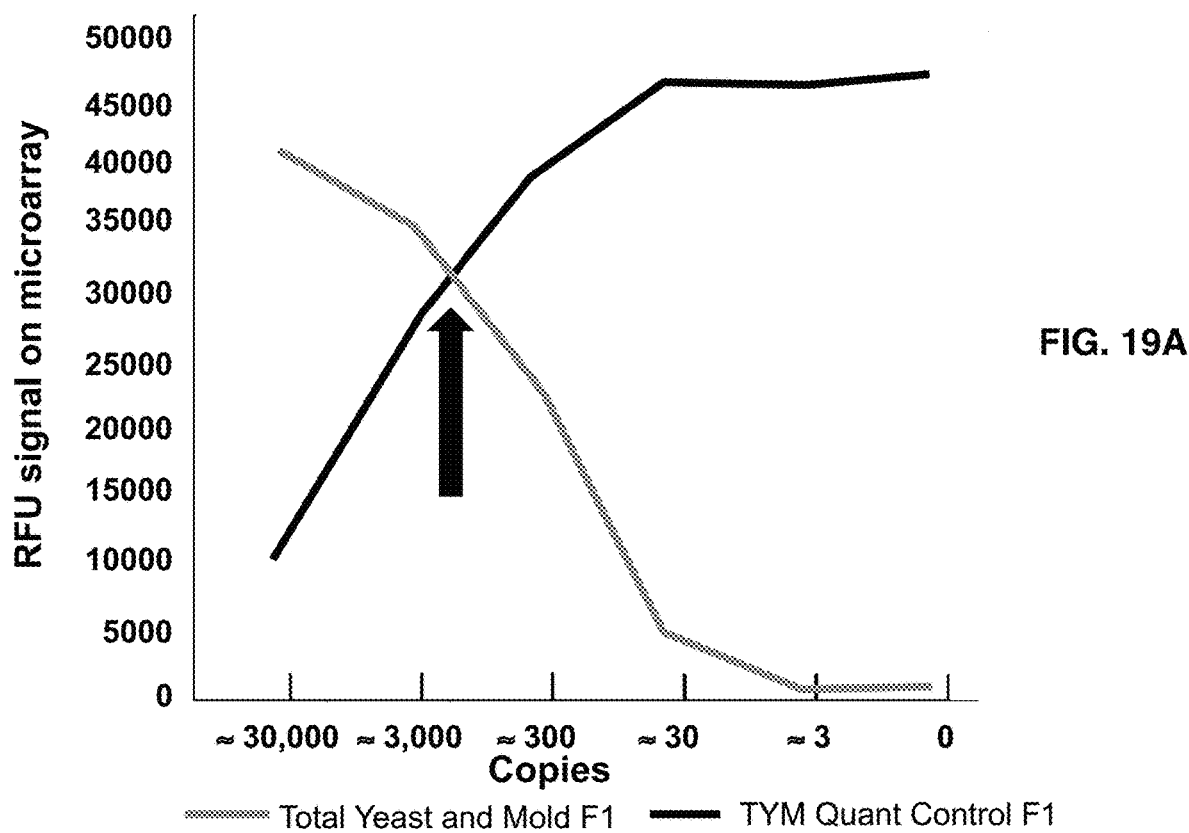
FIG. 19A illustrates calculated copies of ITS2 regions in *Aspergillus flavus* varied to deliver approximately 0 to 30,000 copies per PCR reaction performed in the presence of 3000 copies (known amount) of Total Yeast and Mold Quantitative Control (TYM Quant Control) as the internal reference standard, using a Total Yeast and Mold nucleic acid probe for *Aspergillus* and a TYM Quant Control probe for the internal standard. The point of crossover at 3000 copies, each for *Aspergillus* and TYM Quant Control (arrow) between the titration curves for *Aspergillus* (unknown copy number) and the TYM internal reference standard (known copy number) reveals the copy number of *Aspergillus* DNA in the sample.

Experimental Data $S_n/S_o$ as a function of Experimental Copy Number Data $C_n/C_o$ from the Representative PCR-Microarray Validation Studies in FIG. 19A

| $C_n/C_o$ Measured DNA Copy Number Ratio in the Original Sample to be analyzed by PCR-Microarray $C_o$ = 3000 copies | $(S_n/S_o)^2$ Adjusted Experimental Microarray Data Ratio using X = 2 | $S_n/S_o$ Measured Experimental Microarray Data Ratio |
|---|---|---|
| 0.01 | 0.01 | 0.1 (5,000 RFU/45,000 RFU) |
| 0.1 | 0.25 | 0.5 (20,000 RFU/40,000 RFU) |
| 1 | 1 | 1 (32,000 RFU/32,000 RFU) |
| 10 | 5.3 | 2.3 (40,000 RFU/15,000 RFU) |

Analysis of Microbial DNA (rDNA or ITS2) Copy Number by PCR-Microarray.

Figure 19B:
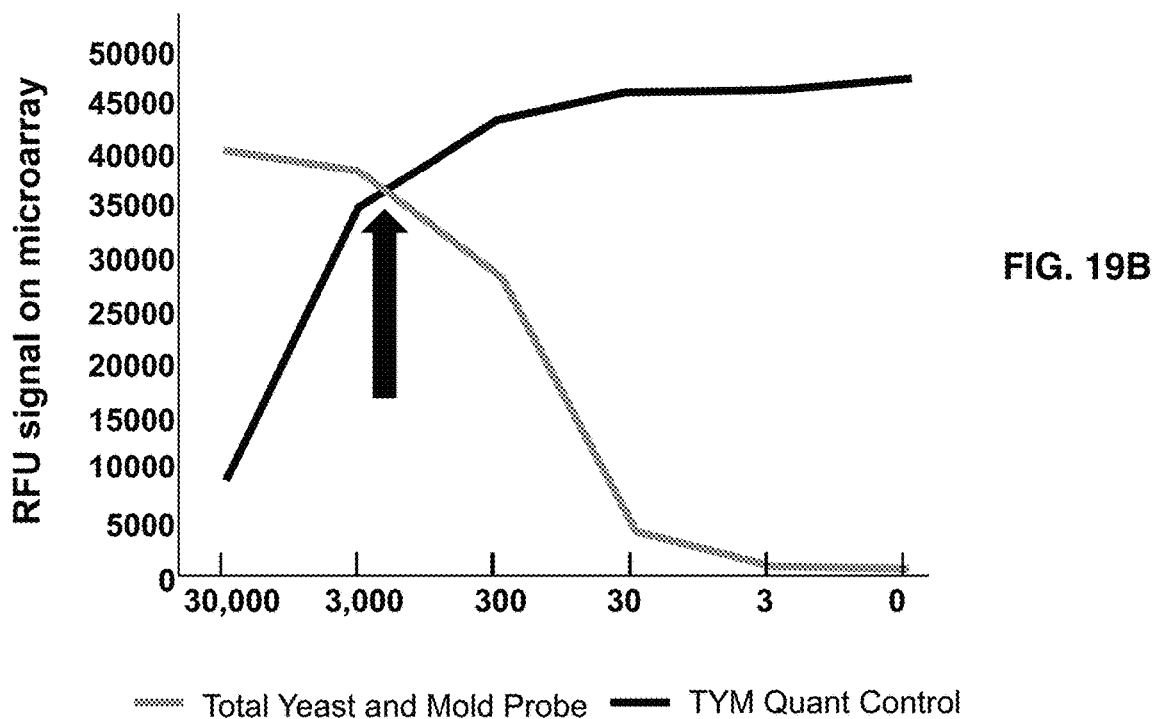
FIG. 19B illustrates calculated copies of ITS2 regions in *Saccharomyces cerevisiae* varied to deliver approximately 0 to 30,000 copies per PCR reaction performed in the presence of 3000 copies (known amount) of Total Yeast and Mold Quantitative Control (TYM Quant Control) as the internal reference standard, using a Total Yeast and Mold nucleic acid probe for *Saccharomyces* and a TYM Quant Control probe for the internal standard. The point of crossover at 3000 copies, each for *Saccharomyces* and TYM Quant Control (arrow) between the titration curves for *Saccharomyces* (unknown copy number) and the TYM internal reference standard (known copy number) reveals the copy number of *Saccharomyces* DNA in the sample.

"Crossover" titration data of the kind shown in FIGS. 19A and 19B were determined to be intrinsic to the PCR-Microarray analysis described in this application. As target microbial DNA copy number is increased, with synthetic DNA copy number being held constant, the products of the microbial PCR reaction, and hence signals due to binding of those products to cognate probes on the microarray surface increase with increasing microbial DNA copy number, whereas the signals obtained from the (fixed) matched internal reference standard decrease in concert (FIGS. 19A-19B). The two curves cross-over at or near copy number equivalency (arrow, FIG. 19A-19B) where the number of microbial DNA copies become equal to the number of internal reference standard DNA copies.

Over the range of PCR conditions consistent with the present invention (i.e. conditions of PCR signals saturating due to competition between the unknown microbial DNA and an added DNA standard) the relation between the DNA input and output can be approximated as, $$C_n/C_o = P(S_n/S_o)^x \text{ where,} \qquad \text{Equation \#1}$$

$C_n$=the number of microbial DNA copies of each type (n) present in the original sample mixture added to the first of two tandem PCR reactions used to prepare amplicons for microarray analysis, $C_o$=the number of known synthetic DNA copies (internal reference standard) added to the first of two PCR reactions used to prepare amplicons for microarray analysis, $S_n$=relative fluorescence units (RFU) signal data obtained after PCR amplification, and microarray hybridization of the nth microbial species, followed by image analysis, $S_o$=relative fluorescence units (RFU) signal data obtained after PCR amplification, and microarray hybridization of the synthetic DNA species, followed by image analysis, X=a complex exponential factor which defines the functional relationship between the Experimental Microarray Data Ratio ($S_n/S_o$) to the underlying ratio of microbial DNA copies vs synthetic DNA standard copies present in the original sample ($C_n/C_o$).

In general, the function (X) relates original DNA Copy Number Ratio ($C_n/C_o$) to the Experimental Microarray Data Ratio ($S_n/S_o$) generated from the microarray hybridization RFU signal data. Function (X) can have different functional forms depending on details of the PCR reaction and microarray hybridization. However, it was determined that, if (1) All microbial DNA PCR reactions use the same pair of PCR primers as the internal reference standard; and (2) All hybridization probes applied to the microarray surface have the same affinity for their cognate DNA sequence produced by the PCR reactions; and (3) All PCR products are labeled with the same fluorescent dye for optical detection; then, X will approach a constant, which in the data presented in FIG. 19A assumes a value close to 2. Under these conditions Equation #1 may be simplified as $$C_n = C_o(S_n/S_o)^2 \qquad \text{Equation \#2}$$

where $C_n$=The number of microbial DNA copies present in the original sample.

$C_o$=Is adjusted by adding a known number of synthetic DNA standard copies to the original sample.

X=2 as estimated from experimental data, as in FIG. 19A

P=1 as determined by experiment, as in FIG. 19A

For FIG. 19A, the synthetic DNA reference standard copy number ($C_o$) was intentionally held at 3,000 but may be set at any other value including but not limited to 100, 500, 3,000 and 5,000 depending on the range of unknown microbial copies which might be encountered.

In a specific implementation of the present invention for microbial testing in food or *Cannabis* or other plant matter or for water testing, State or Federal Regulations might require a specific minimum allowable value for microbial contamination. Based on that regulated value and knowledge of the number of rDNA or ITS-2 DNA copies per microbial genome, the adjustable standard copy number value $C_o$ added to the original sample before the PCR and Microarray hybridization steps can be seen as having value as a way to "dial" regulatory standards directly into the PCR-Microarray assay.

What is claimed is:

1. A method for simultaneously quantitating copy number of DNA for one or more pathogens and a plant in a plant tissue sample, comprising the steps of:
   a) obtaining a plant tissue sample comprising one or more pathogens;
   b) isolating total nucleic acids comprising DNA and non-DNA nucleic acids from the plant and the pathogens in the plant tissue sample;
   c) adding a known copy number of at least one synthetic DNA sequence as an internal reference standard, each of said synthetic DNA sequences comprising:
      a central region having a nucleotide sequence distinct from signature sequence determinants in the pathogen DNA and the plant DNA; and
      a 5' end and a 3' end having nucleotide sequences substantially identical to a consensus sequence in the pathogen DNA;
   d) amplifying, in a first amplification in a single assay, the pathogen DNA and the at least one synthetic DNA sequence in the total nucleic acids using at least one first primer pair selective for the pathogen DNA and the synthetic DNA and at least one second primer pair selective for the plant DNA to generate one or more pathogen DNA-specific first amplicons, plant DNA-specific second amplicons and synthetic DNA-specific third amplicons;
   e) amplifying, in a second amplification, using the one or more pathogen-specific first amplicons, the plant DNA-specific second amplicons and the synthetic DNA-specific third amplicons as a template and at least one first fluorescent labeled third primer pair and at least one second fluorescent labeled fourth primer pair to generate pathogen DNA-specific first fluorescent labeled fourth amplicons, plant DNA-specific second fluorescent labeled fifth amplicons and first fluorescent labeled synthetic DNA-specific sixth amplicons;

f) hybridizing the pathogen DNA-specific first fluorescent labeled fourth amplicons, the plant DNA-specific second fluorescent labeled fifth amplicons and the first fluorescent labeled synthetic DNA-specific sixth amplicons with nucleic acid probes specific for signature sequence determinants in the pathogen DNA, in the plant DNA and in the synthetic DNA, respectively, said nucleic acid probes immobilized at specific known positions on a 3-dimensional lattice microarray via third fluorescent labeled bifunctional polymer linkers;

g) washing the 3-dimensional lattice microarray at least once;

h) imaging the 3-dimensional lattice microarray to detect a first fluorescent signal corresponding to the first fluorescent labeled fourth amplicons or the first fluorescent labeled sixth amplicons, a second fluorescent signal corresponding to the second fluorescent labeled fifth amplicons and a third fluorescent signal corresponding to the nucleic acid probes immobilized at the specific known positions on the 3-dimensional lattice microarray via the third fluorescent labeled bifunctional polymer linkers;

i) superimposing the first fluorescent signal and the second fluorescent signal with the third fluorescent signal to obtain a superimposed signal image;

j) comparing the sequence of the nucleic acid probe at one or more superimposed signal positions on the microarray with a database of signature sequence determinants for a plurality of pathogen DNAs and plant DNAs thereby identifying the pathogens and the plant in the sample;

k) correlating mathematically, a first fluorescent signal intensity from the pathogen DNA-specific first fluorescent labeled fourth amplicons with a first fluorescent signal intensity from the synthetic DNA-specific first fluorescent labeled sixth amplicons and the known copy number of the synthetic DNA, thereby quantitating copy number of the pathogen DNA in the sample; and l) correlating mathematically, a second fluorescent signal intensity from the plant DNA-specific second fluorescent labeled fifth amplicons with a first fluorescent signal intensity from the synthetic DNA-specific first fluorescent labeled sixth amplicons and the known copy number of the synthetic DNA, thereby quantitating copy number of the plant DNA in the sample.

2. The method of claim 1, wherein the pathogen is a bacterium, a fungus, a virus, a yeast, an algae or a protozoan or a combination thereof.

3. The method of claim 1, wherein the pathogen is a bacterium, said consensus sequence comprising the nucleotide sequence of SEQ ID NO: 153, the first primer pair comprising the nucleotide sequences of SEQ ID NOS: 1 and 2, or SEQ ID NOS: 3 and 4, or SEQ ID NOS: 5 and 6, or SEQ ID NOS: 7 and 8, or SEQ ID NOS: 9 and 10, or SEQ ID NOS: 11 and 12, or SEQ ID NOS: 137 and 138.

4. The method of claim 1, wherein the pathogen is a bacterium, said consensus sequence comprising the nucleotide sequence of SEQ ID NO: 153, the first fluorescent labeled third primer pair comprising the nucleotide sequences of SEQ ID NOS: 19 and 20, or SEQ ID NOS: 21 and 22, or SEQ ID NOS: 23 and 24, or SEQ ID NOS: 25 and 26, or SEQ ID NOS: 27 and 28, or SEQ ID NOS: 29 and 30, or SEQ ID NOS: 141 and 30.

5. The method of claim 1, wherein the pathogen is a bacterium, the nucleic acid probes specific to the bacterium comprising the nucleotide sequences of SEQ ID NOS: 37-85.

6. The method of claim 1, wherein the pathogen is a bacterium, the synthetic DNA sequence comprising the nucleotide sequences of SEQ ID NO: 155, SEQ ID NO: 156 and SEQ ID NO: 157 that hybridize to synthetic DNA sequence specific nucleic acid probes comprising the nucleotide sequences of SEQ ID NO: 142, SEQ ID NO: 143 and SEQ ID NO: 144, respectively.

7. The method of claim 1, wherein the pathogen is a fungus, said consensus sequence comprising the nucleotide sequence of SEQ ID NO: 152, the first primer pair comprising the nucleotide sequences of SEQ ID NOS: 13 and 14, or SEQ ID NOS: 15 and 16, or SEQ ID NOS: 135 and 136.

8. The method of claim 1, wherein the pathogen is a fungus, said consensus sequence comprising the nucleotide sequence of SEQ ID NO: 152, the first fluorescent labeled third primer pair comprising the nucleotide sequence of SEQ ID NOS: 31 and 32, or SEQ ID NOS: 33 and 34, or SEQ ID NOS: 139 and 140.

9. The method of claim 1, wherein the pathogen is a fungus, said nucleic acid probes specific to the fungus comprising the nucleotide sequences of SEQ ID NOS: 86-125.

10. The method of claim 1, wherein the pathogen is a fungus, the synthetic DNA sequence comprising the nucleotide sequence of SEQ ID NO: 154 that hybridizes to synthetic DNA sequence specific nucleic acid probes comprising the nucleotide sequences of SEQ ID NO: 145.

11. The method of claim 1, wherein the plant is a *Humulus* or a *Cannabis*.

12. The method of claim 1, wherein the plant is *Cannabis*, said second primer pair comprising the nucleotide sequence of SEQ ID NOS: 17 and 18.

13. The method of claim 1, wherein the plant is *Cannabis*, said second fluorescent labeled fourth primer pair comprising the nucleotide sequence of SEQ ID NOS: 35 and 36.

14. The method of claim 1, wherein the plant is *Cannabis*, the nucleic acid probes comprising the nucleotide sequences of SEQ ID NOS: 126-128.

15. The method of claim 1, wherein the steps of correlating mathematically is performed using the relationship:

$$C_n/C_o = P(S_n/S_o)^x \text{ where,}$$

$C_n$ is the copy number of pathogen DNA or plant DNA of each type n of pathogen or plant species to be quantitated, $C_o$ is the known copy number of the synthetic DNA sequence added to the sample prior to performing the first amplification step, $S_n$ is the first fluorescent signal intensity in relative fluorescence units (RFU) from the pathogen DNA-specific first fluorescent labeled third amplicons that hybridized to the pathogen DNA-specific nucleic acid probes at the specific known positions on the 3-dimensional lattice microarray for each of the type n of pathogen species, or the second fluorescent signal intensity in RFU from the plant DNA-specific second fluorescent labeled fourth amplicons that hybridized to the plant DNA-specific nucleic acid probes at the specific known positions on the microarray for each of the type n plant species, $S_o$ is first fluorescent signal intensity in RFU from the synthetic DNA-specific first fluorescent labeled sixth amplicons that hybridized to the synthetic DNA sequence-specific nucleic acid probes at the specific known positions on the 3-dimensional lattice microarray, P is a constant ranging from about 0.1 to about 10 and X is a an exponential factor ranging from about 1 to about 3.

* * * * *